(12) United States Patent
Kim et al.

(10) Patent No.: US 10,583,197 B2
(45) Date of Patent: *Mar. 10, 2020

(54) ANTIBODY-ACTIVE AGENT CONJUGATES AND METHODS OF USE

(71) Applicant: LegoChem Biosciences, Inc., Daejeon (KR)

(72) Inventors: Yongzu Kim, Daejeon (KR); Taekyo Park, Daejeon (KR); Sungho Woo, Daejeon (KR); Hyangsook Lee, Daejeon (KR); Sunyoung Kim, Daejeon (KR); Jongun Cho, Daejeon (KR); Doohwan Jung, Daejeon (KR); Youngun Kim, Daejeon (KR); Hyunjin Kwon, Daejeon (KR); Kyuman Oh, Daejeon (KR); Yunseo Chung, Daejeon (KR); Yun-Hee Park, Daejeon (KR)

(73) Assignee: LegoChem Biosciences, Inc., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/612,766

(22) Filed: Jun. 2, 2017

(65) Prior Publication Data

US 2018/0021451 A1 Jan. 25, 2018

Related U.S. Application Data

(60) Continuation of application No. 14/517,616, filed on Oct. 17, 2014, now Pat. No. 9,669,107, which is a continuation of application No. 14/181,648, filed on Feb. 15, 2014, now abandoned, which is a division of application No. 13/466,875, filed on May 8, 2012, now abandoned.

(60) Provisional application No. 61/483,698, filed on May 8, 2011.

(51) Int. Cl.

| A61K 47/68 | (2017.01) |
| C07K 16/28 | (2006.01) |
| C07K 16/32 | (2006.01) |
| C12Q 1/48 | (2006.01) |
| A61K 47/65 | (2017.01) |
| A61K 47/54 | (2017.01) |
| A61K 47/55 | (2017.01) |

(52) U.S. Cl.
CPC ........ *A61K 47/6811* (2017.08); *A61K 47/549* (2017.08); *A61K 47/55* (2017.08); *A61K 47/65* (2017.08); *A61K 47/6803* (2017.08); *A61K 47/6817* (2017.08); *A61K 47/6849* (2017.08); *A61K 47/6851* (2017.08); *A61K 47/6855* (2017.08); *A61K 47/6859* (2017.08); *A61K 47/6889* (2017.08); *C07K 16/2863* (2013.01); *C07K 16/32* (2013.01); *C12Q 1/48* (2013.01)

(58) Field of Classification Search
CPC ............ A61K 47/6811; A61K 47/6859; A61K 47/6855; A61K 47/6851; A61K 47/6849; A61K 47/6817; A61K 47/6803; A61K 47/55; A61K 47/549; A61K 47/6889; A61K 47/65; A61K 47/50; A61K 48/00; A61K 39/395; A61K 31/70; C07K 16/2863; C07K 16/32; C12Q 1/48
See application file for complete search history.

(56) References Cited

U.S. PATENT DOCUMENTS

| 4,816,567 | A | 3/1989 | Cabilly et al. |
| 5,514,548 | A | 5/1996 | Krebber et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,591,669 | A | 1/1997 | Krimpenfort et al. |
| 5,635,483 | A | 6/1997 | Pettit et al. |
| 6,011,175 | A | 1/2000 | Sebti et al. |
| 8,865,875 | B2 | 10/2014 | Liu et al. |
| 9,669,107 | B2 * | 6/2017 | Kim ........................ C12Q 1/48 |
| 9,919,057 | B2 * | 3/2018 | Kim .................. A61K 47/6811 |
| 2003/0017149 | A1 | 1/2003 | Hoeffler et al. |
| 2003/0129191 | A1 | 7/2003 | Theodore et al. |
| 2004/0006215 | A1 | 1/2004 | Keler et al. |
| 2005/0201994 | A1 | 9/2005 | Korman et al. |
| 2005/0238649 | A1 | 10/2005 | Doronina et al. |
| 2005/0266008 | A1 | 12/2005 | Graziano et al. |
| 2006/0088522 | A1 | 4/2006 | Boghaert et al. |
| 2007/0122408 | A1 | 5/2007 | Barbas |
| 2007/0141084 | A1 | 6/2007 | Lee et al. |
| 2009/0069548 | A1 | 3/2009 | Poulter et al. |

(Continued)

FOREIGN PATENT DOCUMENTS

| CN | 102012425 A | 4/2011 |
| EP | 1391213 A1 | 2/2004 |

(Continued)

OTHER PUBLICATIONS

Rudikoff et al., PNAS 79: 1979-1983 (Year: 1982).*

(Continued)

*Primary Examiner* — Phuong Huynh
(74) *Attorney, Agent, or Firm* — Foley Hoag LLP

(57) ABSTRACT

The invention provides protein-active agent conjugates having an amino acid motif that can be recognized by an isoprenoid transferase. The invention also provides compositions containing the conjugates. The invention further provides methods for using the conjugates to deliver the active agent to a target cell, as well as methods for using the conjugates to treat a subject in need thereof (e.g., a subject in need of the active agent).

23 Claims, 25 Drawing Sheets

Specification includes a Sequence Listing.

(56) References Cited

U.S. PATENT DOCUMENTS

| | | |
|---|---|---|
| 2009/0081210 A1 | 3/2009 | Evans et al. |
| 2009/0105461 A1 | 4/2009 | Kunz et al. |
| 2010/0009872 A1 | 1/2010 | Eid et al. |
| 2010/0063114 A1 | 3/2010 | Tamanoi et al. |
| 2015/0105541 A1 | 4/2015 | Kim et al. |

FOREIGN PATENT DOCUMENTS

| | | |
|---|---|---|
| JP | 2009501800 A | 1/2009 |
| JP | 2010533495 A | 10/2010 |
| KR | 20140035393 A | 3/2014 |
| RU | 2385879 C2 | 4/2010 |
| WO | WO-1997/17852 A1 | 5/1997 |
| WO | WO-2005/070468 A2 | 8/2005 |
| WO | WO-2007/038637 A2 | 4/2007 |
| WO | WO-2007/048127 A2 | 4/2007 |
| WO | WO-2008/074004 A2 | 6/2008 |
| WO | WO-2009/026274 A1 | 2/2009 |
| WO | WO-2009/038685 A1 | 3/2009 |

OTHER PUBLICATIONS

Kussie et al., J. Immunol. 152: 146-152 (Year: 1994).*
Chen et al., EMBO J., 14: 2784-2794 (Year: 1995).*
Stancovski et al., PNAS, 88: 8691-8695, 1991 (Year: 1991).*
Jubala et al., Vet Pathol 42: 468-476 (Year: 2005).*
Dosio et al., Toxins 3: 848-883 (Year: 2011).*
Tanizawa et al., Journal of the National Cancer Institute 86(11); 836-842 (Year: 1994).*
Lloyd et al., Protein Engineering, Design & Selection 22:159-168 (Year: 2009).*
Edwards et al., J Mol Biol. 334(1): 103-118 (Year: 2003).*
Barbas III, B.F. et al., "In vitro evolution of a neutralizing human antibody to human immunodeficiency virus type 1 to enhance affinity and broaden strain cross-reactivity", Proc. Nat. Acad. Sci. USA, vol. 91, pp. 3809-3813 (Apr. 1994).
Beatty, K.E. et al., "Selective Dye-Labeling of Newly Synthesized Proteins in Bacterial Cells", J. Am. Chem. Soc., 127, pp. 14150-14151 (2005).
Beeram et al., A phase I study of trastuzumab-DM1 (T-DM1), a first-in-class HER2 antibody-drug conjugate (ADC), in patients (pts) with advanced HER2+ breast cancer (BC), J Clin Oncol, 26:1028 (2008).
Bock, V.D. et al., "Cu-Catalyzed Alkyne-Azide "Click" Cycloadditions from a Mechanistic and Synthetic Perspective", Eur. J. Org. Chem., pp. 51-68 (2006).
Boswell et al., "Impact of drug conjugation on pharmacokinetics and tissue distribution of anti-STEAP1 antibody-drug conjugates in rats," Bioconjugate Chem, 22:1994-2004 (2011).
Bowie, et al., "Deciphering the Message in Protein Sequences: Tolerance to Amino Acid Substitutions." Science 247, pp. 1306-1310 1990.
Brennan, M. et al., "Preparation of Bispecific Antibodies by Chemical Recombination of Monoclonal Immunoglobulin G1 Fragments", Science, vol. 229, No. 4708, pp. 81-83 (Jul. 5, 1985).
Brown et al., "Tolerance to Single, but Not Multiple, Amino Acid Replacements in Antibody VH, CDR2," J Immunol, 156(9): 3285-3291 (May 1996).
Burgess et al., "Possible Dissociation of the Heparin-Binding and Mitogenic Activities of Heparin-Binding (acidic fibroblast) Growth Factor-1 from its Receptor-Binding Activities by Site-Directed Mutagenesis of a Single Lysine Residue." Journal of Cell Biology 111, pp. 2129-2138, 1990.
Bynum, J. et al., "Development of Class-Switched, Affinity-Matured Monoclonal Antibodies Following a 7-Day Immunization Schedule", Hybridoma, vol. 18, No. 5, pp. 407-411 (Nov. 5, 1999).
Caldwell et al., "Consequences of altered isoprenylation targets on a-factor export and bioactivity," Proc Natl Acad Sci USA, 91:1275-9 (1994).

Casey, P.J. et al., "Protein Prenyltransferases", The Journal of Biological Chemistry, vol. 271, No. 10, pp. 5289-5292 (1996).
Casi et al., "Antibody-drug conjugates: Basic concepts, examples and future perspectives," J Control Release, 161: 422-428 (2012).
Casset et al., "A peptide mimetic of an anti-CD4 monoclonal antibody by rational design," Biochem Bioph Res Co, 307: 198-205 (2003).
Chamnongpol et al., "SH3 Domain Protein-Binding Arrays". Methods Mol Bioi. 2004; 264:183-9.
Chari, R.V.J., "Targeted Cancer Therapy: Conferring Specificity to Cytotoxic Drugs", Accounts of Chemical Research, vol. 41, No. 1, pp. 98-1 07 (Jan. 2008).
Clackson, T. et al., "Making antibody fragments using phage display libraries", Nature, vol. 352, pp. 624-628 (Aug. 15, 1991).
Colman, "A structural view of immune recognition by antibodies," Res Immunol, 145: 33-36 (1994).
Dongen et al., "Immune-PET: A Navigator in Monoclonal Antibody Development and Applications". The Oncologist 2007; 12:1379-1389.
Dubowchik, G.M. et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", Bioconjugate Chem., 13, pp. 855-869 (2002).
Duckworth, B.P. et al., "Selective Labeling of Proteins by Using Protein Farnesyltransferase", ChemBioChem, 8, pp. 98-1 05 (2007).
Dufner et al., "Harnessing phage and ribosome display for antibody optimisation," Trends Biotechnol, 24(11): 523-529 (2006).
Dursina, B. et al., "Identification and Specificity Profiling of Protein Prenyltransferase inhibitors Using New Fluorescent Phosphoisoprenoids", J. Am. Chem. Soc., 128, pp. 2822-2835 (2006).
Gelb et al., "Therapeutic intervention based on protein prenylation and associated modifications," Nat Chem Biol, 2(10):518-28 (2006).
Glomset et al., "Prenyl proteins in eukaryotic cells: a new type of membrane anchor," Trends Biochem Sci, 15(4):139-42 (1990).
Graversen et al., "Targeting the Hemoglobin Scavenger receptor CD163 in Macrophages Highly Increases the Anti-Inflammatory Potency of Dexamethasone," Mol Ther, 20(8): 1550-1558 (2012).
Greenspan et al., "Defining Epitopes: It's not as easy as it seems." Nature Biotechnology 7 pp. 936-937 1999.
Hamblett et al., "Effects of drug loading on the antitumor activity of a monoclonal antibody drug conjugate," Clin Cancer Res, 10:7063-70 (2004).
Hannoush, R.N. et al., "The chemical toolbox for monitoring protein fatty acylation and 1 prenylation", Nature Chemical Biology, vol. 6, pp. 498-506 (Jul. 2010).
Hartley, J.A. et al., "SG2285, a Novel C2-Aryi-Substituted Pyrrolobenzodiazepine Dimer Prodrug That Cross-links DNA and Exerts Highly Potent Antitumor Activity", Cancer Res., 70, 1 pp. 6849-6858 (2010).
Hartman et al., "Peptide specificity of protein prenyltransferases is determined mainly by reactivity rather than binding affinity," Biochem, 44:15314-24 (2005).
Hawkins, R.E. et al., "Selection of Phage Antibodies by Binding Affinity Mimicking Affinity Maturation", *J. Mol. Bioi.*, vol. 226, pp. 889-896 (1992).
Hinman, L.M. et al., "Preparation and Characterization of Monoclonal Antibody Conjugates of the Calicheamicins: A Novel and Potent Family of Antitumor Antibiotics", *Cancer Res.*, 53, pp. 3336-3342 (1993).
Hrycyna et al., "Modification of eukaryotic signaling proteins by c-terminal methylation reactions," Pharmacol Ther, 59(3):281-300 (1993).
Iha, R.K. et al., "Applications of Orthogonal "Click" Chemistries in the Synthesis of Functional Soft Materials", *Chem. Rev.*, 109, pp. 5620-5686 (2009).
International Search Report and Written Opinion for International Patent Application No. PCT/IB2012/001065 dated Jan. 31, 2013.
Jackson, J.R. et al., "In Vitro Antibody Maturation", The Journal of Immunology, vol. 154, pp. 3310-3319 (1995).

(56) References Cited

OTHER PUBLICATIONS

Jain et al, "Structure of human 6-glucuronidase reveals candidate lysosomal targeting and active-site motifs." Nat Struct Bioi. Apr. 1996; 3(4):375-81.

Jakobovits, A. et al., "Analysis of homozygous mutant chimeric mice: Deletion of the immunoglobulin heavy-chain joining region blocks B-cell development and antibody production", Proc. Nat/. Acad. Sci. USA, vol. 90, pp. 2551-2555 (Mar. 1993).

Jakobovits, A. et al., "Germ-line transmission and expression of a human-derived yeast artificial chromosome", Nature, vol. 362, pp. 255-258 (Mar. 18, 1993).

Jeffrey et al., "Development and properties of B-glucuronide linkers for monoclonal antibody-drug conjugates," Bioconjug Chem, 17:831-840 (2006).

Jeffrey et al., "Dipeptide-based highly potent doxorubicin antibody conjugates." Bioorg Med Chem. Lett. Jan. 15, 2006; 16(2):358-62.

Jeffrey et al., "Expanded utility of the B-glucuronide linker: ADCs that deliver phenolic cytotoxic agents," Med Chem Lett, 1(6):277-80 (2010).

Jones et al., "Critically assessing the state-of-the-art in protein structure prediction," Pharmacogenomics Journal, 1: 126-134 (2001).

Kerr, D.E., et al., "Listeriolysin O Potentiates Immunotoxin and Bleomycin Cytotoxicity," Bioconjugate Chem, 8(6):781-4 (1997).

Khosravi-Far et al., "Ras (CXXX) and Rab (CC/CXC) prenylation signal sequences are unique and functionally distinct," J Biol Chem, 267(34):24363-8 (1992).

Kilpatrick, K.E. et al., "Rapid Development of Affinity Matured Monoclonal Antibodies Using RIMMS", Hybridoma, vol. 16, No. 4, pp. 381-389 (1997).

Kohler, G. et al., "Continuous cultures of fused cells secreting antibody of predefined specificity," Nature, 256:495-7 (1975).

Kolb et al., "The growing impact of click chemistry on drug discovery," Drug Discov Today, 8(24):1124-37 (2003).

Kolb, H. C., et al., "Click Chemistry: Diverse Chemical Function from a Few Good Reactions", Angew. Chem. Int. Ed., 40, pp. 2004-2021 (2001).

Korean Intellectual Property Office, Notification of Reason for Refusal, dated Nov. 20, 2015 for corresponding application No. KR 10-2015-0073161.

Labadie et a., "Farnesyl Diphosphate Analogues with w-Bioorthogonal Azide and Alkyne Functional Groups for PFTase-Catalyzed Ligation Reactions." J Org Chem. Nov. 23, 2007; 72(24): 9291-9297.

Lane, K.T. et al., "Structural biology of protein farnesyltransferase and geranylgeranyltransferase type I", Journal Lipid Research, 47, pp. 681-699 (2006).

Lazar, et al., "Transforming Growth Factor Alpha: Mutation of Aspartic Acid 47 and Leucine 48 Results in Different Biological Activities." Molecular Cellular Biology 8, pp. 1247-1252, 1988.

Lee et al., "Enzymatic prenylation and oxime ligation for the synthesis of stable and homogeneous protein-drug conjugates for targeted therapy," Angew Chem Int Ed, 54:1-6 (2015).

Levary, D.A. et al., "Protein-Protein Fusion Catalyzed by Sortase A," PLoS One, 6(4):e18342 (2011).

Lewis et al. "Targeting HER2-Positive Breast Cancer with Trastuzumab-DM1, an Antibody-Cytotoxic Drug Conjugate". Cancer Res 2008; 68: (22). Nov. 15, 2008.

MacCallum et al., "Antibody-antigen Interactions: Contact Analysis and Binding Site Topography," J Mol Biol, 262: 732-745 (1996).

Marks, J.D. et al., "By-passing Immunization Human Antibodies from V-gene Libraries Displayed on Phage", J. Mol. Biol., vol. 222, pp. 581-597 (1991).

Maurer-Stroh et al., "Refinement and prediction of protein prenylation motifs," Genome Biol, 6:R55 (2005).

McCafferty, J. et al., "Phage antibodies: filamentous phage displaying antibody variable domains", Nature, vol. 348, pp. 552-554 (Dec. 6, 1990).

Meldal, M. et al., "Cu-Catalyzed Azide-Alkyne Cycloaddition", Chem. Rev., 108, pp. 2952-3015. 2008.

Miyazaki, K. et al., "Synthesis and Antitumor Activity of Novel Dolastatin 10 Analogs", Chem. Pharm. Bull., 43(1 0) pp. 1706-1718 (1995).

Moores, Sheri L, et. al., "Sequence Dependence of Protein Isoprenylation," The Journal of Biological Chemistry 266(22): 14603-14610, 1991.

Morimoto, K. et al., "Single-step purification of F(ab')2 fragments of mouse monoclonal antibodies (immunoglobulins G1) by hydrophobic interaction high performance liquid chromatography using TSKgel Phenyi-5PW", Journal of Biochemical and Biophysical Methods, vol. 24, pp. 107-117 (1992).

Nguyen et al. "Analysis of the eukaryotic prenylome by isoprenoid affinity tagging". Nat Chem Biol. Apr. 2009; 5(4):227-35.

Nguyen, U.T. et al., "Exploiting the Substrate Tolerance of Farnesyltransferase for Site-Selective Protein Derivatization", ChemBioChem, 8, pp. 408-423 (2007).

Notice of Allowance for U.S. Appl. No. 14/517,616 dated Apr. 11, 2017.

Paul, Fundamental Immunology, 3rd Edition, Raven Press, New York, Chapter 8, pp. 292-295, 1993.

Petersen et al., "The human immune response to KS1/4-desacetylvinblastine (LY256787) and KS1/4-desacetylvinblastine hydrazide (LY203728) in single and multiple dose clinical studies," Cancer Res, 51:2286-90 (1991).

Phillips et al., "Targeting HER2-Positive Breast Cancer with Trastuzumab-DM1, an Antibody-Cytotoxic Drug Conjugate," Cancer Res, 68: 9280-9290 (Nov. 15, 2008).

Pietersz et al., "Antibody-targeted drugs for the therapy of cancer," J Drug Targeting, 2:183-215 (1994).

Rashidian et al., "Chemoenzymatic labeling of proteins: Techniques and approaches," Bioconj Chem, 24(8):1277-94 (2013).

Rashidian, Mohammad et al., "Selective Labeling of Polypeptides Using Protein Farnesyltransferase via Rapid Oxime Ligation," Chem Communication 46: 8998-9000, 2010.

Reiss et al. "Sequence requirement for peptide recognition by rat brain p21 ras protein farnesyltransferase." Proc Nat'l Acad Sci USA. Feb. 1, 1991;88(3):732-6.

Rodionov, V. O. et al., "Mechanism of the Ligand-Free Cu1-Catalyzed Azide-Alkyne Cycloaddition Reaction", Angew. Chem. Int. Ed., 44, pp. 2210-2215 (2005).

Rose, Matthew W., et. al., "Enzymatic Incorporation of Orthogonally Reactive Prenylazide Groups into Peptides Using Geranylazide Diphosphate Via Protein Farnesyltransferase: Implications for Selective Protein Labeling," Bipolymers ;80(2-3): 164-171, 2005.

Rowinsky et al. "Ras Protein Farnesyltransferase: A Strategic Target for Anticancer Therapeutic Development." J Clin Oncol. Nov. 1999;17(11):3631-52.

Rudikoff et al., "Single amino acid substitution altering antigen-binding specificity," Proc Natl Acad Sci USA, 79(6): 1979-1983 (Mar. 1982).

Sanderson et al., "In vivo drug-linker stability of an anti-CD30 dipeptide-linked auristatin immunoconjugate," Clin Cancer Res, 11:843-852 (2005).

Schier, R. et al., "Identification of functional and structural amino-acid residues by parsimonious mutagenesis", Gene, vol. 169, pp. 147-155 (1996).

Skolnick et al., "From genes to protein structure and function: novel applications of computational approaches in the genomic era," Trends in Biotechnology, 18: 34-39 (2000).

Supplementary European Search Report for EP 12 78 2658 dated Feb. 13, 2015.

Tanizawa et al., "Comparison of topoisomerase I inhibition, DNA damage, and cytotoxicity of camptothecin derivatives presently in clinical trials," J Natl Cancer I, 86(11):836-42 (1994).

Taylor et al., "Structure of mammalian protein geranylgeranyltransferase type-I," EMBO J, 22(22):5963-74 (2003).

Thorek, D.L.J. et al., "Comparative Analysis of Nanoparticle-Antibody Conjugations: Carbodiimide versus Click Chemistry," Molecular Imaging, 8(4):221-229 (2009).

Tosatto et al., "Large-Scale Prediction of Protein Structure and Function from Sequence," Current Pharmaceutical Design, 12: 2067-2086 (2006).

(56) References Cited

OTHER PUBLICATIONS

Wang et al., "Structural characterization of the maytansinoid-monoclonal antibody immunoconjugate, huN901-DM1, by mass spectrometry," Protein Sci, 14:2436-46 (2005).
Wang, Q. et al., "Bioconjugation by copper(I)-catalyzed azide-alkyne [3+2] cycloaddition," J Am Chem Soc, 125:3192-3 (2003).
Waterhouse, P. et al., "Combinatorial infection and in vivo recombination: a strategy for making large phage antibody repertoires", Nucleic Acids Research, vol. 21, No. 9, pp. 2265-2266 (1993).
Winter-Vann, A.M. et al., "Post-prenylation-processing enzymes as new targets in oncogenesis," Nature Reviews, 5:405-12 (2005).
Wollack, J.W. et al., "A Minimalist Substrate for Enzymatic Peptide and Protein Conjugation", ChemBioChem, 10, pp. 2934-2943 (2009).
Wright et al., "Thematic review series: lipid postranslational modifications. CAAX modification and membrane targeting of Ras." J Lipid Res, 47(5):883-91 (2006).
Wring, S.A. et al., "Shorter development of immunoassay for drugs: application of the novel RIMMS technique enables rapid production of monoclonal antibodies to ranitidine", Journal of Pharmaceutical and Biomedical Analysis, vol. 19, pp. 695-707 ( 1999).
Wu et al., "Humanization of a Murine Monoclonal Antibody by Simultaneous Optimization of Framework and CDR Residues," J Mol Biol, 294: 151-162 (1999).
Yelton, D.E. et al., "Affinity Maturation of the BR96 Anti-Carcinoma Antibody by Codon-Based Mutagenesis", The Journal of Immunology, vol. 155, pp. 1994-2004 (1995).
Yu et al., "Interaction between Bevacizumab and Murine VEGF-A: A Reassessment," Invest Ophth Vis Sci, 49(2): 522-527 (Feb. 2008).
Zhang et al., "Protein prenylation: Molecular mechanisms and functional consequences," Ann Rev Biochem, 65:241-69 (1996).
Zhu et al., "Determination of protein isoprenylation in vitro and in vivo," Methods Cell Biol, 50:31-9 (1995).
Rabuka, "Chemoenzymatic Methods for Site-Specific Protein Modification," Curr Opin Chem Biol, 14(6): 790-796 (2010).
Simmons et al., "Expression of full-length immunoglobulins in *Escherichia coli*: rapid and efficient production of aglycosylated antibodies," Journal of Immunological Methods, 263(1-2):133-147 (2002).

\* cited by examiner

FIG. 1

Heavy chain

```
         10          20          30          40          50          60
EVQLVESGGG  LVQPGGSLRL  SCAASGFNIK  DTYIHWVRQA  PGKGLEWVAR  IYPTNGYTRY 70          80          90         100         110         120
ADSVKGRFTI  SADTSKNTAY  LQMNSLRAED  TAVYYCSRWG  GDGFYAMDYW  GQGTLVTVSS 130         140         150         160         170         180
ASTKGPSVFP  LAPSSKSTSG  GTAALGCLVK  DYFPEPVTVS  WNSGALTSGV  HTFPAVLQSS 190         200         210         220         230         240
GLYSLSSVVT  VPSSSLGTQT  YICNVNHKPS  NTKVDKRVEP  KSCDKTHTCP  PCPAPELLGG 250         260         270         280         290         300
PSVFLFPPKP  KDTLMISRTP  EVTCVVVDVS  HEDPEVKFNW  YVDGVEVHNA  KTKPREEQYN 310         320         330         340         350         360
STYRVVSVLT  VLHQDWLNGK  EYKCKVSNKA  LPAPIEKTIS  KAKGQPREPQ  VYTLPPSRDE 370         380         390         400         410         420
LTKNQVSLTC  LVKGFYPSDI  AVEWESNGQP  ENNYKTTPPV  LDSDGSFFLY  SKLTVDKSRW 430         440         450
QQGNVFSCSV  MHEALHNHYT  QKSLSLSPGK  GCVIM
```

Light chain

```
         10          20          30          40          50          60
DIQMTQSPSS  LSASVGDRVT  ITCRASQDVN  TAVAWYQQKP  GKAPKLLIYS  ASFLYSGVPS 70          80          90         100         110         120
RFSGSRSGTD  FTLTISSLQP  EDFATYYCQQ  HYTTPPTFGQ  GTKVEIKRSV  AAPSVFIFPP 130         140         150         160         170         180
SDEQLKSGTA  SVVCLLNNFY  PREAKVQWKV  DNALQSGNSQ  ESVTEQDSKD  STYSLSSTLT 190         200         210
LSKADYEKHK  VYACEVTHQG  LSSPVTKSFN  RGEC
```

FIG. 2

Heavy chain

```
         10         20         30         40         50         60
EVQLVESGGG LVQPGGSLRL SCAASGFNIK DTYIHWVRQA PGKGLEWVAR IYPTNGYTRY 70         80         90        100        110        120
ADSVKGRFTI SADTSKNTAY LQMNSLRAED TAVYYCSRWG GDGFYAMDYW GQGTLVTVSS 130        140        150        160        170        180
ASTKGPSVFP LAPSSKSTSG GTAALGCLVK DYFPEPVTVS WNSGALTSGV HTFPAVLQSS 190        200        210        220        230        240
GLYSLSSVVT VPSSSLGTQT YICNVNHKPS NTKVDKRVEP KSCDKTHTCP PCPAPELLGG 250        260        270        280        290        300
PSVFLFPPKP KDTLMISRTP EVTCVVVDVS HEDPEVKFNW YVDGVEVHNA KTKPREEQYN 310        320        330        340        350        360
STYRVVSVLT VLHQDWLNGK EYKCKVSNKA LPAPIEKTIS KAKGQPREPQ VYTLPPSRDE 370        380        390        400        410        420
LTKNQVSLTC LVKGFYPSDI AVEWESNGQP ENNYKTTPPV LDSDGSFFLY SKLTVDKSRW 430        440        450
QQGNVFSCSV MHEALHNHYT QKSLSLSPGK
```

Light chain

```
         10         20         30         40         50         60
DIQMTQSPSS LSASVGDRVT ITCRASQDVN TAVAWYQQKP GKAPKLLIYS ASFLYSGVPS 70         80         90        100        110        120
RFSGSRSGTD FTLTISSLQP EDFATYYCQQ HYTTPPTFGQ GTKVEIKRSV AAPSVFIFPP 130        140        150        160        170        180
SDEQLKSGTA SVVCLLNNFY PREAKVQWKV DNALQSGNSQ ESVTEQDSKD STYSLSSTLT 190        200        210
LSKADYEKHK VYACEVTHQG LSSPVTKSFN RGECGCVIM
```

FIG. 3

Heavy chain

```
         10         20         30         40         50         60
EVQLVESGGG LVQPGGSLRL SCAASGFNIK DTYIHWVRQA PGKGLEWVAR IYPTNGYTRY 70         80         90        100        110        120
ADSVKGRFTI SADTSKNTAY LQMNSLRAED TAVYYCSRWG GDGFYAMDYW GQGTLVTVSS 130        140        150        160        170        180
ASTKGPSVFP LAPSSKSTSG GTAALGCLVK DYFPEPVTVS WNSGALTSGV HTFPAVLQSS 190        200        210        220        230        240
GLYSLSSVVT VPSSSLGTQT YICNVNHKPS NTKVDKRVEP KSCDKTHTCP PCPAPELLGG 250        260        270        280        290        300
PSVFLFPPKP KDTLMISRTP EVTCVVVDVS HEDPEVKFNW YVDGVEVHNA KTKPREEQYN 310        320        330        340        350        360
STYRVVSVLT VLHQDWLNGK EYKCKVSNKA LPAPIEKTIS KAKGQPREPQ VYTLPPSRDE 370        380        390        400        410        420
LTKNQVSLTC LVKGFYPSDI AVEWESNGQP ENNYKTTPPV LDSDGSFFLY SKLTVDKSRW 430        440        450
QQGNVFSCSV MHEALHNHYT QKSLSLSPGK GGGGGCVIM
```

Light chain

```
         10         20         30         40         50         60
DIQMTQSPSS LSASVGDRVT ITCRASQDVN TAVAWYQQKP GKAPKLLIYS ASFLYSGVPS 70         80         90        100        110        120
RFSGSRSGTD FTLTISSLQP EDFATYYCQQ HYTTPPTFGQ GTKVEIKRSV AAPSVFIFPP 130        140        150        160        170        180
SDEQLKSGTA SVVCLLNNFY PREAKVQWKV DNALQSGNSQ ESVTEQDSKD STYSLSSTLT 190        200        210
LSKADYEKHK VYACEVTHQG LSSPVTKSFN RGEC
```

FIG. 4

Heavy chain

```
         10         20         30         40         50         60
EVQLVESGGG LVQPGGSLRL SCAASGFNIK DTYIHWVRQA PGKGLEWVAR IYPTNGYTRY 70         80         90        100        110        120
ADSVKGRFTI SADTSKNTAY LQMNSLRAED TAVYYCSRWG GDGFYAMDYW GQGTLVTVSS 130        140        150        160        170        180
ASTKGPSVFP LAPSSKSTSG GTAALGCLVK DYFPEPVTVS WNSGALTSGV HTFPAVLQSS 190        200        210        220        230        240
GLYSLSSVVT VPSSSLGTQT YICNVNHKPS NTKVDKRVEP KSCDKTHTCP PCPAPELLGG 250        260        270        280        290        300
PSVFLFPPKP KDTLMISRTP EVTCVVVDVS HEDPEVKFNW YVDGVEVHNA KTKPREEQYN 310        320        330        340        350        360
STYRVVSVLT VLHQDWLNGK EYKCKVSNKA LPAPIEKTIS KAKGQPREPQ VYTLPPSRDE 370        380        390        400        410        420
LTKNQVSLTC LVKGFYPSDI AVEWESNGQP ENNYKTTPPV LDSDGSFFLY SKLTVDKSRW 430        440        450
QQGNVFSCSV MHEALHNHYT QKSLSLSPGK
```

Light chain

```
         10         20         30         40         50         60
DIQMTQSPSS LSASVGDRVT ITCRASQDVN TAVAWYQQKP GKAPKLLIYS ASFLYSGVPS 70         80         90        100        110        120
RFSGSRSGTD FTLTISSLQP EDFATYYCQQ HYTTPPTFGQ GTKVEIKRSV AAPSVFIFPP 130        140        150        160        170        180
SDEQLKSGTA SVVCLLNNFY PREAKVQWKV DNALQSGNSQ ESVTEQDSKD STYSLSSTLT 190        200        210        220
LSKADYEKHK VYACEVTHQG LSSPVTKSFN RGECGGGGGC VIM
```

FIG. 5

Heavy chain

```
         10         20         30         40         50         60
EVQLVESGGG LVQPGGSLRL SCAASGFNIK DTYIHWVRQA PGKGLEWVAR IYPTNGYTRY 70         80         90        100        110        120
ADSVKGRFTI SADTSKNTAY LQMNSLRAED TAVYYCSRWG GDGFYAMDYW GQGTLVTVSS 130        140        150        160        170        180
ASTKGPSVFP LAPSSKSTSG GTAALGCLVK DYFPEPVTVS WNSGALTSGV HTFPAVLQSS 190        200        210        220        230        240
GLYSLSSVVT VPSSSLGTQT YICNVNHKPS NTKVDKRVEP KSCDKTHTCP PCPAPELLGG 250        260        270        280        290        300
PSVFLFPPKP KDTLMISRTP EVTCVVVDVS HEDPEVKFNW YVDGVEVHNA KTKPREEQYN 310        320        330        340        350        360
STYRVVSVLT VLHQDWLNGK EYKCKVSNKA LPAPIEKTIS KAKGQPREPQ VYTLPPSRDE 370        380        390        400        410        420
LTKNQVSLTC LVKGFYPSDI AVEWESNGQP ENNYKTTPPV LDSDGSFFLY SKLTVDKSRW 430        440        450        460
QQGNVFSCSV MHEALHNHYT QKSLSLSPGK GGGGGGGCVI M
```

Light chain

```
         10         20         30         40         50         60
DIQMTQSPSS LSASVGDRVT ITCRASQDVN TAVAWYQQKP GKAPKLLIYS ASFLYSGVPS 70         80         90        100        110        120
RFSGSRSGTD FTLTISSLQP EDFATYYCQQ HYTTPPTFGQ GTKVEIKRSV AAPSVFIFPP 130        140        150        160        170        180
SDEQLKSGTA SVVCLLNNFY PREAKVQWKV DNALQSGNSQ ESVTEQDSKD STYSLSSTLT 190        200        210
LSKADYEKHK VYACEVTHQG LSSPVTKSFN RGEC
```

FIG. 6

Heavy chain

```
         10         20         30         40         50         60
EVQLVESGGG LVQPGGSLRL SCAASGFNIK DTYIHWVRQA PGKGLEWVAR IYPTNGYTRY 70         80         90        100        110        120
ADSVKGRFTI SADTSKNTAY LQMNSLRAED TAVYYCSRWG GDGFYAMDYW GQGTLVTVSS 130        140        150        160        170        180
ASTKGPSVFP LAPSSKSTSG GTAALGCLVK DYFPEPVTVS WNSGALTSGV HTFPAVLQSS 190        200        210        220        230        240
GLYSLSSVVT VPSSSLGTQT YICNVNHKPS NTKVDKRVEP KSCDKTHTCP PCPAPELLGG 250        260        270        280        290        300
PSVFLFPPKP KDTLMISRTP EVTCVVVDVS HEDPEVKFNW YVDGVEVHNA KTKPREEQYN 310        320        330        340        350        360
STYRVVSVLT VLHQDWLNGK EYKCKVSNKA LPAPIEKTIS KAKGQPREPQ VYTLPPSRDE 370        380        390        400        410        420
LTKNQVSLTC LVKGFYPSDI AVEWESNGQP ENNYKTTPPV LDSDGSFFLY SKLTVDKSRW 430        440        450
QQGNVFSCSV MHEALHNHYT QKSLSLSPGK
```

Light chain

```
         10         20         30         40         50         60
DIQMTQSPSS LSASVGDRVT ITCRASQDVN TAVAWYQQKP GKAPKLLIYS ASFLYSGVPS 70         80         90        100        110        120
RFSGSRSGTD FTLTISSLQP EDFATYYCQQ HYTTPPTFGQ GTKVEIKRSV AAPSVFIFPP 130        140        150        160        170        180
SDEQLKSGTA SVVCLLNNFY PREAKVQWKV DNALQSGNSQ ESVTEQDSKD STYSLSSTLT 190        200        210        220
LSKADYEKHK VYACEVTHQG LSSPVTKSFN RGECGGGGGG GCVIM
```

FIG. 7

Heavy chain

```
        10         20         30         40         50         60
EVQLVESGGG LVQPGGSLRL SCAASGFNIK DTYIHWVRQA PGKGLEWVAR IYPTNGYTRY 70         80         90        100        110        120
ADSVKGRFTI SADTSKNTAY LQMNSLRAED TAVYYCSRWG GDGFYAMDYW GQGTLVTVSS 130        140        150        160        170        180
ASTKGPSVFP LAPSSKSTSG GTAALGCLVK DYFPEPVTVS WNSGALTSGV HTFPAVLQSS 190        200        210        220        230        240
GLYSLSSVVT VPSSSLGTQT YICNVNHKPS NTKVDKRVEP KSCDKTHTCP PCPAPELLGG 250        260        270        280        290        300
PSVFLFPPKP KDTLMISRTP EVTCVVVDVS HEDPEVKFNW YVDGVEVHNA KTKPREEQYN 310        320        330        340        350        360
STYRVVSVLT VLHQDWLNGK EYKCKVSNKA LPAPIEKTIS KAKGQPREPQ VYTLPPSRDE 370        380        390        400        410        420
LTKNQVSLTC LVKGFYPSDI AVEWESNGQP ENNYKTTPPV LDSDGSFFLY SKLTVDKSRW 430        440        450        460
QQGNVFSCSV MHEALHNHYT QKSLSLSPGK GGGGGGGGGG CVIM
```

Light chain

```
        10         20         30         40         50         60
DIQMTQSPSS LSASVGDRVT ITCRASQDVN TAVAWYQQKP GKAPKLLIYS ASFLYSGVPS 70         80         90        100        110        120
RFSGSRSGTD FTLTISSLQP EDFATYYCQQ HYTTPPTFGQ GTKVEIKRSV AAPSVFIFPP 130        140        150        160        170        180
SDEQLKSGTA SVVCLLNNFY PREAKVQWKV DNALQSGNSQ ESVTEQDSKD STYSLSSTLT 190        200        210
LSKADYEKHK VYACEVTHQG LSSPVTKSFN RGEC
```

FIG. 8

Heavy chain

```
         10         20         30         40         50         60
EVQLVESGGG LVQPGGSLRL SCAASGFNIK DTYIHWVRQA PGKGLEWVAR IYPTNGYTRY 70         80         90        100        110        120
ADSVKGRFTI SADTSKNTAY LQMNSLRAED TAVYYCSRWG GDGFYAMDYW GQGTLVTVSS 130        140        150        160        170        180
ASTKGPSVFP LAPSSKSTSG GTAALGCLVK DYFPEPVTVS WNSGALTSGV HTFPAVLQSS 190        200        210        220        230        240
GLYSLSSVVT VPSSSLGTQT YICNVNHKPS NTKVDKRVEP KSCDKTHTCP PCPAPELLGG 250        260        270        280        290        300
PSVFLFPPKP KDTLMISRTP EVTCVVVDVS HEDPEVKFNW YVDGVEVHNA KTKPREEQYN 310        320        330        340        350        360
STYRVVSVLT VLHQDWLNGK EYKCKVSNKA LPAPIEKTIS KAKGQPREPQ VYTLPPSRDE 370        380        390        400        410        420
LTKNQVSLTC LVKGFYPSDI AVEWESNGQP ENNYKTTPPV LDSDGSFFLY SKLTVDKSRW 430        440        450
QQGNVFSCSV MHEALHNHYT QKSLSLSPGK
```

Light chain

```
         10         20         30         40         50         60
DIQMTQSPSS LSASVGDRVT ITCRASQDVN TAVAWYQQKP GKAPKLLIYS ASFLYSGVPS 70         80         90        100        110        120
RFSGSRSGTD FTLTISSLQP EDFATYYCQQ HYTTPPTFGQ GTKVEIKRSV AAPSVFIFPP 130        140        150        160        170        180
SDEQLKSGTA SVVCLLNNFY PREAKVQWKV DNALQSGNSQ ESVTEQDSKD STYSLSSTLT 190        200        210        220
LSKADYEKHK VYACEVTHQG LSSPVTKSFN RGECGGGGGG GGGGCVIM
```

FIG. 9

Heavy chain

```
         10         20         30         40         50         60
EVQLVESGGG LVQPGGSLRL SCAASGFNIK DTYIHWVRQA PGKGLEWVAR IYPTNGYTRY 70         80         90        100        110        120
ADSVKGRFTI SADTSKNTAY LQMNSLRAED TAVYYCSRWG GDGFYAMDYW GQGTLVTVSS 130        140        150        160        170        180
ASTKGPSVFP LAPSSKSTSG GTAALGCLVK DYFPEPVTVS WNSGALTSGV HTFPAVLQSS 190        200        210        220        230        240
GLYSLSSVVT VPSSSLGTQT YICNVNHKPS NTKVDKRVEP KSCDKTHTCP PCPAPELLGG 250        260        270        280        290        300
PSVFLFPPKP KDTLMISRTP EVTCVVVDVS HEDPEVKFNW YVDGVEVHNA KTKPREEQYN 310        320        330        340        350        360
STYRVVSVLT VLHQDWLNGK EYKCKVSNKA LPAPIEKTIS KAKGQPREPQ VYTLPPSRDE 370        380        390        400        410        420
LTKNQVSLTC LVKGFYPSDI AVEWESNGQP ENNYKTTPPV LDSDGSFFLY SKLTVDKSRW 430        440        450        460
QQGNVFSCSV MHEALHNHYT QKSLSLSPGK GGGGGGGGGG CVLL
```

Light chain

```
         10         20         30         40         50         60
DIQMTQSPSS LSASVGDRVT ITCRASQDVN TAVAWYQQKP GKAPKLLIYS ASFLYSGVPS 70         80         90        100        110        120
RFSGSRSGTD FTLTISSLQP EDFATYYCQQ HYTTPPTFGQ GTKVEIKRSV AAPSVFIFPP 130        140        150        160        170        180
SDEQLKSGTA SVVCLLNNFY PREAKVQWKV DNALQSGNSQ ESVTEQDSKD STYSLSSTLT 190        200        210
LSKADYEKHK VYACEVTHQG LSSPVTKSFN RGEC
```

FIG. 10

Heavy chain

```
         10         20         30         40         50         60
EVQLVESGGG LVQPGGSLRL SCAASGFNIK DTYIHWVRQA PGKGLEWVAR IYPTNGYTRY 70         80         90        100        110        120
ADSVKGRFTI SADTSKNTAY LQMNSLRAED TAVYYCSRWG GDGFYAMDYW GQGTLVTVSS 130        140        150        160        170        180
ASTKGPSVFP LAPSSKSTSG GTAALGCLVK DYFPEPVTVS WNSGALTSGV HTFPAVLQSS 190        200        210        220        230        240
GLYSLSSVVT VPSSSLGTQT YICNVNHKPS NTKVDKRVEP KSCDKTHTCP PCPAPELLGG 250        260        270        280        290        300
PSVFLFPPKP KDTLMISRTP EVTCVVVDVS HEDPEVKFNW YVDGVEVHNA KTKPREEQYN 310        320        330        340        350        360
STYRVVSVLT VLHQDWLNGK EYKCKVSNKA LPAPIEKTIS KAKGQPREPQ VYTLPPSRDE 370        380        390        400        410        420
LTKNQVSLTC LVKGFYPSDI AVEWESNGQP ENNYKTTPPV LDSDGSFFLY SKLTVDKSRW 430        440        450
QQGNVFSCSV MHEALHNHYT QKSLSLSPGK
```

Light chain

```
         10         20         30         40         50         60
DIQMTQSPSS LSASVGDRVT ITCRASQDVN TAVAWYQQKP GKAPKLLIYS ASFLYSGVPS 70         80         90        100        110        120
RFSGSRSGTD FTLTISSLQP EDFATYYCQQ HYTTPPTFGQ GTKVEIKRSV AAPSVFIFPP 130        140        150        160        170        180
SDEQLKSGTA SVVCLLNNFY PREAKVQWKV DNALQSGNSQ ESVTEQDSKD STYSLSSTLT 190        200        210        220
LSKADYEKHK VYACEVTHQG LSSPVTKSFN RGECGGGGGG GGGGCVLL
```

FIG. 11
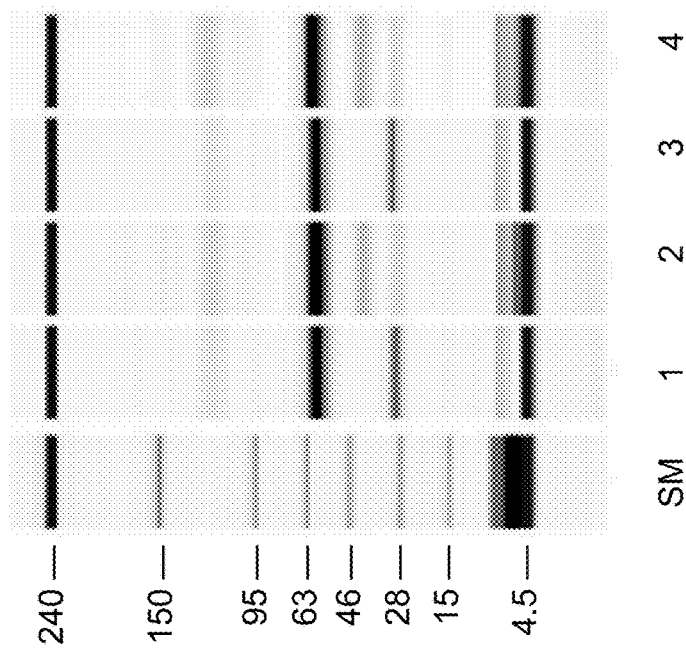
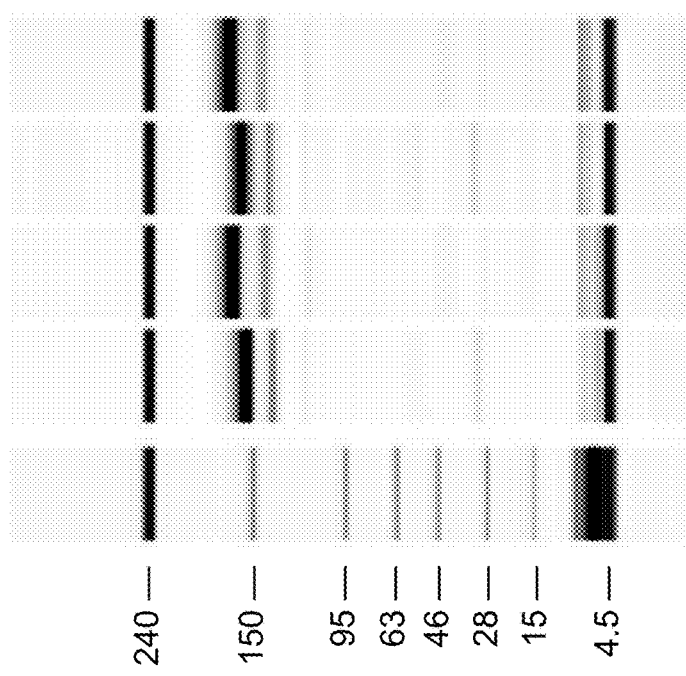
1: Anti cMET-LC-G$_7$CVIM
2: Anti cMET-HC-G$_7$CVIM
3: Anti cMET-LC-G$_{10}$CVIM
4: Anti cMET-HC-G$_{10}$CVIM 1: Herceptin-HC-GCVIM
2: Herceptin-HC-G$_7$CVIM
3: Herceptin-HC-G$_{10}$CVIM 1 : Herceptin-LC-GCVIM
2 : Herceptin-LC-$G_5$CVIM
3 : Herceptin-LC-$G_7$CVIM
4 : Herceptin-LC-$G_{10}$CVIM 1 : Anti cMET-HC-$G_7$CVIM
2 : Anti cMET-HC-$G_{10}$CVIM 1 : Herceptin-LC-$G_7$CVIM
2 : Herceptin-LC-$G_{10}$CVIM
3 : Anti cMET-LC-$G_7$CVIM
4 : Anti cMET-LC-$G_{10}$CVIM 1 : Herceptin-LC-$G_7$CVIM (positive control)
2 : Herceptin-HC-$G_{10}$CVLL
3 : Herceptin-LC-$G_{10}$CVLL
4 : Herceptin-HC-$G_{10}$CVLL
4 : Herceptin-LC-$G_{10}$CVLL

FIG. 17

| Sample | Theoretical Mass (Dalton) | | | Experimental Mass (Dalton) | | | Delta mass (Dalton) |
|---|---|---|---|---|---|---|---|
| | HC | LC, naked | LC, prenylated | HC | LC, naked | LC, prenylated | |
| Herceptin-LC-G-CVIM | 49,152* | 24,275 | - | 49,156* | 24,274 | - | |
| Prenylated Herceptin-LC-G-CVIM | 50,597** | 24,275 | 24,480 | 50,600** | - | 24,479 | 205 |

\* PNGase F treated
\*\* PNGase F non-treated

FIG. 18

| Sample | Theoretical Mass(Dalton) | | | Mass(Dalton) | | | Delta mass (Dalton) |
|---|---|---|---|---|---|---|---|
| | HC | LC, naked | LC, prenylated | HC | LC, naked | LC, prenylated | |
| Herceptin-LC-G₁₃CVIM | 49,152* | 24,446 | - | 49,156* | 24,445 | - | - |
| Prenylated Herceptin-LC-G₁₃CVIM | 50,596** | 24,446 | 24,651 | 50,601** | - | 24,651 | 206 |

* PNGase F treated
** PNGase F non-treated

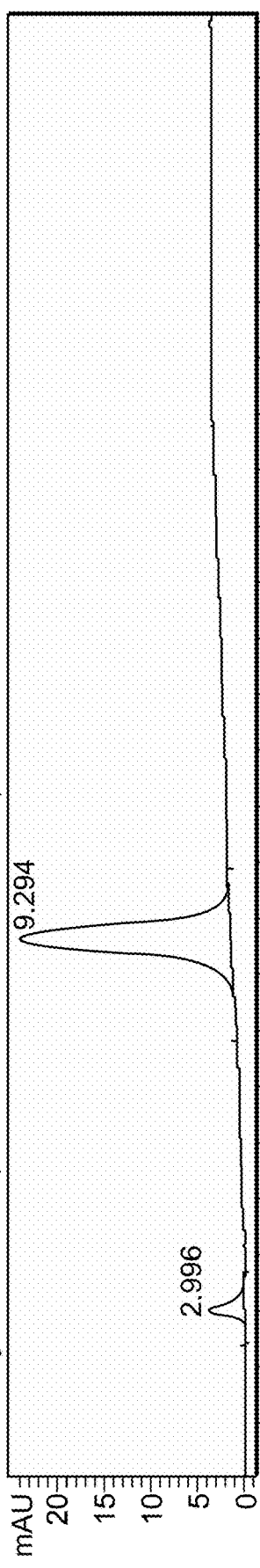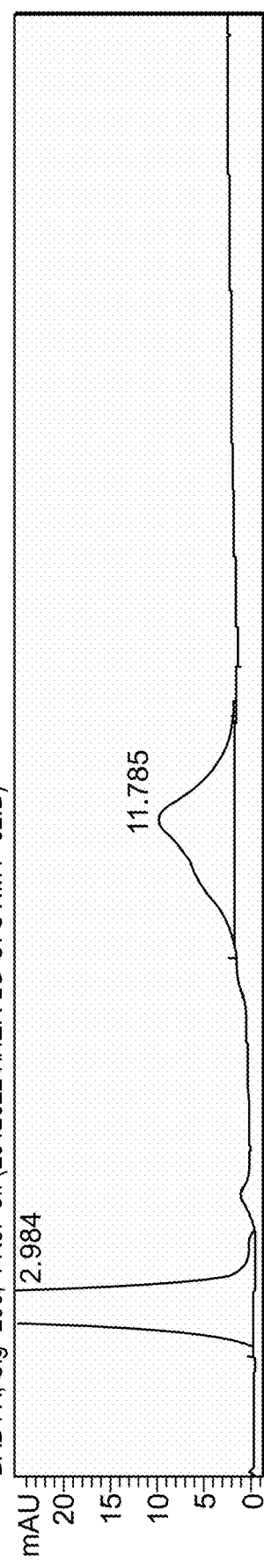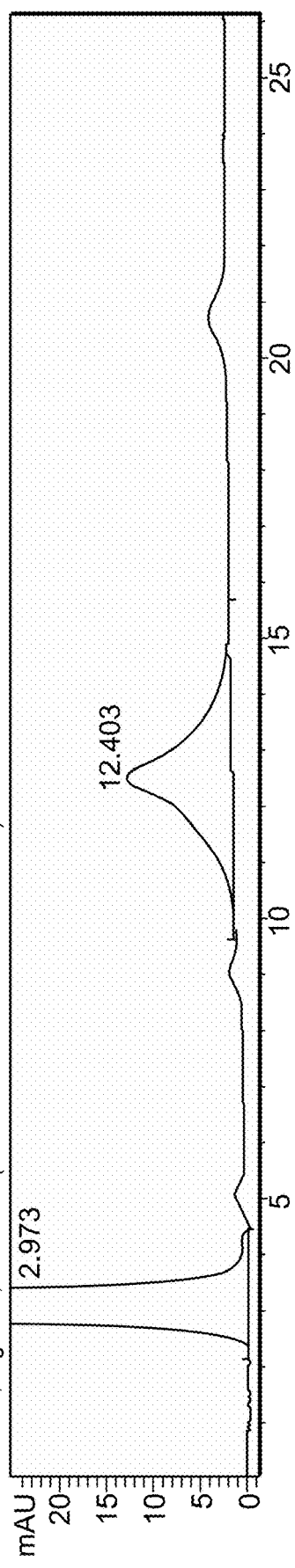
FIG. 20

| Cmpds | IC$_{50}$(μg/mL) | |
|---|---|---|
| | MCF-7 | SK-BR-3 |
| Herceptin-LG-G$_7$CVIM | >10 | >10 |
| LCB14-0102 (Herceptin-LG-G$_7$CVIM-VC-MMAF-Ome) | 4.38 | 0.15 |

FIG. 25
1) Val-Cit based drug linker
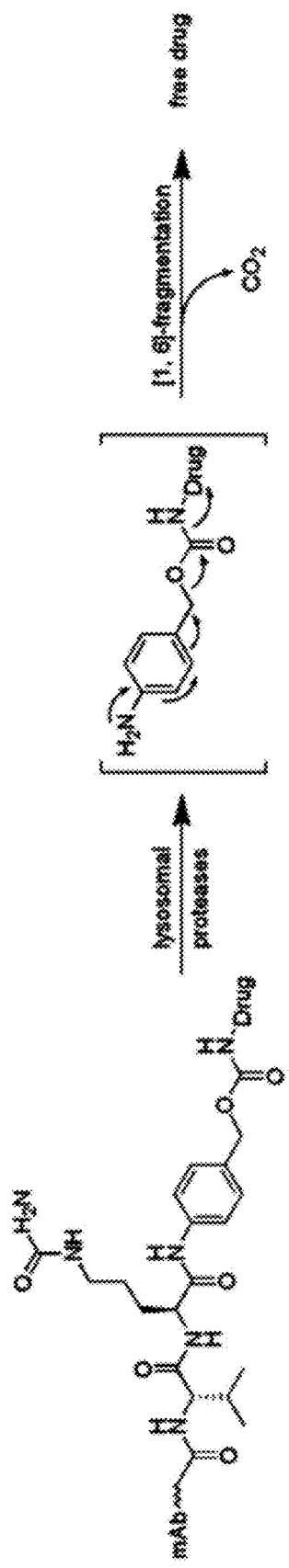
2) Glucuronide based drug linker
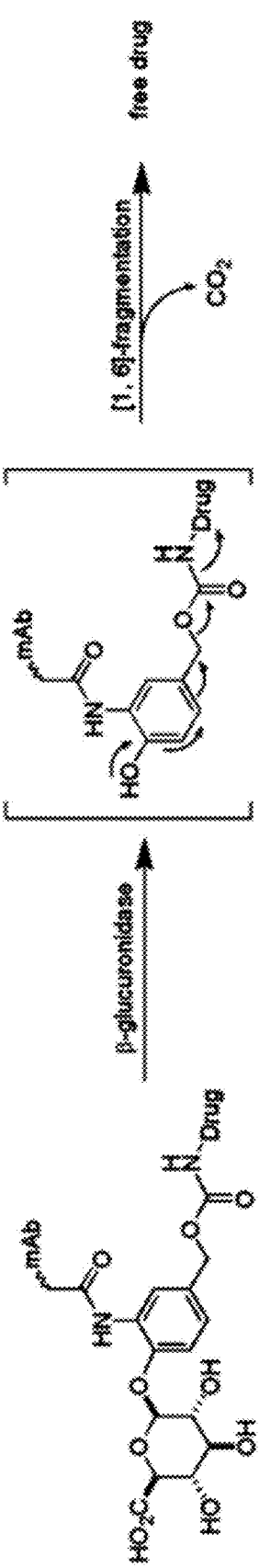

ANTIBODY-ACTIVE AGENT CONJUGATES AND METHODS OF USE

CROSS-REFERENCE TO RELATED APPLICATION

This application is a continuation of U.S. application Ser. No. 14/517,616, filed Oct. 17, 2014 and now granted as U.S. Pat. No. 9,669,107, which is a continuation of U.S. application Ser. No. 14/181,648, filed on Feb. 15, 2014 and now abandoned, which is a divisional of U.S. application Ser. No. 13/466,875, filed on May 8, 2012 and now abandoned, which claims the benefit of U.S. Provisional Application No. 61/483,698, filed on May 8, 2011. The entire contents of each of the above-referenced applications are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Jun. 2, 2017, is named LCH-001.06_SL.txt and is 62,011 bytes in size.

BACKGROUND

(a) Technical Field

The present disclosure relates to a protein-active agent conjugate. The protein (e.g., an oligopeptide, a polypeptide, an antibody, or the like) has substrate specificity for a desired target, and the active agent (e.g., a drug, a toxin, a ligand, a detection probe, and the like) has a specific function or activity. The disclosure also relates to methods for preparing the conjugate. The disclosure further relates to methods of using the conjugate to deliver an active agent to a target cell in a subject, as well as methods for treating a subject in need of the active agent (e.g., a subject having cancer).

(b) Background Art

Methods for inhibiting growth of cancer cells by targeted delivery of anti-cancer agents have been proposed. For example, it has been shown that targeted delivery of an antibody-drug conjugate can kill a particular cancer cell. As the antibody (or antibody fragment) specifically binds the cancer cell, the drug is delivered to the target cancer cell. Targeted delivery of the drug ensures that the drug acts on the target cancer cell instead of normal host cells, thereby minimizing the side effects resulting from damage to normal cells.

Antibody conjugates can be used to deliver chemical and/or biological molecules. Exemplary chemical and/or biological molecules include a drug conventionally used in chemical treatment, a bacterial protein toxin (e.g., diphtheria toxin), a plant protein toxin (e.g., ricin), a small molecule toxin (e.g., auristatin, geldanamycin, maytansinoid, calicheamycin, daunomycin, methotrexate, vindesine, and tubulysin), an affinity ligand, a detection probe (e.g., fluorescent probe, radioactive probe), and the like (including combinations thereof).

Antibody-drug conjugates that have been proposed thus far are prepared by bonding a drug moiety with a plurality of lysine groups of an antibody. Alternatively, antibody-drug conjugates are prepared by reducing all or part of the interchain disulfide groups of an antibody or reducing all the interchain disulfide groups followed by partial oxidation to thereby give free cysteine thiol groups, and then bonding the free cysteine thiol groups with a drug moiety.

Existing preparation methods, however, have some problems. For example, the overall preparation process is complicated because the antibody-drug conjugates prepared by the existing preparation methods are not uniform (homogeneous). When antibody-drug conjugates are prepared by bonding a drug moiety with lysine groups, various types and forms of antibody-drug conjugates are obtained due to the presence of many lysine groups in the antibody (e.g., 100 lysine groups per antibody). Similarly, when preparing antibody-drug conjugates by bonding thiol groups with a drug moiety, a mixture of diastereomers is obtained due to bonding between thiol groups and maleimide groups. For example, if n drugs are conjugated, a mixture of $2^n$ stereoisomers is obtained. Thus, where the drug distribution number is 0-8 (e.g., where interchain disulfide groups are reduced), a mixture of $$\sum_{n=0}^{n=8} 2^n$$

of stereoisomers is obtained. In addition, where i drugs are conjugated with q sites, a mixture of $$\sum_{i=0}^{q} qCi$$

of different compounds is obtained.

Furthermore, when preparing antibody-drug conjugates by bonding lysine groups with a drug moiety, the electric charge of the lysine groups may be lost, thereby causing the antibody to lose its unique antigen specificity. Likewise, the tertiary or quaternary structure of the antibody may not be maintained when preparing antibody-drug conjugates by reducing disulfide groups, thereby causing the antibody to be inactivated or become a non-specific antibody. When preparing antibody-drug conjugates by using thiol-maleimide bonding, the drug may be cleaved (non-specifically) from the conjugates via, e.g., a reverse reaction.

To overcome the problems associated with the prior preparation methods, an alternative method was proposed in which amino acid groups in particular positions of an antibody are replaced with cysteine groups. Although this method shows better result than the prior preparation methods in terms of toxicity, activity, and safety, this method still involves thiol-maleimide bonding and thus suffers from the diastereomer and instability problems associated with thiol-maleimide bonding. Another alternative method was proposed in which selenocysteine groups are attached to the carboxy terminals of an antibody.

In addition to use of cysteine substitutions to control the site of conjugation, Ambrx Technology (at the World Wide Web (www) ambrx.com) has been working toward incorporating non-natural amino acids in the antibody to provide functional groups that can be used for linker chemistry. Ambrx's expression systems contain tRNA synthetases that aminoacylate the original tRNA with a non-natural amino acid, thereby inserting a non-natural amino acid whenever the amber stop is encountered.

Redwood Bioscience's (at the World Wide Web (www) redwoodbioscience.com) technology employs genetically encoded aldehyde tags and aims to exploit a specific sequence that is posttranslationally recognized and modified by an enzyme, i.e., a formyl glycine-generating enzyme, to produce a so-called aldehyde chemical handle. The incorporation of a CxPxR sequence at specific positions in the antibody provides a means to produce a reactive aldehyde amenable to drug conjugation.

However, in view of the above-mentioned problems in the art pertaining to making antibody-drug conjugates, new antibody-drug conjugates and new methods of making antibody-drug conjugates are highly desirable.

The above information disclosed in this Background section is only for enhancement of understanding of the background of the invention and therefore it may contain information that does not form the prior art that is already known to a person of ordinary skill in the art.

SUMMARY OF THE DISCLOSURE

As described below, the present invention generally features protein-active agent conjugates and methods for making the protein-active agent conjugates. The invention also features methods for delivering the protein-active agent conjugate to a target cell in a subject, as well as methods for treating a subject in need of the active agent. The protein-active agent conjugates of the invention can be produced homogeneously and advantageously used for targeted treatment of a disease.

In aspects, the invention provides protein-active agent conjugates. In embodiments, the protein has an amino acid motif that can be recognized by an isoprenoid transferase. In embodiments, the active agent is covalently linked to the protein at the amino acid motif.

In embodiments, the protein has a deletion in the carboxy terminus of the protein. In related embodiments, the modification is attached to the amino acid motif.

In embodiments, the protein has an oligopeptide or polypeptide addition in the carboxy terminus of the protein. In related embodiments, the modification is attached to the amino acid motif.

In embodiments, the protein has a deletion in the carboxy terminus of the protein and an oligopeptide or polypeptide addition in the carboxy terminus of the protein. In related embodiments, the modification is attached to the amino acid motif.

In embodiments, the protein is an antibody or a fragment of an antigenic polypeptide. In related embodiments, the protein is a monoclonal antibody. In related embodiments, at least one light chain and/or at least one heavy chain of the monoclonal antibody comprises an amino acid region having the amino acid motif.

In any of the above aspects or embodiments, the isoprenoid transferase is FTase or GGTase.

In any of the above aspects or embodiments, the active agent is a drug, a toxin, an affinity ligand, a detection probe, or a combination thereof.

In any of the above aspects or embodiments, the amino acid motif is CAAX, XXCC, XCXC, or CXX, wherein C represents cysteine, A represents an aliphatic amino acid, and X represents an amino acid that determines a substrate specificity of the isoprenoid transferase.

In any of the above aspects or embodiments, the amino acid motif is covalently linked to the active agent via at least one linker. In related embodiments, the linker is an isoprenyl derivative that can be recognized by the isoprenoid transferase.

In related embodiments, the linker is represented by the following formula (I):

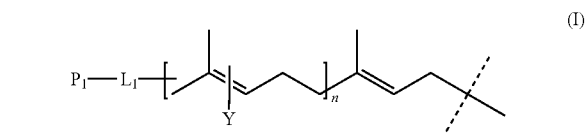

wherein, $P_1$ and Y is independently a group containing a first functional group (FG1), the FG1 being selected from the group consisting of: acetylene, azide, aldehyde, hydroxylamine, hydrazine, ketone, nitrobenzofurazan (NBD), dansyl, fluorescein, biotin, and Rhodamine, $L_1$ is $(CH_2)_r X_q (CH_2)_p$, X is oxygen, sulfur, $-NR_1-$, $-C(O)NR_1-$, $-NR_1C(O)-$, $-NR_1SO_2-$, $-SO_2NR_1-$, $-(CH=CH)-$, or acetylene, $R_1$ is hydrogen, $C_{1-6}$ alkyl, $C_{1-6}$ alkyl aryl, or $C_{1-6}$ alkyl heteroaryl, r and p is independently an integer of 0 to 6, q is an integer of 0 to 1, and n is an integer of 1 to 4.

In embodiments, the active agent is attached to a group containing a second functional group (FG2) that can react with the FG1. In related embodiments, FG2 is an acetylene, hydroxylamine, azide, aldehyde, hydrazine, ketone, or amine. In further related embodiments, the active agent is attached to the group containing an FG2 via $-(CH_2)_r X_q (CH_2)_p-$ or $-[ZCH_2CH_2O(CH_2CH_2O)_w CH_2CH_2Z]-$, in which X is oxygen, sulfur, $-NR_1-$, $-C(O)NR_1-$, $-NR_1C(O)-$, $-NR_1SO_2-$, or $-SO_2NR_1-$, Z is oxygen, sulfur or $NR_1$, $R_1$ is hydrogen, $C_{1-6}$ alkyl, $C_{1-6}$ alkyl aryl, or $C_{1-6}$ alkyl heteroaryl, r and p is independently an integer of 0 to 6, q is an integer of 0 to 1, and m is an integer of 0 to 6.

In yet further related embodiments, the $-(CH_2)_r X_q (CH_2)_p-$ or $-[ZCH_2CH_2O(CH_2CH_2O)_w CH_2CH_2Z]-$ is attached to (i) a peptide(s) that can be cleaved by cathepsin B or (ii) a glucuronide that can be cleaved by β-glucuronidase.

In embodiments, the peptide that can be cleaved by cathepsin B is

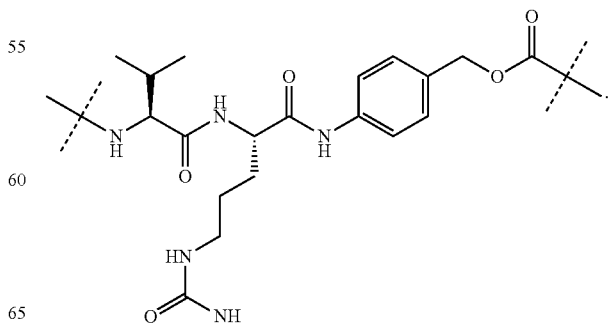

In embodiments, the glucuronide that can be cleaved by β-glucuronidase is

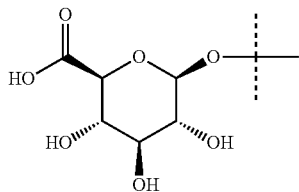

In aspects, the invention provides methods for preparing any of the protein-active agent conjugate described herein. In embodiments, the methods involve expressing a protein having an amino acid motif that can be recognized by an isoprenoid transferase. In embodiments, the methods involve enzymatically reacting, with the isoprenoid transferase, the expressed protein and at least one isosubstrate having a first functional group (FG1), thereby producing a functionalized protein. In embodiments, the methods involve attaching a second functional group (FG2) to an active agent, thereby producing a functionalized active agent. In embodiments, the methods involve reacting the functionalized protein with the functionalized active agent, thereby producing the protein-active agent conjugate.

In related embodiments, the amino acid motif is in the carboxy terminus of the protein.

In related embodiments, the amino acid motif is CAAX, XXCC, XCXC, or CXX, wherein C represents cysteine, A represents an aliphatic amino acid, and X represents an amino acid that determines the substrate specificity of the isoprenoid transferase.

In related embodiments, the amino acid motif is CAAX, and wherein the method further comprises removing AAX from the amino acid motif after step (b).

In related embodiments, the FG2 is attached to the active agent by at least one linker.

In related embodiments, the reaction between the functionalized protein and the functionalized active agent is click chemistry reaction or a hydrazone and/or oxime formation. In embodiments, the FG1 is an azide group and the FG2 is an acetylene group. In embodiments, the FG1 is an acetylene group and the FG2 is an azide group. In embodiments, the FG1 is an aldehyde or ketone group and the FG2 is a hydrazine or hydroxylamine. In embodiments, the FG1 is hydrazine or hydroxylamine and the FG2 is an aldehyde or ketone.

In aspects, the invention provides methods for preparing any of the protein-active agent conjugate described herein, and the methods involve expressing a protein having an amino acid motif that can be recognized by an isoprenoid transferase. In embodiments, the methods involve attaching an isosubstrate of an isoprenoid transferase to an active agent. In embodiments, the methods involve enzymatically reacting, with the isoprenoid transferase, the expressed protein and the active agent attached to the isosubstrate.

In related embodiments, the amino acid motif is in the carboxy terminus of the protein.

In related embodiments, the amino acid motif is CAAX, XXCC, XCXC, or CXX, wherein C represents cysteine, A represents an aliphatic amino acid, and X represents an amino acid that determines the substrate specificity of the isoprenoid transferase.

In related embodiments, the isosubstrate is attached to the active agent by at least one linker.

In aspects, the invention provides compositions containing any of the protein-active agent conjugates described herein. In embodiments, the composition is a homogeneous mixture of the protein-active agent conjugate. In embodiments, the protein is an antibody or a fragment of an antigenic polypeptide.

In aspects, the invention provides methods for delivering an active agent to a target cell in a subject. In embodiments, the methods involve administering at least one of the protein-active agent conjugates or compositions described herein. In embodiments, the target cell is a cancer cell.

In aspects, the invention provides methods for treating a subject in need thereof (i.e., in need of the active agent). In embodiments, the methods involve administering at least one of the protein-active agent conjugates or compositions described herein. In embodiments, the subject has cancer. In embodiments, the subject has an infection with a pathogenic agent. The pathogenic agent may be a virus, bacteria, fungus, or parasite.

In the above-described protein-active agent conjugates, compositions, and methods, in some embodiments, the active agent may be an immunomodulatory compound, an anti-cancer agent, an anti-viral agent, an anti-bacterial agent, an anti-fungal agent, or an anti-parasitic agent.

The above and other aspects, features, and advantages of the present invention will be apparent from or are set forth in more detail in the accompanying drawings, which are incorporated in and form a part of this specification, and the following Detailed Description, which together serve to explain by way of example the principles of the present invention.

BRIEF DESCRIPTION OF DRAWINGS

FIG. 1 shows an amino acid sequence of a modified Herceptin antibody (Herceptin-HC-GCVIM) ("Herceptin-HC-GCVIM" disclosed as SEQ ID NO: 8) prepared by inserting GCVIM (SEQ ID NO: 1) to the C-terminus of the heavy chain of Herceptin. Figure discloses SEQ ID NOS 8-9, respectively, in order of appearance.

FIG. 2 shows an amino acid sequence of a modified Herceptin antibody (Herceptin-LC-GCVIM) ("Herceptin-LC-GCVIM" disclosed as SEQ ID NO: 11) prepared by inserting GCVIM (SEQ ID NO: 1) to the C-terminus of the light chain of Herceptin. Figure discloses SEQ ID NOS 10-11, respectively, in order of appearance.

FIG. 3 shows an amino acid sequence of a modified Herceptin antibody (Herceptin-HC-$G_5$CVIM) ("Herceptin-HC-$G_5$CVIM" disclosed as SEQ ID NO: 12) prepared by inserting $G_5$CVIM (SEQ ID NO: 2) to the C-terminus of the heavy chain of Herceptin. Figure discloses SEQ ID NOS 12-13, respectively, in order of appearance.

FIG. 4 shows an amino acid sequence of a modified Herceptin antibody (Herceptin-LC-$G_5$CVIM) ("Herceptin-LC-$G_5$CVIM" disclosed as SEQ ID NO: 15) prepared by inserting $G_5$CVIM (SEQ ID NO: 2) to the C-terminus of the light chain of Herceptin. Figure discloses SEQ ID NOS 14-15, respectively, in order of appearance.

FIG. 5 shows an amino acid sequence of a modified Herceptin antibody (Herceptin-HC-$G_7$CVIM) ("Herceptin-HC-$G_7$CVIM" disclosed as SEQ ID NO: 16) prepared by inserting $G_7$CVIM (SEQ ID NO: 3) to the C-terminus of the heavy chain of Herceptin. Figure discloses SEQ ID NOS 16-17, respectively, in order of appearance.

FIG. 6 shows an amino acid sequence of a modified Herceptin antibody (Herceptin-LC-$G_7$CVIM) ("Herceptin-LC-$G_7$CVIM" disclosed as SEQ ID NO: 19) prepared by inserting G₇CVIM (SEQ ID NO: 3) to the C-terminus of the light chain of Herceptin. Figure discloses SEQ ID NOS 18-19, respectively, in order of appearance.

FIG. 7 shows an amino acid sequence of a modified Herceptin antibody (Herceptin-HC-G₁₀CVIM) ("Herceptin-HC-G₁₀CVIM" disclosed as SEQ ID NO: 20) prepared by inserting G₁₀CVIM (SEQ ID NO: 4) to the C-terminus of the heavy chain of Herceptin. Figure discloses SEQ ID NOS 20-21, respectively, in order of appearance.

FIG. 8 shows an amino acid sequence of a modified Herceptin antibody (Herceptin-LC-G₁₀CVIM) ("Herceptin-LC-G₁₀CVIM" disclosed as SEQ ID NO: 23) prepared by inserting G₁₀CVIM (SEQ ID NO: 4) to the C-terminus of the light chain of Herceptin. Figure discloses SEQ ID NOS 22-23, respectively, in order of appearance.

FIG. 9 shows an amino acid sequence of a modified Herceptin antibody (Herceptin-HC-G₁₀CVLL) ("Herceptin-HC-G₁₀CVLL" disclosed as SEQ ID NO: 24) prepared by inserting G₁₀CVLL (SEQ ID NO: 6) to the C-terminus of the heavy chain of Herceptin. Figure discloses SEQ ID NOS 24-25, respectively, in order of appearance.

FIG. 10 shows an amino acid sequence of a modified Herceptin antibody (Herceptin-LC-G₁₀CVLL) ("Herceptin-LC-G₁₀CVLL" disclosed as SEQ ID NO: 27) prepared by inserting G₁₀CVLL (SEQ ID NO: 6) to the C-terminus of the light chain of Herceptin. Figure discloses SEQ ID NOS 26-27, respectively, in order of appearance.

FIG. 11 shows an SDS-PAGE gel analyzing a modified anti cMET antibody (anti cMET-HC-G₇CVIM) ("G₇CVIM" disclosed as SEQ ID NO: 3) prepared by inserting G₇CVIM (SEQ ID NO: 3) to the C-terminus of the heavy chain of anti cMET antibody, a modified anti cMET antibody (anti cMET-LC-G₇CVIM) ("G₇CVIM" disclosed as SEQ ID NO: 3) prepared by inserting G₇CVIM (SEQ ID NO: 3) to the C-terminus of the light chain of anti cMET antibody, a modified anti cMET antibody (anti cMET-HC-G₁₀CVIM) ("G₁₀CVIM" disclosed as SEQ ID NO: 4) prepared by inserting G₁₀CVIM (SEQ ID NO: 4) to the C-terminus of the heavy chain of anti cMET antibody, and a modified anti cMET antibody (anti cMET-LC-G₁₀CVIM) ("G₁₀CVIM" disclosed as SEQ ID NO: 4) prepared by inserting G₁₀CVIM (SEQ ID NO: 4) to the C-terminus of the light chain of anti cMET antibody.

FIG. 17 shows the results from LC/MS analysis of a prenylated Herceptin-LC-GCVIM ("Herceptin-LC-G₇CVIM" disclosed as SEQ ID NO: 19).

FIG. 18 shows the results from LC/MS analysis of a prenylated Herceptin-LC-G₁₀CVIM ("Herceptin-LC-G₁₀CVIM" disclosed as SEQ ID NO: 23).

FIG. 20 shows the HIC-HPLC chromatograms of Herceptin-LC-G₇CVIM ("Herceptin-LC-G₇CVIM" disclosed as SEQ ID NO: 19), prenylated Herceptin-LC-G₇CVIM ("Herceptin-LC-G₇CVIM" disclosed as SEQ ID NO: 19), and LCB14-0101 (Herceptin-LC-G₇CVIM-BG-MMAF) ("G₇CVIM" disclosed as SEQ ID NO: 3).

FIG. 25 shows a mechanism of release of active drugs (except non-cleavable linker).

DETAILED DESCRIPTION OF THE DISCLOSURE

Figure 12:
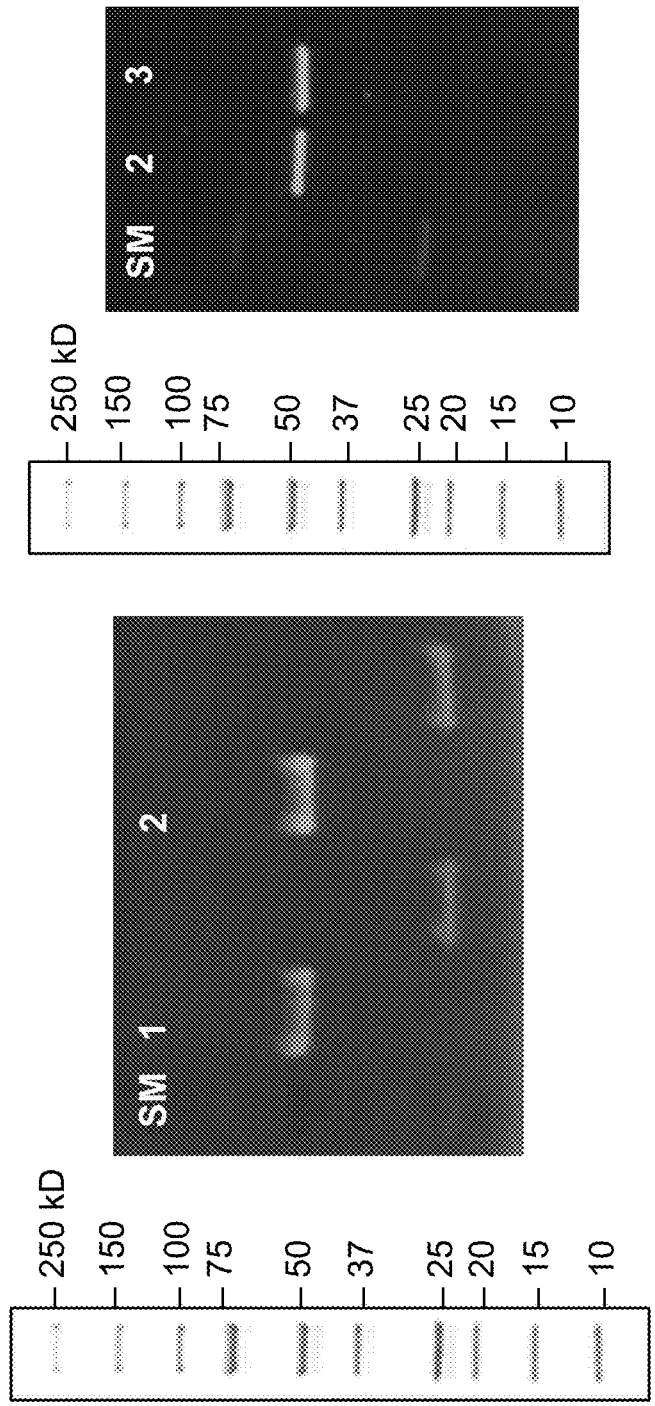
FIG. 12 shows an SDS-PAGE gel analyzing prenylation of Herceptin-HC-G$_n$CVIM ("G$_n$CVIM" disclosed as SEQ ID NO: 5) by using FTase and NBD-GPP. Figure discloses "G₇CVIM" as SEQ ID NO: 3 and "G₁₀CVIM" as SEQ ID NO: 4.

Reference will now be made in detail to embodiments of the present invention, examples of which are illustrated in the drawings attached hereinafter, wherein like reference numerals refer to like elements throughout. The embodiments are described below so as to explain the present invention by referring to the figures.

Definitions

By "agent" or "active agent" is meant any small molecule chemical compound, antibody, nucleic acid molecule, or polypeptide, or fragments thereof. Examples include, but are not limited to, a drug, a toxin, an affinity ligand, a detection probe, or a combination thereof.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Contacting a cell" is understood herein as providing an agent to a cell e.g., a cell to be treated in culture, ex vivo, or in an animal, such that the agent can interact with the cell (e.g., cell to be treated), potentially be taken up by the cell, and have an effect on the cell. The agent (e.g., an adjuvant) can be delivered to the cell directly (e.g., by addition of the agent to culture medium or by injection into the cell or tissue of interest), or by delivery to the organism by a topical or parenteral route of administration for delivery to the cell by vascular, lymphatic, or other means. One of ordinary skill in the art will readily understand that administration of the protein-active agent conjugates of the invention to a subject involves contacting the protein-active agent conjugate with a cell of the subject.

By "disease" is meant any condition or disorder that damages or interferes with the normal function of a cell, tissue, or organ.

The terms "effective amount," "therapeutically effective amount," "effective dose," or "therapeutically effective dose" refers to that amount of an agent to produce the intended pharmacological, therapeutic, or preventive result. For example, the pharmacologically effective amount results in the prevention or delay of onset of disease, either in an individual or in the frequency of disease in a population. More than one dose may be required to provide an effective dose. It is understood that an effective dose in one population may or may not be sufficient in all populations. Thus, in connection with the administration of an agent or immunogenic composition, the agent or immunogenic composition is "effective against" a disease or condition when administration in a clinically appropriate manner results in a beneficial effect for at least a statistically significant fraction of subjects, such as a prevention of disease onset, improvement of symptoms, a cure, a reduction in disease signs or symptoms, extension of life, improvement in quality of life, or other effect generally recognized as positive by medical doctors familiar with treating the particular type of disease or condition.

By "enhances" is meant a positive alteration of at least 10%, 25%, 50%, 75%, 100%, or any number therebetween.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleotide bases. For example, adenine and thymine are complementary nucleotide bases that pair through the formation of hydrogen bonds.

"Obtaining" is understood herein as manufacturing, purchasing, synthesizing, isolating, purifying, or otherwise coming into possession of.

The phrase "pharmaceutically acceptable carrier, excipient, or diluent" is art recognized and includes a pharmaceutically acceptable material, composition or vehicle, suitable for administering compounds of the present invention to mammals. As used herein, the term "pharmaceutically acceptable" means being approved by a regulatory agency of the Federal or a state government or listed in the U.S. Pharmacopia, European Pharmacopia or other generally recognized pharmacopia for use in mammals, e.g., humans.

By "reduces" is meant a negative alteration of at least 10%, 25%, 50%, 75%, 100%, or any number therebetween.

By "reference" is meant a standard or control condition.

A "sample" as used herein refers to a biological material that is isolated from its environment (e.g., blood or tissue from an animal, cells, or conditioned media from tissue culture). In embodiments, the sample is suspected of containing, or known to contain an analyte, such as a protein of interest (e.g., antibody, cytokine, and the like). A sample can also be a partially purified fraction of a tissue or bodily fluid. A reference sample can be a "normal" sample, from a donor not having the disease or condition fluid, or from a normal tissue in a subject having the disease or condition, or an untreated subject (e.g., a subject not treated with the vaccine). A reference sample can also be taken at a "zero time point" prior to contacting the cell or subject with the agent or therapeutic intervention to be tested.

By "specifically binds" is meant recognition and binding to a target (e.g., polypeptide, cell, and the like), but which does not substantially recognize and bind other molecules in a sample, for example, a biological sample.

A "subject" as used herein refers to a living organism. In embodiments, the living organism is an animal. In embodiments, the subject is a mammal. In embodiments, the subject is a domesticated mammal or a primate including a non-human primate. Examples of subjects include, but are not limited to, humans, monkeys, dogs, cats, mice, rats, cows, horses, swine, goats, sheep, and birds. A subject may also be referred to as a patient.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from a disease or condition is within the ability of those in the art. Subjects suffering from, and suspected of suffering from, a specific disease, condition, or syndrome are not necessarily two distinct groups. One of ordinary skill in the art would also readily understand that a subject in need of an active agent may also be a subject suffering from or suspected of suffering from a specific disease, condition, or syndrome.

As used herein, the terms "treat," "treating," "treatment," and the like refer to reducing or ameliorating a disorder and/or symptoms associated therewith (e.g., cancer or cancer associated symptoms). It will be appreciated that, although not precluded, treating a disorder or condition does not require that the disorder, condition or symptoms associated therewith be completely eliminated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

1. Methods for Preparing Protein-Active Agent Conjugates

Methods for making the protein-active agent conjugates of the invention and variations thereof are readily apparent to one of ordinary skill in the art based on the disclosures herein. Provided below are exemplary methods, which are provided by way of illustration, and are not intended to be limiting of the present invention.

Embodiment 1

A method for preparing a protein-active agent conjugate according to one embodiment of the invention comprises: (a) expressing a protein having an amino acid motif that can be recognized by an isoprenoid transferase; (b) enzymatically reacting, using the isoprenoid transferase, the expressed protein and at least one isosubstrate having a first functional group (FG1), thereby producing a functionalized protein; (c) attaching a second functional group (FG2) to an active agent, thereby producing a functionalized active agent; and (d) reacting the functionalized protein with the functionalized active agent, thereby producing the protein-active agent conjugate.

The term "protein" used herein is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments).

A protein refers to an oligopeptide or polypeptide containing at least one C-terminus and at least one N-terminus. The term is used herein to include an intact oligopeptide or polypeptide, a modified form thereof, a fragment thereof, and analogs thereof. For example, the term can refer to an oligopeptide or polypeptide, or an oligopeptide or polypeptide modified by attaching thereto an amino acid sequence that can be recognized by an isoprenoid transferase. The term "fragment" used herein refers to a portion of the amino acid sequence consisting of an oligopeptide or polypeptide. The term is used herein to include a portion of the amino acid sequence that has the substrate specificity of the oligopeptide or polypeptide. The term "analog" refers to an oligopeptide or polypeptide having a sequence identity of at least 70% or 75%, at least 80% or 85%, at least 90%, 91%, 92%, 93%, 94%, or 95%, or at least 96, 97%, 98%, or 9% with a reference oligopeptide or polypeptide.

The term "protein" used herein also includes an antibody a fragment of an antigenic polypeptide, or an analog or derivative thereof. The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')$_2$, Fd, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations.

The term "antibody fragment" refers to a portion of an intact antibody and refers to the antigenic determining variable regions of an intact antibody. Examples of antibody fragments include, but are not limited to Fab, Fab', F(ab')$_2$, Fd, and Fv fragments, linear antibodies, single chain antibodies, and multispecific antibodies formed from antibody fragments.

A "monoclonal antibody" refers to homogenous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')$_2$, Fd, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, and hamster) that have the desired specificity, affinity, and capability (Jones et al., 1986, *Nature*, 321:522-525;

Riechmann et al., 1988, *Nature,* 332:323-327; Verhoeyen et al., 1988, *Science,* 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residue either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, at least 5, or at least 8-10 amino acids in a unique spatial conformation.

That an antibody "specifically binds" to an epitope or antigenic molecule means that the antibody reacts or associates more frequently, more rapidly, with greater duration, with greater affinity, or with some combination of the above to an epitope or antigenic molecule than with alternative substances, including unrelated proteins. In certain embodiments, "specifically binds" means, for instance, that an antibody binds to a protein with a $K_D$ of about 0.1 mM or less, but more usually less than about 1 µM. In certain embodiments, "specifically binds" means that an antibody binds to a protein at times with a $K_D$ of at least about 0.1 µM or less, and at other times at least about 0.01 µM or less. Because of the sequence identity between homologous proteins in different species, specific binding can include an antibody that recognizes a particular protein in more than one species. It is understood that an antibody or binding moiety that specifically binds to a first target may or may not specifically bind to a second target. As such, "specific binding" does not necessarily require (although it can include) exclusive binding, i.e. binding to a single target. Generally, but not necessarily, reference to binding means specific binding.

The antibodies, including fragments/derivatives thereof and monoclonal antibodies, can be obtained using known methods in the art. (See McCafferty et al., Nature 348:552-554 (1990); Clackson et al., Nature 352:624-628; Marks et al., J. Mol. Biol. 222:581-597 (1991); Marks et al., Bio/Technology 10:779-783 (1992); Waterhouse et al., Nucleic. Acids Res. 21:2265-2266 (1993); Morimoto et al., Journal of Biochemical and Biophysical Methods 24:107-117 (1992); Brennan et al., Science 229:81 (1985); Carter et al., Bio/Technology 10:163-167 (1992); Kohler et al., Nature 256:495 (1975); U.S. Pat. No. 4,816,567); Kilpatrick et al., Hybridoma 16(4):381-389 (1997); Wring et al., J. Pharm. Biomed. Anal. 19(5):695-707 (1999); Bynum et al., Hybridoma 18(5):407-411 (1999), Jakobovits et al., Proc. Natl. Acad. Sci. USA, 90:2551 (1993); Jakobovits et al., Nature, 362:255-258 (1993); Bruggemann et al., Year in Immuno. 7:33 (1993); Barbas et al., Proc. Nat. Acad. Sci. USA 91:3809-3813 (1994); Schier et al., Gene 169:147-155 (1995); Yelton et al., J. Immunol. 155:1994-2004 (1995); Jackson et. al., J. Immunol. 154(7):3310-9 (1995); Hawkins et al., J. Mol. Biol. 226:889-896 (1992), U.S. Pat. Nos. 5,514,548, 5,545,806, 5,569,825, 5,591,669, 5,545,807; WO 97/17852, all of which are herein incorporated by reference in their entirety.)

Non-limiting examples of the antibody include, but not limited to, Muromonab-CD3 Abciximab, Rituximab, Daclizumab, Palivizumab, Infliximab, Trastuzumab, Etanercept, Basiliximab, Gemtuzumab ozogamicin, Alemtuzumab, Ibritumomab tiuxetan, Adalimumab, Alefacept, Omalizumab, Efalizumab, Tositumomob-I131, Cetuximab, Bevacizumab, Natalizumab, Ranibizumab, Panitumumab, Ecolizumab, Rilonacept, Certolizumab pegol, Romiplostim, AMG-531, CNTO-148, CNTO-1275, ABT-874, LEA-29Y, Belimumab, TACI-Ig, 2nd gen. anti-CD20, ACZ-885, Tocilizumab (Atlizumab), Mepolizumab, Pertuzumab, Humax CD20, CP-675, 206 (Ticilimumab), MDX-010, IDEC-114, Inotuzumab ozogamycin, HuMax EGFR, Aflibercept, VEGF Trap-Eye, HuMax-CD4, Ala-Ala, ChAglyCD3; TRX4, Catumaxomab, IGN101, MT-201, Pregovomab, CH-14.18, WX-G250, AMG-162, AAB-001, Motavizumab; MEDI-524, efumgumab, Aurograb®, Raxibacumab, 3rd gen. anti-CD20, LY2469298, Veltuzumab.

In some embodiments, when the protein is a monoclonal antibody, at least one light chain of the monoclonal antibody, at least one heavy chain of the monoclonal antibody, or both may comprise an amino acid region having an amino acid motif that can be recognized an isoprenoid transferase.

In embodiments, the C-terminus of the light or heavy chain is modified. Also, the CH2 regions of the Fc region may be glycosylated.

In some embodiments, a C-terminus of a protein (a fragment, analog, or derivative thereof) can be attached to an amino acid motif that can be recognized by isoprenoid transferase. In other embodiments, the C-terminus can be modified. The modification can be (i) a deletion in the carboxy terminus of the protein, (ii) an oligopeptide or polypeptide addition in the carboxy terminus of the protein, or (iii) a deletion in the carboxy terminus of the protein and an oligopeptide or polypeptide addition in the carboxy terminus of the protein. In related embodiments, the modification can be attached to the amino acid motif.

The term "isoprenoid transferase" used herein refers to an enzyme that can recognize a certain amino acid motif at or near a C-terminus of a protein and perform selective alkylation at thiol position(s) of cysteine residue(s) of the certain amino acid motif by adding an isoprenoid unit(s) to the protein bearing the certain amino acid motif.

Examples of the isoprenoid transferase include farnesyltransferase (FTase) and geranylgeranyltransferase (GGTase), which involve the transfer of a farnesyl or a geranylgeranyl moiety to C-terminal cysteine(s) of the target protein, respectively. GGTase can be classified into GGTase I and GGTase II. FTase and GGTase I can recognize a CAAX motif and GGTase II can recognize a XXCC, XCXC, or CXX motif, in which C represents cysteine, A represents an aliphatic amino acid, and X represents an amino acid that determines the substrate specificity of the isoprenoid transferases (Nature Rev. Cancer 2005, 5(5), pp. 405-12; Nature Chemical Biology, 2010, 17, pp. 498-506; Lane K T, Bees L S, Structural Biology of Protein of Farnesyltransferase and Geranylgeranyltransferase Type I, Journal of Lipid Research, 47, pp. 681-699 (2006); Patrick J. Kasey, Miguel C. Seabra; Protein Prenyltransferases, The Journal of Biological Chemistry, Vol. 271, No. 10, Issue of March 8, pp. 5289-5292 (1996), the contents of these references are hereby incorporated by reference in their entirety).

In the present invention, isoprenoid transferases from a variety of sources, e.g., humans, animals, plants, bacteria, virus, and the like can be used. In some embodiments, naturally occurring isoprenoid transferases can be used. In some other embodiments, naturally or artificially modified isoprenoid transferases can be used. For example, an isoprenoid transferase having at least one amino acid sequence naturally changed (including post-translational modification), a naturally or artificially truncated form of a naturally occurring isoprenoid transferase, an isoprenoid transferase that has been modified by at least one of (His)-tag, GST, GFP, MBP, CBP, Isopeptag, BCCP, Myc-tag, Calmodulin-tag, FLAG-tag, HA-tag, Maltose binding protein-tag, Nus-tag, Glutathione-S-transferase-tag, Green fluorescent protein-tag, Thioredoxin-tag, S-tag, Softag 1, Softag 3, Strep-tag, SBP-tag, Ty-tag, and the like.

Isoprenoid transferases can recognize an isosubstrate as well as a substrate. The isosubstrate refers to a substrate analog which has a modification in the substrate. Isoprenoid transferases alkylate a certain amino acid motif (e.g., CAAX motif) at a C-terminus of a protein (Benjamin P. Duckworth et al, ChemBioChem 2007, 8, 98; Uyen T. T. Nguyen et al, ChemBioChem 2007, 8, 408; Guillermo R. Labadie et al, J. Org. Chem. 2007, 72(24), 9291; James W. Wollack et al, ChemBioChem 2009, 10, 2934, the contents of which are incorporated herein by reference.). A functionalized protein can be produced using an isoprenoid transferase and an isosubstrate through alkylation at a C-terminal cysteine(s).

For example, the cysteine residue of a C-terminal CAAX motif can be reacted with an isosubstrate using an isoprenoid transferase. In certain cases, AAX can then be removed by a protease. The resulting cysteine can then be methylated at the carboxy terminus by an enzyme. (Iran M. Bell, J. Med. Chem. 2004, 47(8), 1869, which is incorporated herein by reference.)

In the case of some proteins, cysteinylation and glutathionylation through disulfide bond formation can occur due to post-translational modification. Such a disulfide bond, however, can be reduced when such alkylation occurs by isoprenoid transferases.

The proteins of the present invention can be made using any molecular biology or cell biology method well known in the art. For example, transient transfection methods can be used. Genetic sequences encoding a certain amino acid motif that can be recognized by an isoprenoid transferase can be inserted into a known plasmid vector using standard PCR technologies so as to express a protein (a fragment or analog thereof) having the certain amino acid motif at a C-terminus thereof. As such, a protein having at least one amino acid motif that can be recognized by an isoprenoid transferase can be expressed. The expressed protein can then be enzymatically reacted with an isosubstrate of an isoprenoid transferase using the isoprenoid transferase to produce a functionalized protein. The isosubstrate contains a functional group.

Once a protein having an amino acid motif that can be recognized by an isoprenoid transferase is expressed, it may be enzymatically reacted, using an isoprenoid transferase and at least one isosubstrate having a first functional group (FG1), thereby producing a functionalized protein.

The term "functional group" used herein refers to a group that can lead to, e.g., 1,3-dipolar cycloaddition reactions, hetero-diels reactions, nucleophilic substitution reactions (e.g., of a ring opening reaction of a heterocyclic electrophile such as epoxide, aziridine, cyclic sulfate, and aziridium), non-aldol type carbonyl reactions (e.g., formation of oxime ethers, ureas, thioureas, aromatic heterocycles, hydrazones and amides), additions to carbon-carbon multiple bonds, oxidation reactions (e.g., epoxidation, aziridination, and sulfenyl halide addition), and click chemistry. The functional group can include, but not limited to, a fluorescent tag, a triazole, a maleimide, and a radioisotope (Angew. Chem. Int. Ed. 2001, 40, 2004-2021; Drug Discovery Today, 2003, 8(24), 1128-1137; Chem. Rev. 2008, 108, 2952-3015, the contents of which are incorporated herein by reference.) In embodiments, the functional group can be an acetylene group and an azide group.

The functional group can be attached to a protein or an active agent via at least one linker. In some embodiments, the linker is a linear linker. In some other embodiments, the linker is a branched linker. When the link is a branched linker, active agents can be attached to all of the branches. Each branch can have the same or different active agents. In some embodiments, the linker can be cleavable. In some other embodiments, it can be non-cleavable.

In some embodiments, a functionalized active agent is produced by attaching a second functional group (FG2) to an active agent. Exemplary active agents include, but are not limited to, a drug, a toxin, an affinity ligand, a detection probe, or a combination thereof.

Exemplary drugs include, but are not limited to, erlotinib (TARCEVA; Genentech/OSI Pharm.), bortezomib (VELCADE; MilleniumPharm.), fulvestrant (FASLODEX; AstraZeneca), sutent (SU11248; Pfizer), letrozole (FEMARA; Novartis), imatinib mesylate (GLEEVEC; Novartis), PTK787/ZK 222584 (Novartis), oxaliplatin (Eloxatin; Sanofi), 5-fluorouracil (5-FU, leucovorin, rapamycin (Sirolimus, RAPAMUNE; Wyeth), lapatinib (TYKERB, GSK572016; GlaxoSmithKline), lonafarnib (SCH 66336), sorafenib (BAY43-9006; Bayer Labs.), gefitinib (IRESSA; Astrazeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimine and methylamelamines including altretamine, triethylenemelamine, trietylenephosphoramide, triethiylenethiophosphoramide and trimethylolomelamine; acetogenins (especially, bullatacin and bullatacinone); camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosourea such as carmustine, chlorozotocin, fotemustine, lomustine, nimustine, and ranimnustine; antibiotics such as the enediyne antibiotics (e.g, calicheamycin, especially calicheamycin gamma1 I and calicheamycin omega1I (see, e.g., Agnew, Chem Intl ed. Engl., 33: 183-186 (1994)) and dynemicin, including dynemicin A; bisphosphonate such as clodronate; esperamicin, neocarzinostatin chromophore and related chromoprotein enediyne antibiotic chromophores, aclacinomysins, actinomycin, antrmycin, azaserine, bleomycins, cactinomycin, carabicin, carninomycin, carzinophilin, chromomycins, dactinomycin, daunorubicin, detorubicin, 6-diazo-5-oxo-L-norleucine, ADRLIMYCIN® doxorubicin (including morpholino-doxorubicin, cyanomorpholino-doxorubicin, 2-pyrrolino-doxorubicin, liposomal doxorubicin and deoxydoxorubicin), epirubicin, esorubicin, marcellomycin, mitomycins such as mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin, and zorubicin; anti-metabolites such as 5-fluorouracil (5-FU); folic acid analogues such as denopterin, methotrexate, pteropterin, trimetrexate; purine analogs such as fludarabine, 6-mercaptopurine, thiamiprine, and thiguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ('Ara-C'); cyclophosphamide; thiotepa; taxoids, e.g., TAXOL® paclitaxel (Bristol-Myers Squibb Oncology, Princeton, N.J.) ABRAXANE™ cremophor-free, albumin-engineered nanoparticle formulation of paclitaxel (American Pharmaceutical Partners, Schaumber, Ill.), and TAXOTERE® doxetaxel (Rhone-Poulenc Rorer, Antony, France); chloranbucil; gemcitabine; 6-thioguanine; mercaptopurine; platinum analogs such as cisplatin, carboplatin; vinblastine; platinum; etoposide, ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluorometlhylornithine (DFMO); retinoids such as retinoic acid; capecitabine; and pharmaceutically acceptable salts, solvates, acids, or derivatives thereof.

Additional drugs include, but are not limited to, (i) anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FAREATON® toremifene; (ii) aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, FEMARA® letrozole, and ARIMIDEX® anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those that inhibit expression of genes in signaling pathways implicated in aberrant cell proliferation, such as, for example, PKC-alpha, Raf, H-Ras; (viii) ribozyme, for example, VEGF inhibitor such as ANGIOZYME ribozyme and HER2 expression inhibitors; (ix) vaccines such as gene therapy vaccine; ALLOVECTIN® vaccine, LEUVECTIN vaccine and VAXID vaccine; PROLEUKIN®rIL-2; LUR-TOTECAN® topoisomerase 1 inhibitor; ABARELIX® rmRH; (x) an anti-angiogenic agent such as Bevacizumab (AVASTIN, Genentech); and (xi) pharmaceutically acceptable salts, solvates, acids, or derivatives thereof.

In some embodiments, cytokines can be used as the drug. Cytokines are small cell-signaling protein molecules that are secreted by numerous cells and are a category of signaling molecules used extensively in intercellular communication. They include monokines, lymphokines, traditional polypeptide hormones, and the like. Examples of cytokines include, but are not limited to, growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor fibroblast growth factor; prolactin; placental lactogen; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-$\beta$; platelet-growth factor; transforming growth factors (TGFs) such TGF-$\alpha$ and TGF-$\beta$; insulin-like growth factor-I and -II; erythropoietin (EPO); osteoinductive factors; interferons such as interferon-$\alpha$, -$\beta$, and -$\gamma$; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1$\alpha$, IL-2, IL-3, IL-4, IL-5, IL-6, IL-7, IL-8, IL-9, IL-10, IL-11, IL-12; a tumor necrosis factor such as TNF-$\alpha$ and TNF-$\beta$; and other polypeptide factors including LIF and kit ligand (KL). As used herein, the term cytokine also includes proteins from natural sources or from recombinant cell culture and biologically active equivalents of the native sequence cytokines.

The term "toxin" refers to a poisonous substance produced within living cells or organisms. Toxins can be small molecules, peptides or proteins that are capable of causing disease on contact with or absorption by body tissue interacting with biological macromolecules such as enzyme or cellular receptors. Toxins include plant toxins and animal toxins. Examples of animal toxins include, but are not limited to, diphtheria toxin, botulinum toxin, tetanus toxin, dysentery toxin, cholera toxin, tetrodotoxin, brevetoxin, ciguatoxin. Examples of plant toxins include, but are not limited to, ricin and AM-toxin.

Examples of small molecule toxins include, but are not limited to, auristatin, geldanamycin (Kerr et al., 1997, Bioconjugate Chem. 8(6):781-784), maytansinoids (EP 1391213, ACR 2008, 41, 98-107), calicheamycin (US 2009105461, Cancer Res. 1993, 53, 3336-3342), daunomycin, doxorubicin, methotrexate, vindesine, SG2285 (Cancer Res. 2010, 70(17), 6849-6858), dolastatin, dolastatin analogue's auristatin (US563548603), cryptophycin, camptothecin, rhizoxin derivatives, CC-1065 analogues or derivatives, duocarmycin, enediyne antibiotics, esperamicin, epothilone, and toxoids. Toxins can exhibit cytotoxicity and cell growth-inhibiting activity by tubulin binding, DNA binding, topoisomerase suppression, and the like.

The term "ligand" refers to a molecule that can form a complex with a target biomolecule. An example of a ligand is a molecule that is attached to a predetermined position of a targeted protein and transmits a signal. It can be a substrate, an inhibitor, a stimulating agent, a neurotransmitter, or a radioisotope.

"Detectable moiety" or a "label" refers to a composition detectable by spectroscopic, photochemical, biochemical, immunochemical, radioactive, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, flow cytometry, ELISA, or direct anlaysis by mass spectreometry of intact or subsequently digested peptides (one or more peptide can be assessed). Persons of skill in the art are familiar with techniques for labeling compounds of interest, and means for detection. Such techniques and methods are conventional and well-known in the art.

The term "probe" as used herein refers to a material that can (i) provide a detectable signal, (ii) can interact a first probe or a second probe to modify a detectable signal provided by the first or second probe, such as fluorescence resonance energy transfer (FRET), (iii) stabilize the interaction with an antigen or a ligand or increase the binding affinity; (iv) affect electrophoresis mobility or cell-intruding activity by a physical parameter such as charge, hydrophobicity, etc., or (v) control ligand affinity, antigen-antibody binding, or ionic complex formation.

Once the functionalized protein and the functionalized active agent are produced, they are reacted with each other, thereby producing the protein-active agent conjugate. In embodiments, the reaction between the functionalized protein and the functionalized active agent may be a click chemistry reaction or via a hydrazone and/or oxime formation. In embodiments, the FG1 is an azide group and the FG2 is an acetylene group, or vice versa. In other embodiments, the FG1 may be an aldehyde or ketone group and the FG2 is a hydrazine or hydroxylamine, or vice versa.

Click chemistry reactions are conducted in a mild condition, making it possible to handle proteins easily. Click chemistry reaction shows very high reaction specificity. Thus, even if a protein has other functional groups (e.g., side chain residue or at a C-terminus or N-terminus), these functional groups are not affected by the click chemistry reaction. For example, a click chemistry reaction between an acetylene group and an azide group of a protein can occur while other functional groups of the protein are not affected by the click chemistry reaction. In addition, a click chemistry reaction can specifically occur without being affected by the kind of ligand involved. In some cases, the ligand can be selected to improve overall reaction efficiency. For example, azide-acetylene click chemistry can produce a triazole at a high yield (Rhiannon K. Iha et al, Chem. Rev. 2009, 109, 5620; Morten Meldal and Christian Wenzel Tornoe, Chem Rev., 2008, 108, 2952; Hartmuth C. Kolb et al, Angew. Chemie Int. Ed. Engl., 2001, 40, 2004, all of which are incorporated herein by reference.)

Azide and acetylene groups are functional groups that do not exist in amino acid sequences of naturally occurring proteins. If a conjugation reaction occurs using these functional groups, none of the side chain residues and none of the N-terminal or C-terminal functional groups are affected by the click chemistry reaction. Accordingly, a protein-active agent conjugate in which an active agent is conjugated at a targeted position(s) can be produced.

When the protein is an antibody, all or a part of the antibody can be reduced to a single chain during alkylation by an isoprenoid transferase. The single chain can be oxidized to form a $H_2L_2$-form antibody due to an oxidizer used in the click chemistry reaction.

As the antibody has 4 chains (2H+2L), alkylation can be made at 1-4 positions per antibody. The number of the active agents can be more than 4 since a plurality of the active agents can be attached to a linker.

In certain embodiments, when the amino acid motif that can be recognized by the isoprenoid transferase is CAAX, the method may further include removing AAX. In other embodiments, the method may further include adding a methyl group at the C-terminus after removing AAX (Journal of Lipid Research, 2006, 47, 681-699, which is incorporated herein by reference.).

Embodiment 2

A method for preparing a protein-active agent conjugate according to another embodiment comprises: (a) expressing a protein having an amino acid motif that can be recognized by an isoprenoid transferase; (b) attaching an isosubstrate of an isoprenoid transferase to an active agent; and (c) enzymatically reacting, using the isoprenoid transferase, the expressed protein with the active agent attached to the isosubstrate.

In this embodiment, once a protein having an amino acid motif that can be recognized by an isoprenoid transferase is expressed, the protein is reacted with an active agent attached to an isosubstrate of the isoprenoid transferase. In this case, thiol-maleimide conjugation may occur. However, even if thiol-maleimide conjugation occurs, the active agents are conjugated at the targeted positions only according to the present invention. Accordingly, a problem associated with the prior art that a non-homogeneous mixture is produced is avoided.

2. Protein-Active Agent Conjugates

In another aspect, the present invention provides a protein-active agent conjugate comprising a protein having an amino acid motif that can be recognized by an isoprenoid transferase, wherein the active agent is covalently linked to the protein at the amino acid motif.

One of ordinary skill in the art is readily able to select a protein that selectively binds a target of interest (e.g., a target cell in a subject). Exemplary proteins include, but are not limited to antibodies or fragments of an antigen-binding protein that specifically bind to the target of interest.

CAAX Protein (CAAX Antibody)

An example of a protein-active agent conjugate prepared by a method of the present invention is represented by the following formula (I), in which the protein is an antibody (fragment or analog thereof) (Ab), the active agent is a drug (D), and the amino acid motif that can be recognized by an isoprenoid transferase is CAAX.

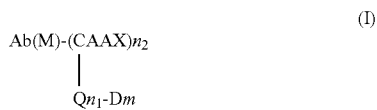
(I)

Ab(M) represents that the antibody or fragment thereof, which can comprise a modification. The modification can be (i) a deletion in the carboxy terminus of the antibody or fragment thereof, (ii) an oligopeptide or polypeptide addition in the carboxy terminus of the antibody or fragment thereof; and (iii) a deletion in the carboxy terminus of the antibody or fragment thereof and an oligopeptide or polypeptide addition in the carboxy terminus of the antibody or fragment thereof. Q represents a linker. The linker can be a linear linker or a branched linker. In an embodiment, the linker can include a first functional group (FG1). $n_1$, $n_2$, and m can be appropriately determined depending on the antibody, the amino acid motif, linker, active agent, etc. Preferably, $n_1$ and $n_2$ are independently an integer of 1 to 4 and m is an integer of 1 to 16.

In some embodiments, the linker can be represented by the following formula (II):

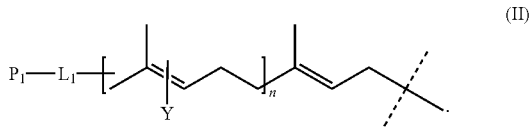
(II)

$P_1$ and Y is independently a group containing a first functional group (FG1). The FG 1 can be selected from the group consisting of: acetylene, azide, aldehyde, hydroxylamine, hydrazine, ketone, nitrobenzofurazan (NBD), dansyl, fluorescein, biotin, and Rhodamine. $L_1$ is $(CH_2)_rX_q(CH_2)_p$, in which X is oxygen, sulfur, —$NR_1$—, —$C(O)NR_1$—, —$NR_1C(O)$—, —$NR_1SO_2$—, —$SO_2NR_1$—, —(CH=CH)—, or acetylene; $R_1$ is hydrogen, $C_{1-6}$ alkyl, $C_{1-6}$ alkyl aryl, or $C_{1-6}$ alkyl heteroaryl; r and p is independently an integer of 0 to 6; q is an integer of 0 or 1; and n is an integer of 1 to 4.

In some certain embodiments, the drug (D) can be attached to the linker via a group containing a second functional group (FG2) that can react with the FG1. The FG2 can be selected from the group consisting of: acetylene, hydroxylamine, azide, aldehyde, hydrazine, ketone, and amine.

In some certain embodiments, the drug (D) can be attached to the group containing an FG2 via —$(CH_2)_rX_q$ $(CH_2)_p$— or —$[ZCH_2CH_2O(CH_2CH_2O)_wCH_2CH_2Z]$—, in which X is oxygen, sulfur, —$NR_1$—, —$C(O)NR_1$—, —$NR_1C(O)$—, —$NR_1SO_2$—, or —$SO_2NR_1$—; Z is oxygen, sulfur or $NR_1$; $R_1$ is hydrogen, $C_{1-6}$ alkyl, $C_{1-6}$ alkyl aryl, or $C_{1-6}$ alkyl heteroaryl; r and p is independently an integer of 0 to 6; q is an integer of 0 to 1; and w is an integer of 0 to 6.

In some certain embodiments, (i) a peptide(s) that can be cleaved by cathepsin B or (ii) a glucuronide that can be cleaved by β-glucuronidase can be attached to the —$(CH_2)_rX_q(CH_2)_p$— or —$[ZCH_2CH_2O(CH_2CH_2O)_w$ $CH_2CH_2Z]$—.

In some certain embodiments, a non self-immolative group or a self-immolative group can be attached to the (i) peptide(s) that can be cleaved by cathepsin B or (ii) glucuronide that can be cleaved by β-glucuronidase. Non-limiting examples of the self-immolative group may be aminophenylmethyloxycarbonyl and hydroxyphenylmethyloxycarbonyl.

In some certain embodiments, the peptide that can be cleaved by cathepsin B is represented by the following formula (III):

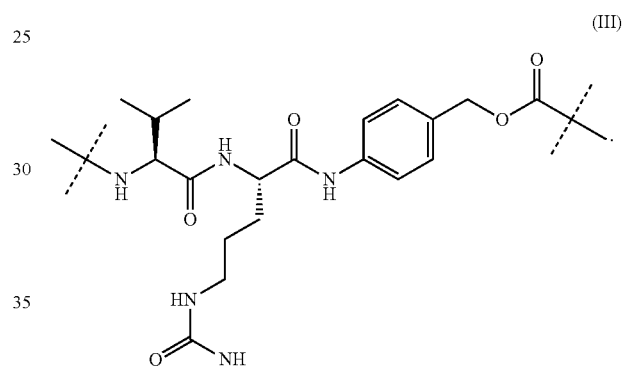
(III)

In some certain embodiments, the glucuronide that can be cleaved by β-glucuronidase is represented by the following formula (IV):

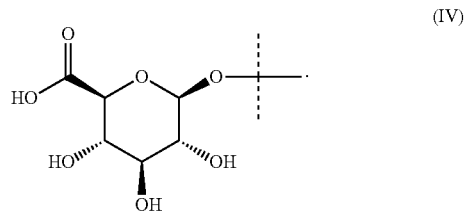
(IV)

3. Compositions

In still another aspect, the present invention provides compositions comprising a protein-active agent conjugate described herein. In embodiments, the compositions are used for delivering an active agent to a target cell in a subject. In embodiments, the compositions are used to treat a subject in need thereof (i.e., in need of the active agent).

The preparation of such compositions is known to one skilled in the art, and such compositions can be delivered in vivo to a subject.

In aspects, the compositions are prepared in an injectable form, either as a liquid solution or as a suspension. Solid forms suitable for injection may also be prepared as emulsions, or with the polypeptides encapsulated in liposomes.

The protein-active agent conjugates can be combined with a pharmaceutically acceptable carrier, which includes any carrier that does not induce the production of antibodies harmful to the subject receiving the carrier. Suitable carriers typically comprise large macromolecules that are slowly metabolized, such as proteins, polysaccharides, polylactic acids, polyglycolic acids, polymeric amino acids, amino acid copolymers, lipid aggregates, and the like. Such carriers are well known to those skilled in the art.

The compositions of the invention can also contain diluents, such as water, saline, glycerol, and ethanol. Auxiliary substances may also be present, such as wetting or emulsifying agents, pH buffering substances, and the like. Proteins may be formulated into the vaccine as neutral or salt forms. The compositions can be administered parenterally, by injection; such injection may be either subcutaneously or intramuscularly. Additional formulations are suitable for other forms of administration, such as by suppository or orally. Oral compositions may be administered as a solution, suspension, tablet, pill, capsule, or sustained release formulation.

The compositions are administered in a manner compatible with the dose formulation. The composition comprises a therapeutically effective amount of the protein-active agent conjugate. By a therapeutically effective amount is meant a single dose, or a composition administered in a multiple dose schedule, that is effective for the treatment or prevention of a disease or disorder. The dose administered will vary, depending on the subject to be treated, the subject's health and physical condition, the degree of protection desired, and other relevant factors. Precise amounts of the active ingredient required will depend on the judgment of the practitioner.

4. Methods of Using Protein-Active Agent Conjugates and Compositions

In a further aspect, the present invention provides a method for delivering an active agent to a target cell in a subject, the method comprising administering the protein-active agent conjugate or the composition. In a still further aspect, the present invention provides a method of treating a subject in need thereof (i.e., a subject in need of the active agent), the method comprising administering an effective amount of the protein-active agent conjugate or a composition comprising the conjugate to the subject.

In embodiments, a protein-active agent conjugate (e.g., antibody-drug conjugate) or a composition comprising the conjugate in a therapeutically effective amount can be administered to a patient suffering from a cancer or tumor to treat the cancer or tumor.

In embodiments, a protein-active agent conjugate (e.g., antibody-drug conjugate) or a composition comprising the conjugate in a therapeutically effective amount can be administered to a patient to treating or preventing an infection by a pathogenic agent (e.g., a virus, a bacteria, a fungus, a parasite, and the like). Such methods include the step of administering to the mammal a therapeutic or prophylactic amount of an amount of the conjugate sufficient to treat the disease or disorder or symptom thereof, under conditions such that the disease or disorder is prevented or treated.

In some embodiments, the protein-active agent conjugate or composition can be administered in the form of a pharmaceutically acceptable salt or solvate thereof. In some embodiments, it can be administered with a pharmaceutically acceptable carrier, a pharmaceutically acceptable excipient, and/or a pharmaceutically acceptable additive. The pharmaceutically effective amount and the type of the pharmaceutically acceptable salt or solvate, excipient and additive can be determined using standard methods (Remington's Pharmaceutical Sciences, Mack Publishing Co., Easton, Pa., 18$^{th}$ edition, 1990).

The term "therapeutically effective amount" with regard to a cancer or tumor means an amount that can decrease the number of cancer cells; decrease the size of cancer cells; prohibit cancer cells from intruding peripheral systems or decrease the intrusion; prohibit cancer cells from being spreading to other systems or decrease the spreading; prohibit cancer cells from growing; and/or ameliorate at least one symptoms related to the cancer. In the treatment of a cancer, the effectiveness of a drug can be assessed by time to tumor progression (TTP) and/or response rate (RR).

The term "therapeutically effective amount" with regard to infection by a pathogenic agent means an amount that can prevent, treat, or reduce the symptoms associated with infection.

The term "pharmaceutically acceptable salts" used herein includes organic salts and inorganic salts. Examples thereof include, but are not limited to, hydrochloride, hydrobromide, hydroiodide, sulfate, citrate, acetate, oxalate, chloride, bromide, iodide, nitrate, bisulfate, phosphate, acidic phosphate, isonicotinate, lactate, salicylate, acidic citrate, tartrate, oleate, tannate, pantonate, bitartrate, ascorbate, succinate, maleate, gentisinate, fumarate, gluconate, glucoronate, saccharate, formate, benzoate, glutamate, methane sulfonate, ethane sulfonate, benzene sulfonate, p-toluene sulfonate, and pamoate (i.e., 1,1'-methylenebis-(2-hydroxy-3-naphthoate)). A pharmaceutically acceptable salt can include another molecule (e.g., acetate ions, succinate ions, and other counter ions, etc.). It also can include at least one charged atom. It also can include at least one counter ion.

Exemplary solvates that can be used to pharmaceutical acceptable solvates of the compounds according to the present invention include, but not limited to, water, isopropanol, ethanol, methanol, DMSO, ethyl acetate, acetic acid, and ethanol amine.

EXAMPLES

The following examples illustrate the invention and are not intended to limit the same.

Example 1: Preparation of Ab(M)-CAAX 1-1. Construction, Expression, and Purification of Herceptin-CAAX Modified Herceptin antibodies were generated using standard recombinant DNA technology and PCR cloning protocols with pNATABH::Herceptin HC plasmid or pNAT-ABL::Herceptin LC plasmid. Recombinant plasmids were expressed in an HEK293E cell line by transient transfection. The antibodies were separated and purified by protein A column chromatography.

Construction of Herceptin-HC-GCVIM ("Herceptin-HC-GCVIM" disclosed as SEQ ID NO: 8) and Herceptin-LC-GCVIM ("Herceptin-LC-GCVIM" disclosed as SEQ ID NO: 11)

Modified Herceptin antibodies were generated using standard PCR cloning protocols. Generally, Herceptin-HC-GCVIM ("Herceptin-HC-GCVIM" disclosed as SEQ ID NO: 8) and Herceptin-LC-GCVIM ("Herceptin-LC-GCVIM" disclosed as SEQ ID NO: 11) plasmids were constructed by inserting a DNA sequence encoding a CAAX motif (e.g., GCVIM (SEQ ID NO: 1), $G_5$CVIM (SEQ ID NO: 2), $G_7$CVIM (SEQ ID NO: 3), $G_{10}$CVIM (SEQ ID NO: 4), or $G_{10}$CVLL (SEQ ID NO: 6)), to the C-terminus of the heavy chain or light chain encoded in the pNATABH::Herceptin HC or pNATABH::Herceptin LC plasmid.

For example, a SacII recognition sequence is present at amino acid 172 in the C-terminus of the human IgG1-Fc region. Accordingly, a forward primer was designed to bind the SacII site in the Fc region. The DNA sequence to be inserted (e.g., the 15-mer encoding GCVIM (SEQ ID NO: 1) 5-mer sequence) was added to a reverse primer specific for the Fc-C-terminal end. The forward and reverse primers were used to amplify a PCR product, and the resultant product was purified using a PCR purification kit. As the reverse primer contained an XhoI site, the PCR product was digested with SacII and XhoI. Likewise, the pNATABH:: Herceptin HC plasmid was digested with SacII and XhoI. The digested backbone was purified using a gel purification kit and ligated with the digested PCR product. Ligation was performed by appropriately adjusting the ratio of the vector and the insert, and the ligation product was transformed into competent bacterial cells for screening. Herceptin-HC-GC-VIM ("Herceptin-HC-GCVIM" disclosed as SEQ ID NO: 8) and Herceptin-LC-GCVIM ("Herceptin-LC-GCVIM" disclosed as SEQ ID NO: 11) plasmids were prepared from sequenced clones.

The amino acid sequences from the resultant plasmids are shown in FIGS. 1-10. Sections 1-4 and 1-7 below provide a detailed description of each of the constructs.

Expression and purification of Herceptin-HC-GCVIM ("Herceptin-HC-GCVIM" disclosed as SEQ ID NO: 8) and Herceptin-LC-GCVIM ("Herceptin-LC-GCVIM" disclosed as SEQ ID NO: 11)

HEK293E cells were cultured in DMEM/10% FBS media on 150 mm plates (#430599, Corning USA) until 70-80% confluency. 13 μg of DNA and 26 μg of PEI (#23966, Polysciences, USA) were mixed in a ratio of 1:2, incubated at RT for about 20 minutes, and then added to the HEK293E cells. After 16-20 hours, the media was replaced with serum free media (No FBS DMEM (# SH30243.01, Hyclone Thermo., USA)) and supernatant was collected every two or three days.

The supernatants were filtered with a 0.22 um top-filter (# PR02890, Millipore, USA) and then bound to 500 μl of protein A bead (#17-1279-03, GE healthcare Sweden) packed in a 5 mL column. Using a peristaltic pump, overnight binding was performed at 0.9 mL/min at 4° C. The column was washed with 100 mL or greater of PBS (#70011, Gibco, USA). Bound protein was then eluted with 0.1M Glycine-HCl (# G7126, Sigma, USA) into 6 fractions and neutralized with 1M Tris (# T-1503, Sigma, USA)(pH 9.0). The protein was quantified. 2 or 3 fractions containing the protein were collected and concentrated with Amicon Ultra filter units (# UFC805024, Millipore, USA). Buffer was changed about 10 times with 1×PBS (#70011, Gibco, USA). The protein product was confirmed to be Herceptin-HC-GCVIM ("Herceptin-HC-GCVIM" disclosed as SEQ ID NO: 8) or Herceptin)-LC-GCVIM ("Herceptin-LC-GCVIM" disclosed as SEQ ID NO: 11) by Western blot. To identify a protein band containing Herceptin, ImmunoPure peroxidase conjugated goat anti-human IgG Fc (#31413, Pierce, USA) was used. Upon purification, 1-2 mg of Herceptin-HC-CGVIM ("Herceptin-HC-GCVIM" disclosed as SEQ ID NO: 8) or Herceptin-LC-GCVIM ("Herceptin-LC-GCVIM" disclosed as SEQ ID NO: 11) was obtained from 1 L of cell culture medium.

The Herceptin-HC-GCVIM ("Herceptin-HC-GCVIM" disclosed as SEQ ID NO: 8) and Herceptin-LC-GCVIM ("Herceptin-LC-GCVIM" disclosed as SEQ ID NO: 11) products were also analyzed with an Agilent bioanalyzer. Briefly, 8 μl of purified protein sample (approx. 1 mg/ml) was analyzed using the Agilent Protein 230 Kit (5067-1515 Agilent Technologies, USA). The protein sample was separated into 2 fractions (4 μl each). 2 μl of non-reducing buffer or reducing buffer was added to each sample. The sample was heated at 95-100° C. for 5 minutes and cooled with ice to 4° C. After spin-down, 84 μl of deionized water was added to the sample and ladder and vortexed. Thereafter, the sample was loaded and analyzed with the kit per manufacturer's instructions.

1-2. Construction, Expression and Purification of Anti cMET-CAAX

Modified anti cMET-CAAX antibodies were also prepared by the above-described methods. For example, modified anti cMET-CAAX antibodies were generated using standard recombinant DNA technology and PCR cloning protocols with pPMC-C1A5 plasmid. Recombinant plasmids were expressed in an HEK293T cell line by transient transfection. The antibodies were separated and purified by protein A column chromatography.

1-3. Herceptin-HC-$G_n$CVIM ("$G_n$CVIM" Disclosed as SEQ ID NO: 5)

Herceptin-HC-GCVIM ("Herceptin-HC-GCVIM" disclosed as SEQ ID NO: 8), Herceptin-HC-$G_5$CVIM ("Herceptin-HC-$G_5$CVIM" disclosed as SEQ ID NO: 12), Herceptin-HC-$G_7$CVIM ("Herceptin-HC-$G_7$CVIM" disclosed as SEQ ID NO: 16), and Herceptin-HC-$G_{10}$CVIM ("Herceptin-HC-$G_{10}$CVIM" disclosed as SEQ ID NO: 20) antibodies were prepared. The antibodies, respectively, have a 5-mer(GCVIM) (SEQ ID NO: 1), a 9-mer($G_5$CVIM) (SEQ ID NO: 2), an 11-mer($G_7$CVIM) (SEQ ID NO: 3), or a 14-mer($G_{10}$CVIM) (SEQ ID NO: 4) sequence at the C-terminus of the heavy chain (FIGS. 1, 3, 5, and 7).

1-4. Herceptin-LC-$G_n$CVIM ("$G_n$CVIM" Disclosed as SEQ ID NO: 5)

Herceptin-LC-GCVIM ("Herceptin-LC-GCVIM" disclosed as SEQ ID NO: 11), Herceptin-LC-$G_5$CVIM ("Herceptin-LC-$G_5$CVIM" disclosed as SEQ ID NO: 15), Herceptin-LC-$G_7$CVIM ("Herceptin-LC-$G_7$CVIM" disclosed as SEQ ID NO: 19), and Herceptin-LC-$G_{10}$CVIM ("Herceptin-LC-$G_{10}$CVIM" disclosed as SEQ ID NO: 23) antibodies were prepared. The antibodies, respectively, have a 5-mer (GCVIM) (SEQ ID NO: 1), a 9-mer($G_5$CVIM) (SEQ ID NO: 2), an 11-mer($G_7$CVIM) (SEQ ID NO: 3), or a 14-mer($G_{10}$CVIM) (SEQ ID NO: 4) sequence at the C-terminus of the light chain (FIGS. 2, 4, 6, and 8).

1-5. Herceptin-HC-$G_{10}$CVLL ("Herceptin-HC-$G_{10}$CVLL" Disclosed as SEQ ID NO: 24)

A Herceptin-C-$G_{10}$CVLL ("Herceptin-HC-$G_{10}$CVLL" disclosed as SEQ ID NO: 24) antibody was prepared. The antibody has a 14-mer($G_{10}$CVLL) (SEQ ID NO: 6) sequence at the C-terminus of the heavy chain (FIG. 9).

1-6. Herceptin-LC-$G_{10}$CVLL ("Herceptin-LC-$G_{10}$CVLL" Disclosed as SEQ ID NO: 27)

A Herceptin-LC-$G_{10}$CVLL ("Herceptin-LC-$G_{10}$CVLL" disclosed as SEQ ID NO: 27) antibody was prepared. The antibody has a 14-mer($G_{10}$CVLL) (SEQ ID NO: 6) sequence at the C-terminus of the light chain (FIG. 10).

1-7. Anti cMET-HC-$G_n$CVIM ("$G_n$CVIM" Disclosed as SEQ ID NO: 5)

Anti cMET-HC-$G_7$CVIM ("$G_7$CVIM" disclosed as SEQ ID NO: 3) and anti cMET-HC-$G_{10}$CVIM ("$G_{10}$CVIM" disclosed as SEQ ID NO: 4) antibodies were prepared. The antibodies, respectively, have an 11-mer($G_7$CVIM) (SEQ ID NO: 3), or a 14-mer($G_{10}$CVIM) (SEQ ID NO: 4) sequence at the C-terminus of the heavy chain (not shown). FIG. 11 shows an SDS-PAGE gel analyzing the anti cMET-HC- G₇CVIM ("G₇CVIM" disclosed as SEQ ID NO: 3) and anti cMET-HC-G₁₀CVIM ("G₁₀CVIM" disclosed as SEQ ID NO: 4) antibodies.

1-8. Anti cMET-LC-G$_n$CVIM ("G$_n$CVIM" Disclosed as SEQ ID NO: 5)

Anti cMET-LC-G₇CVIM ("G₇CVIM" disclosed as SEQ ID NO: 3) and anti cMET-LC-G₁₀CVIM ("G₁₀CVIM" disclosed as SEQ ID NO: 4) antibodies were prepared. The antibodies, respectively, have an 11-mer(G₇CVIM) (SEQ ID NO: 3), or a 14-mer(G₁₀CVIM) (SEQ ID NO: 4) sequence at the C-terminus of the light chain (not shown). FIG. 11 shows an SDS-PAGE gel analyzing the anti cMET-LC-G₇CVIM ("G₇CVIM" disclosed as SEQ ID NO: 3) and anti cMET-LC-G₁₀CVIM ("G₁₀CVIM" disclosed as SEQ ID NO: 4) antibodies.

Example 2: Functionalization of AB(M)-CAAX 2-1. Geranyl Alkyne Diphosphate (B, LCB14-0501)

The above-referenced compound was prepared in 6 steps with geraniol as a starting material by a method similar to the method described in ChembioChem 207, 8, 98-105, the contents of which are hereby incorporated by reference in their entirety.

(B) ¹H NMR (600 MHz, D₂O) δ 5.38 (t, J=7.8 Hz, 1H), 5.30 (t, J=7.8 Hz, 1H), 4.31 (brs, 2H), 3.96 (m, 2H), 3.84 (s, 2H), 2.70 (bs, 1H), 2.07 (m, 2H), 1.98 (m, 2H), 1.56 (s, 3H), 1.48 (s, 3H)

2-2. Decadienyl Propargyl Ether Diphosphate (F, LCB14-0511) and Decadienyl Azide Diphosphate (G, LCB14-0512)

Acetoxydecadienyl aldehyde (C) was prepared from farnesol in 5 steps. From the compound (C), the compounds (D) and (E) were prepared in 6 steps and 5 steps, respectively. From the compounds (D) and (E), the above-referenced compounds (F) and (G) were prepared by a method similar to the method described in the section 2-1 above. The compounds (C), (D), and (E) were prepared by a method similar to the method described in JOC 2007, 72(24), 9291-9297, the contents of which are hereby incorporated by reference in their entirety.

(F): ¹H NMR (600 MHz, D₂O) δ 5.44 (t, J=6 Hz, 1H), 5.22 (t, J=6 Hz, 1H), 4.46 (t, J=8.4 Hz, 2H), 4.16 (t, J=2.4 Hz, 2H), 3.55 (m, 2H), 2.85 (m, 1H), 2.15 (m, 2H), 2.09 (t, J=7.2 Hz, 2H), 2.03 (t, J=7.2 Hz, 2H), 1.70~1.65 (m, 5H), 1.60 (s, 3H)

(G): ¹H NMR (600 MHz, D₂O) δ 5.43 (t, J=6.6 Hz, 1H), 5.23 (t, J=6.6 Hz, 1H), 4.40 (t, J=6 Hz, 2H), 3.26 (t, J=6.0 Hz, 2H), 2.15 (m, 2H), 2.10~2.04 (m, 4H), 1.70~1.65 (m, 5H), 1.60 (s, 3H)

2-3. NBD-GPP

Tris-ammonium[3,7-dimethyl-8-(7-nitro-benzo[1,2,5]oxadiazol-4-ylamino)-octa-2,6-diene-1]pyrophosphate (NBD-GPP) was prepared by a method similar to the method described in JACS 2006, 128, 2822-2835, the contents of which are hereby incorporated by reference in their entirety.

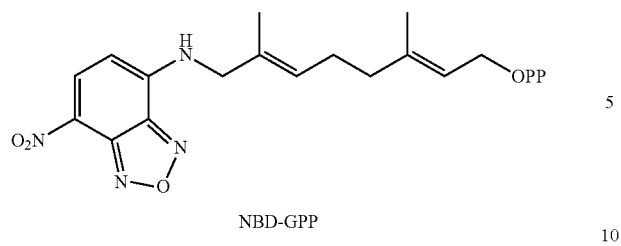
NBD-GPP
¹H NMR (600 MHz, D₂O) δ 8.51 (d, J=9 Hz, 1H), 6.37 (d, J=9 Hz, 1H), 5.50 (t, J=6.6 Hz, 1H), 5.42 (t, J=6.6 Hz, 1H), 4.43 (t, J=6.6 Hz, 2H), 4.08 (s, 2H), 2.22 (m, 2H), 2.10 (t, J=7.2 Hz, 2H), 1.69 (s, 6H)
2-4. Glucuronide Linker-MMAF (LCB14-0592)
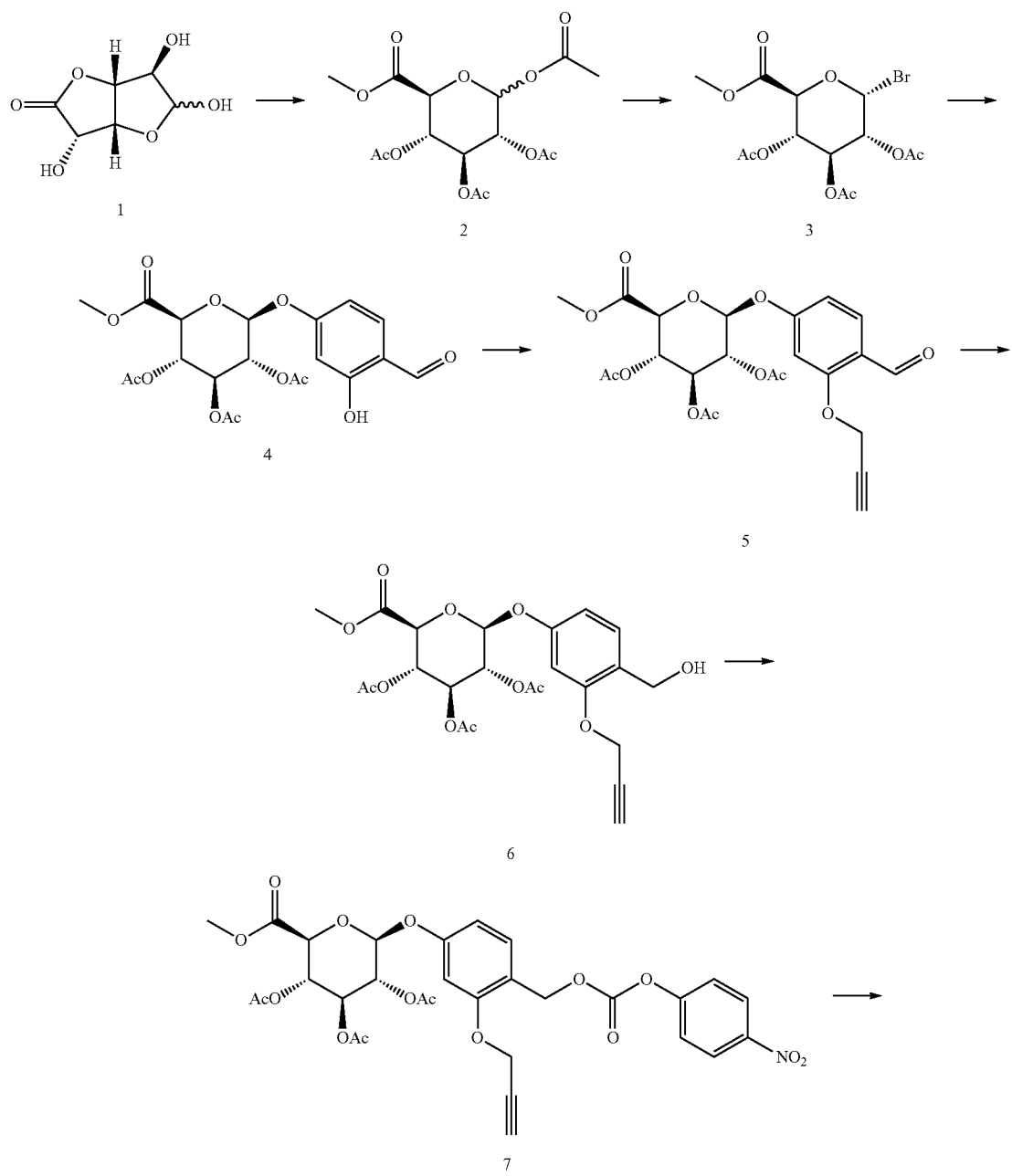

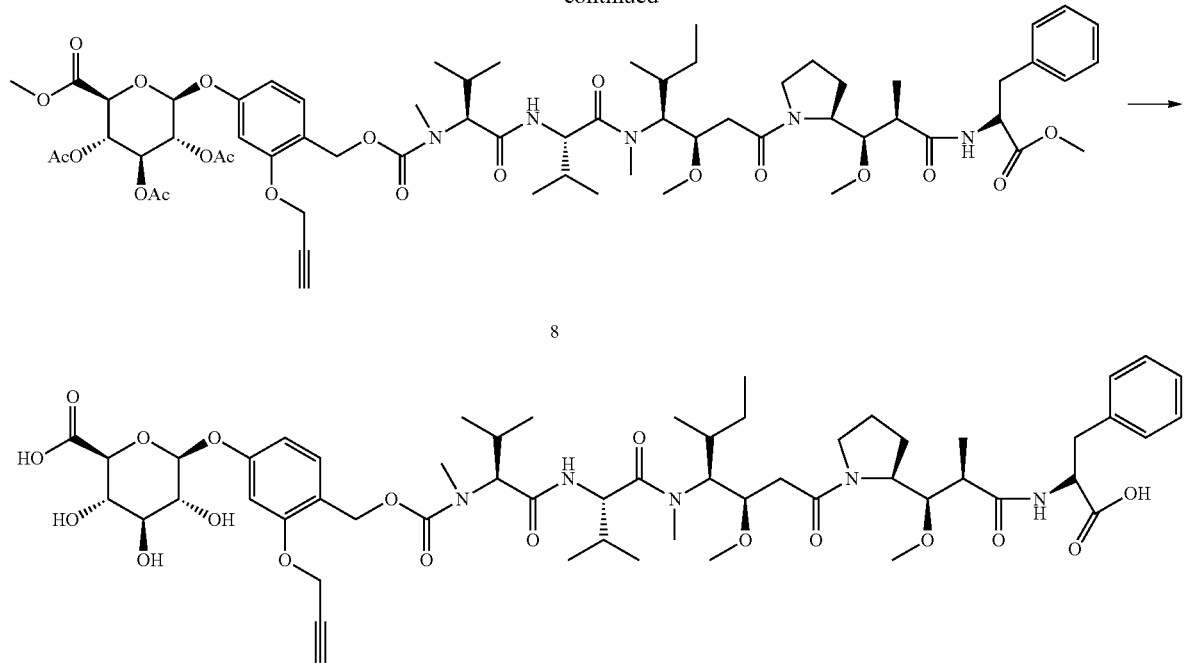

LCB14-0592

Compound 2

To a solution of D-glucurono-6,3-lactone (19 g, 107.88 mmol) in methanol (250 mL) under nitrogen atmosphere was slowly added a solution of NaOH (100 mg) in methanol (100 mL). The resulting mixture was stirred for 2 hours. A solution of NaOH (200 mg) in methanol (15 mL) was added. The resultant was stirred for 3 hours. Methanol was removed under reduced pressure. At 10° C. or lower, pyridine (50 mL) and acetic anhydride ($Ac_2O$, 54 mL) were sequentially added. The resulting mixture was stirred at room temperature for 4 hours. After the reaction was completed, the resulting mixture was concentrated under reduced pressure, and subjected to column chromatography to give the compound 2 (20 g, 50%) as a solid.

$^1$H NMR (600 MHz, $CDCl_3$) δ 5.77 (d, J=7.8 Hz, 1H), 5.31 (t, J=9.6 Hz, 1H), 5.24 (t, J=9.6 Hz, 1H), 5.14 (m, 1H), 4.17 (d, J=9 Hz, 1H), 3.74 (s, 3H), 2.12 (s, 3H), 2.04 (m, 9H)

Compound 3

The compound 2 (5 g, 13.28 mmol) was added to a solution of 33% HBr in AcOH (20 mL) at 0° C. The resulting mixture was stirred for 2 hours at room temperature. After the reaction was completed, the resulting mixture was diluted by toluene (50 mL). The resulting mixture was concentrated under reduced pressure. Ethyl acetate (100 mL) and saturated $NaHCO_3$ solution (100 mL) were added to extract an organic layer. The thus-obtained organic layer was dried with anhydrous sodium sulfate to give the compound 3 (5.27 g, 100%).

$^1$H NMR (600 MHz, $CDCl_3$) δ 6.64 (d, J=3.6 Hz, 1H), 5.61 (t, J=3.6 Hz, 1H), 5.24 (t, J=3.6 Hz, 1H), 4.85 (m, 1H), 4.58 (d, J=10.2 Hz, 1H), 3.76 (s, 3H), 2.10 (s, 3H), 2.06 (s, 3H), 2.05 (s, 3H)

Compound 4

A solution of the compound 3 (4 g, 10.07 mmol) and 2,4-dihydroxybenzaldehyde (1.67 g, 12.084 mmol) in acetonitrile (30 mL) was treated sequentially with molecular sieve (5 g) and $Ag_2O$ (9.33 g, 40.28 mmol). The resulting mixture was stirred for 3 hours at room temperature. After the reaction was completed, the solid was filtered off and the filtrate was concentrated under reduced pressure. The residue was subjected to column chromatography to give the compound 4 (2 g, 43.5%).

$^1$H NMR (400 MHz, $CDCl_3$) δ 11.38 (s, 1H), 9.77 (s, 1H), 7.48 (d, J=8.4 Hz, 1H), 6.61 (dd, J=8.4, 2.0 Hz, 1H), 6.53 (d, J=2.0 Hz, 1H), 5.36~5.25 (m, 4H), 4.23 (m, 1H), 3.73 (s, 1H), 2.06 (s, 9H)

Compound 5

A solution of the compound 4 (1 g, 2.20 mmol) in acetone (10 mL) was treated with potassium carbonate (760 mg, 5.50 mmol) and 80% propargyl bromide in toluene (735 μL, 6.60 mmol). The resulting mixture was stirred at 45° C. for 12 hours. After the reaction was completed, ethyl acetate (100 mL) and distilled water (100 mL) were added. The thus-obtained organic layer was dried with anhydrous sodium sulfate and concentrated under reduced pressure.

The residue was subjected to column chromatography to give the compound 5 (930 mg, 87%).

$^1$H NMR (600 MHz, $CDCl_3$) δ 10.33 (s, 1H), 7.83 (d, J=9 Hz, 1H), 6.75 (d, J=1.8 Hz, 1H), 6.67 (dd, J=9, 1.8 Hz, 1H), 5.39~5.34 (m, 2H), 5.31~5.26 (m, 2H), 4.79 (d, J=2.4 Hz, 2H), 4.23 (m, 2H), 3.72 (s, 3H), 2.59 (t, J=2.4 Hz, 1H), 2.07 (s, 3H), 2.06 (s, 3H), 2.05 (s, 3H)

Compound 6

A solution of the compound 5 (930 mg, 1.88 mmol) in isopropyl alcohol (2 mL) and chloroform (10 mL) at 0° C. was treated sequentially with silica-gel (5 g) and $NaBH_4$ (178 mg, 4.79 mmol). The resulting mixture was stirred for 3 hours. After the reaction was completed, silica gel was filtered off. The reaction was extracted with dichloromethane (100 mL) and distilled water (100 mL), dried with anhydrous sodium sulfate and concentrated in vacuo. The residue was subjected to column chromatography to give the compound 6 (610 mg, 65%).

¹H NMR (600 MHz, CDCl₃) δ 7.23 (d, J=8.4 Hz, 1H), 6.72 (d, J=2.4 Hz, 1H), 6.61 (dd, 8.4, 2.4 Hz, 1H), 5.35~5.32 (m, 2H), 5.27 (m, 1H), 5.13 (d, J=7.8 Hz, 1H), 4.72 (d, J=2.4 Hz, 2H), 4.63 (d, J=5.4 Hz, 2H), 4.17 (m, 1H), 3.73 (s, 3H), 2.07 (s, 3H), 2.05 (s, 3H), 2.04 (s, 3H)

Compound 7

A solution of the compound 6 (250 mg, 0.50 mmol) in dimethylformamide (0.5 mL) was treated with bis(4-nitrophenyl)carbonate (308 mg, 100 mmol) and diisopropylethylamine (DIPEA, 132 μL, 0.75 mmol). The resulting mixture was stirred at room temperature for 3 hours. After the reaction was completed, the reaction was concentrated under reduced pressure. The residue was subjected to column chromatography to give the compound 7 (310 mg, 94%).

¹H NMR (600 MHz, CDCl₃) δ 8.26 (d, J=9 Hz, 2H), 7.37 (d, J=9 Hz, 2H), 7.34 (d, J=8.4 Hz, 1H), 6.77 (d, J=1.8 Hz, 1H), 6.64 (dd, 7.8, 2.4 Hz, 1H), 5.37~5.33 (m, 2H), 5.30~5.27 (m, 3H), 5.17 (d, J=7.2 Hz, 1H), 4.74 (d, J=2.4 Hz, 2H), 4.18 (m, 1H), 3.74 (s, 3H), 2.54 (t, J=2.4 Hz, 1H), 2.07 (s, 3H), 2.05 (s, 3H), 2.04 (s, 3H)

Compound 8

To a solution of the compound 7 (150 mg, 0.227 mmol), MMAF-OMe (169.6 mg, 0.227 mmol), and 1-hydroxybenzotriazole anhydrous (HOBt, 6.2 mg, 0.0454 mmol) in dimethylformamide (3 mL) were added pyridine (0.8 mL) and diisopropylethylamine (40 μL, 0.227 mmol). The resulting mixture was stirred at room temperature for 12 hours. After the reaction was completed, ethyl acetate (100 mL) and distilled water (100 mL) were added. The thus-obtained organic layer was dried with anhydrous sodium sulfate and concentrated under reduced pressure. The residue was subjected to column chromatography to give the compound 8 (146 mg, 50%).

EI-MS m/z: 1067 (M⁺)

MMAF-OMe was prepared according to the methods described in U.S. 61/483,698, ChemPharmBull, 1995, 43(10), 1706-1718, U.S. Pat. Nos. 7,423,116, 7,498,298, and WO2002/088172, the contents of each of these references are hereby incorporated by reference in their entirety.

LCB14-0592

A solution of the compound 8 (85 mg, 0.067 mmol) in methanol (2 mL) was treated at 0° C. with a solution of LiBH₄ (28.2 mg, 0.670 mmol) in distilled water (1 mL). The resulting mixture was stirred at room temperature for 3 hours. After the reaction was completed, methanol was removed under reduced pressure. The residue was dissolved in distilled water (50 mL) and acidified with acetic acid to pH=3. The reaction was extracted three times with dichloromethane (3×50 mL). The combined organic layer was concentrated under reduced pressure to give a solid which was washed with diethyl ether (50 mL) to yield the compound LCB14-0592 (62 mg, 83%).

EI-MS m/z: 1112(M⁺)

2-5. Glucuronide Linker-MMAE (LCB14-0598)

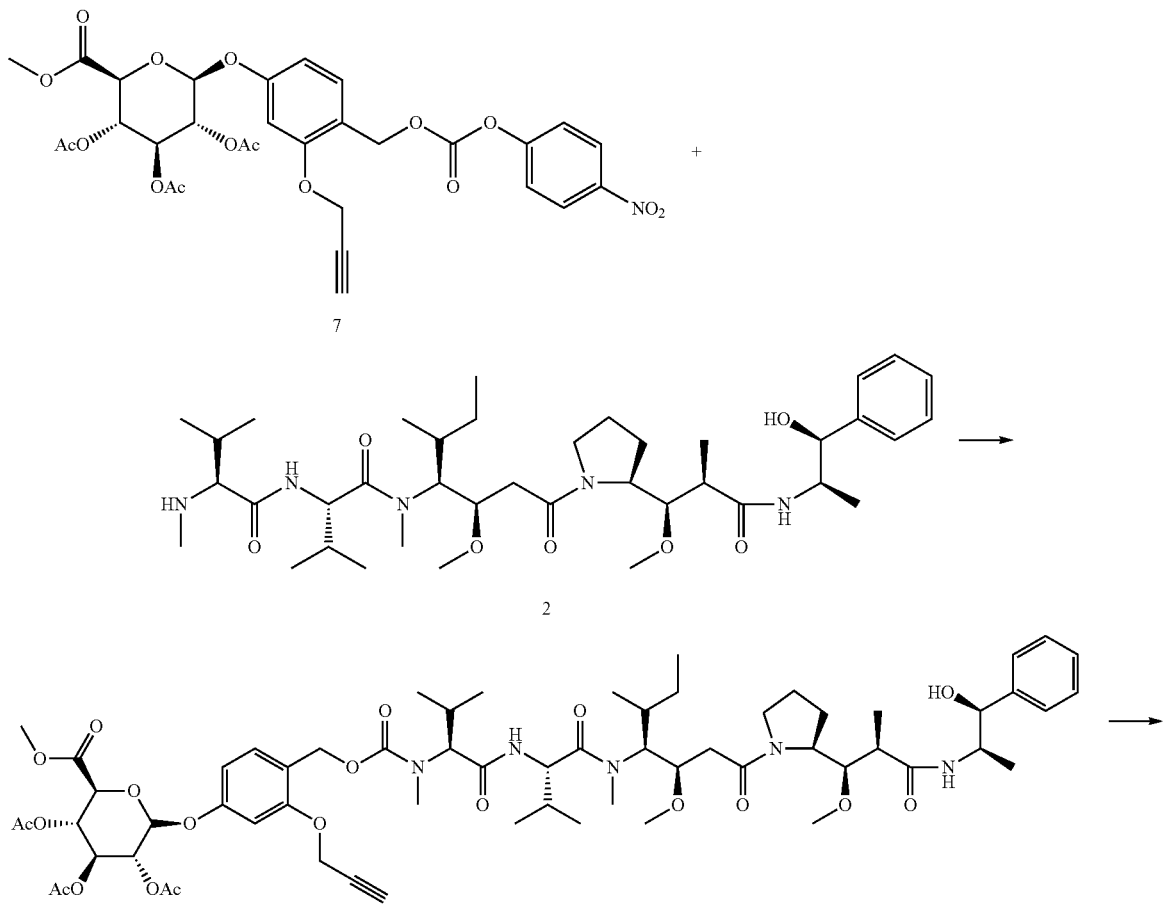

-continued

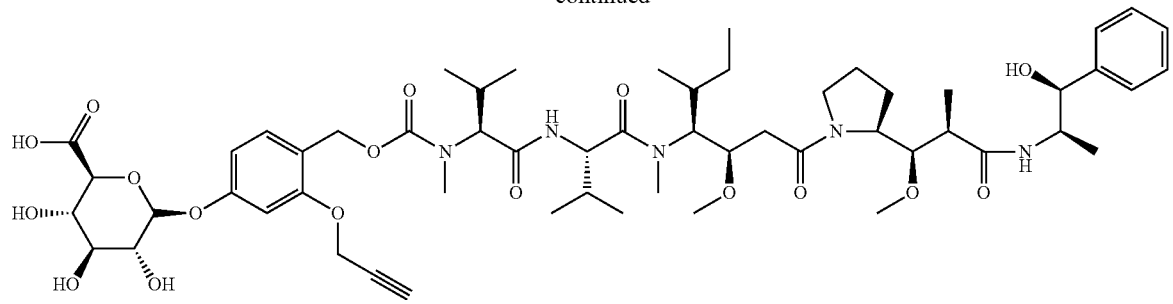

LCB14-0598

Compound 3

A solution of the compound 7 of Example 2-4 (150 mg, 0.227 mmol), MMAE (163 mg, 0.227 mmol; ChemPharm-Bull, 1995, 43(10), 1706-1718, U.S. Pat. No. 7,423,116, WO2002/088172), and anhydrous 1-hydroxybenzotriazole (HOBt, 6.2 mg, 0.0454 mmol) in dimethylformamide (3 mL) was treated with pyridine (0.8 mL) and diisopropylethylamine (40 μL, 0.227 mmol). The resulting mixture was stirred at room temperature for 24 hours. After the reaction was completed, the resulting mixture was diluted with ethyl acetate (100 mL), 0.5N HCl (10 mL), and distilled water (100 mL). The thus-obtained organic layer was dried with anhydrous sodium sulfate and concentrated under reduced pressure. The residue was subjected to column chromatography to give the compound 3 (30 mg, 10%).

EI-MS m/z: 1238(M$^+$)

LCB14-0598

A solution of the compound 3 (30 mg, 0.024 mmol) in methanol (3 mL) was treated at 0° C. with LiOH (10 mg, 0.24 mmol) in distilled water (0.5 mL). The resulting mixture was stirred for 3 hours at room temperature. After the reaction was completed, the organic solvent was removed under reduced pressure. The resulting product was diluted with distilled water (50 mL) and acidified with 0.5N HCl to pH=3. Extraction with dichloromethane (50 mL) followed by concentration under reduced pressure gave the compound LCB14-0598 (21 mg, 79%).

EI-MS m/z: 1098(M$^+$)

2-6. Glucuronide Linker-MMAF-Methyl Amide (LCB14-0600)

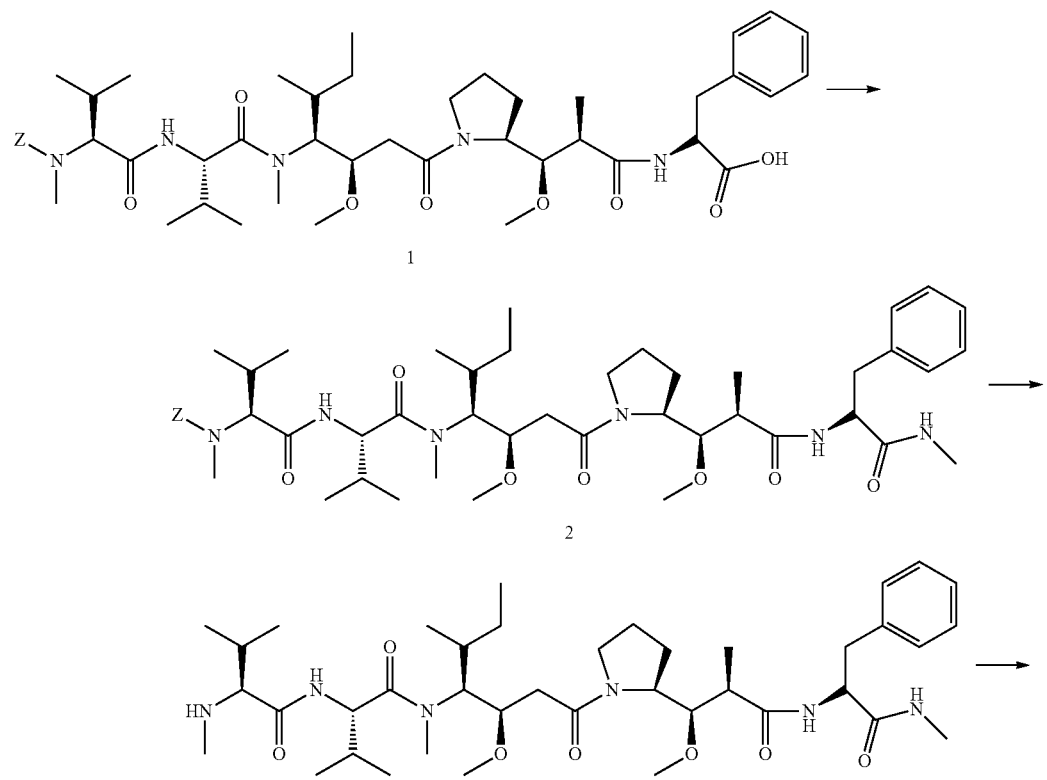

LCB14-0601

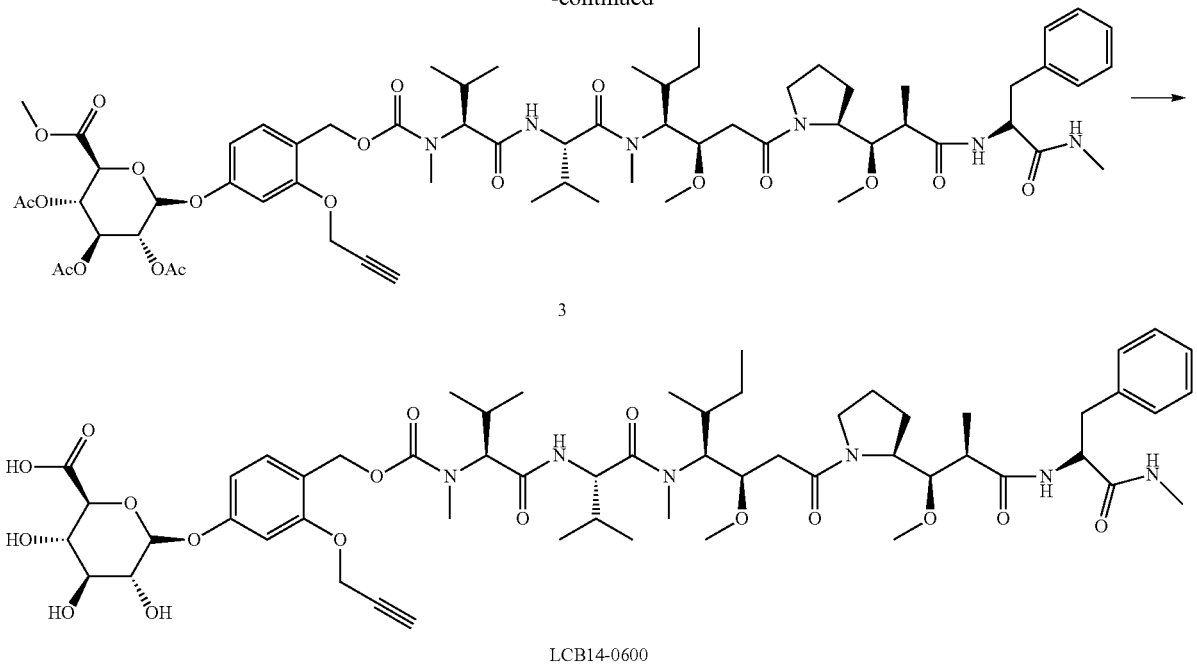

LCB14-0600

Compound 2

A solution of the compound 1 (Z-MMAF, 558 mg, 0.644 mmol, ChemPharmBull, 1995, 43(10), 1706-1718) in dimethylformamide (5 mL) was treated with methylamine hydrochloride (130 mg, 1.932 mmol), diethylcyanophosphonate (DEPC, 144 mg, 0.966 mmol), and triethylamine (270 μL, 1.932 mmol). The resulting mixture was stirred at room temperature for 12 hours. After the reaction was completed, ethyl acetate (100 mL) and distilled water (100 mL) were added. The thus-obtained organic layer was dried with anhydrous sodium sulfate and concentrated under reduced pressure. The residue was subjected to column chromatography to give the compound 2 (490 mg, 86%).

EI-MS m/z: 879(M$^+$)

LCB14-0601 (MMAF-Methyl Amide)

The compound 2 (470 mg, 0.53 mM) was dissolved in tert-butanol (t-BuOH, 8 mL) and distilled water (0.8 mL). At 0° C., 10% Pd/C (50 mg) was added. The resulting mixture was stirred in H$_2$ gas for 2 hours. After the reaction was completed, the Pd/C was filtered using celite. The resulting filtered solution was concentrated under reduced pressure to give the compound LCB14-0601 (340 mg, 85%).

EI-MS m/z: 745(M$^+$)

Compound 3

A solution of the compound 7 of Example 2-4 (133 mg, 0.20 mmol), LCB14-601 (150 mg, 0.20 mmol), and anhydrous 1-hydroxybenzotriazole (HOBt, 5.44 mg, 0.04 mmol) in dimethylamide (3 mL) was treated with pyridine (0.8 mL) and diisopropylethylamine (DIPEA, 35 μL, 0.20 mmol). The resulting mixture was stirred at room temperature for 12 hours. After the reaction was completed, ethyl acetate (100 mL) and 0.5N HCl solution (50 mL) were added. The thus-obtained organic layer was dried with anhydrous sodium sulfate and concentrated under reduced pressure. The residue was subjected to column chromatography to give the compound 3 (123 mg, 48%).

EI-MS m/z: 1265(M$^+$)

LCB14-0600 (Glucuronide Linker-MMAF-Methyl Amide)

A solution of the compound 3 (60 mg, 0.047 mmol) in methanol (3 mL) was treated at 0° C. with LiOH (20 mg, 0.47 mmol) in distilled water (0.5 mL). The resulting mixture was stirred at room temperature for 2 hours. After the reaction was completed, the organic solvent was removed under reduced pressure. The residue was diluted with distilled water (50 mL) and acidified with 0.5N HCl to pH=3. Extraction with dichloromethane (50 mL) followed by concentration gave the compound LCB14-0600 (25 mg, 47%).

EI-MS m/z: 1125(M$^+$)

2-7. Azide-Linker-NBD: LCB14-0529

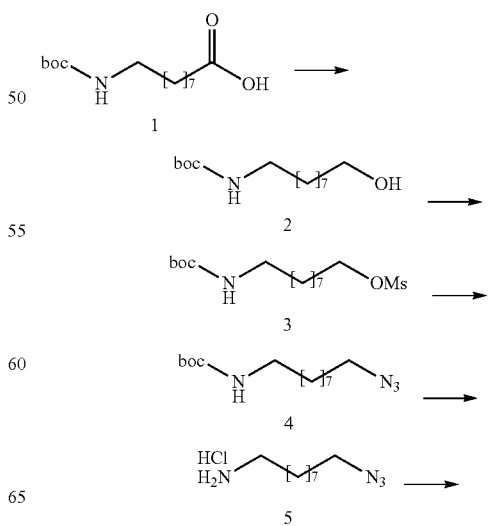

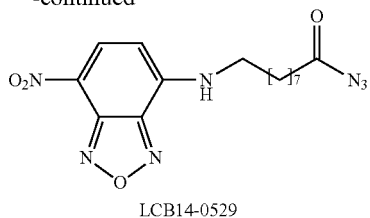

LCB14-0529

Compound 2

A solution of the compound 1 (4 g, 12.67 mmol) and N-methylmorpholine (1.6 mL, 14.57 mmol) in tetrahydrofuran (30 mL) was treated slowly with isobutylchloroformate (1.8 mL, 13.94 mmol) under nitrogen atmosphere at −15° C. The resulting mixture was stirred at the same temperature for 30 minutes. The resulting mixture was filter-added slowly to a solution of sodium borohydride (959 mg, 25.34 mmol) in tetrahydrofuran/methanol (36 mL/12 mL) at −78° C. with efficient stirring. The reactant was slowly warmed up to room temperature while being stirred for 2 hours. After the reaction was completed, acetic acid (4 mL) was added and stirred for 15 minutes. Ethyl acetate (100 mL) and distilled water (100 mL) were added. The thus-obtained organic layer was dried with anhydrous sodium sulfate and concentrated under reduced pressure. The residue was subjected to column chromatography to give the compound 2 (3.69 g, 96.5%).

$^1$H NMR (600 MHz, CDCl$_3$) δ 4.50 (s, 1H), 3.64 (q, J=6.6 Hz, 2H), 3.11 (m, 2H), 1.56 (m, 2H), 1.44 (m, 11H), 1.29 (m, 10H)

Compound 3

A solution of the compound 2 (450 mg, 1.73 mmol) and N-methylmorpholine (381 μL, 3.46 mmol) in tetrahydrofuran (5 mL) was treated slowly with methanesulfonic anhydride (363 mg, 2.07 mmol) under nitrogen atmosphere at 0° C. The resulting mixture was slowly warmed up to room temperature while being stirred for 1 hour. After the reaction was completed, ethyl acetate (50 mL) and distilled water (50 mL) were added. The thus-obtained organic layer was dried with anhydrous sodium sulfate and concentrated under reduced pressure. The residue was subjected to column chromatography to give the compound 3 as a white solid (520 mg, 89%).

$^1$H NMR (600 MHz, CDCl$_3$) δ 4.50 (s, 1H), 4.22 (t, J=6.6 Hz, 2H), 3.11 (m, 2H), 3.01 (s, 3H), 1.74 (m, 2H), 1.44-1.36 (m, 13H), 1.29 (m, 8H)

Compound 4

A solution of the compound 3 (520 mg, 1.54 mmol) in dimethylformamide (5 mL) was treated with sodium azide (120 mg, 1.85 mmol) under nitrogen atmosphere and the resulting mixture was stirred at 70° C. for 3 hours. After the reaction was completed, ethyl acetate (50 mL) and distilled water (50 mL) were added. The thus-obtained organic layer was dried with anhydrous sodium sulfate and concentrated under reduced pressure to give the compound 4 in liquid form (430 mg, 98%).

$^1$H NMR (600 MHz, CDCl$_3$) δ 4.49 (s, 1H), 3.26 (t, J=6.9 Hz, 2H), 3.09-3.12 (m, 2H), 1.59 (m, 2H), 1.44 (m, 11H), 1.33 (m, 10H)

Compound 5

A solution of the compound 4 (430 mg, 1.51 mmol) in dichloromethane (6 mL) was treated with 4M-HCl in 1,4-dioxane (4 mL) under nitrogen atmosphere at 0° C. The resulting mixture was stirred for 3 hours and concentrated under reduced pressure to give the compound 5 (330 mg, 99%).

$^1$H NMR (600 MHz, CDCl$_3$) δ 8.29 (s, 2H), 3.26 (t, J=6.9 Hz, 2H), 2.98 (m, 2H), 1.46 (m, 2H), 1.59 (m, 2H), 1.31-1.39 (m, 10H)

LCB14-0529

A solution of the compound 5 (326 mg, 1.47 mmol) in a mixture solvent (10 mL) of acetonitrile and 25 mmol sodium bicarbonate was treated with 4-chloro-7-nitrobenzofurazan (442 mg, 2.20 mmol). The resulting mixture was stirred for 3 hours at room temperature. Ethyl acetate (50 mL) and distilled water (50 mL) were added. The thus-obtained organic layer was dried with anhydrous sodium sulfate and concentrated under reduced pressure. The residue was subjected to column chromatography to give the compound LCB14-0529 (250 mg, 49%).

$^1$H NMR (600 MHz, CDCl$_3$) δ 8.48 (d, J=8.4 Hz, 1H), 6.16 (d, 8.4 Hz, 1H), 3.47 (q, 6.6 Hz, 2H), 3.24 (t, 6.9 Hz, 2H), 1.79 (m, 2H), 1.59 (m, 2H), 1.42-1.48 (m, 2H), 1.20-1.37 (m, 8H)

2-8. Azide-Linker-NBD: LCB14-0530

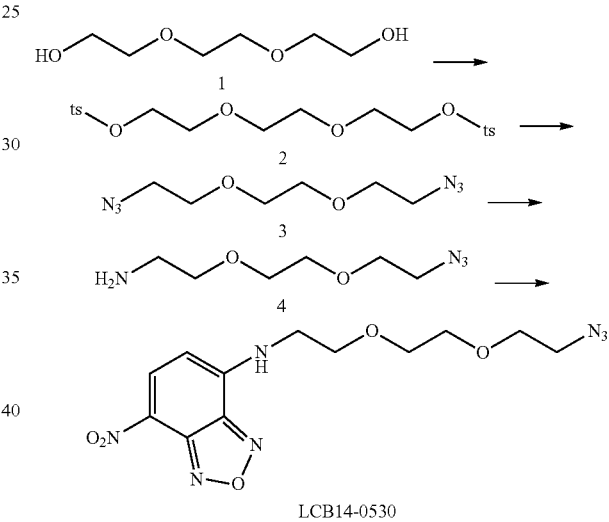

LCB14-0530

Compound 2

A solution of tri(ethylene)glycol (5 g, 33.29 mmol) in dichloromethane (30 mL) was treated with p-toluenesulfonyl chloride (13.96 g, 73.24 mmol) and potassium hydroxide (8.96 g, 159.79 mmol) under nitrogen atmosphere at 0° C. The resulting mixture was stirred for 3 hours at 0° C. Ethyl acetate (100 mL) and distilled water (100 mL) were added. The thus-obtained organic layer was dried with anhydrous sodium sulfate and concentrated under reduced pressure. The residue was subjected to column chromatography to give the compound 2 (13.2 g, 86.5%) as a white solid.

$^1$H NMR (600 MHz, CDCl$_3$) δ 7.79 (m, 4H), 7.35 (m, 4H), 4.14 (m, 4H), 3.65 (m, 4H), 3.53 (s, 4H), 2.44 (s, 6H)

Compound 3

A solution of the compound 2 (4.5 g, 9.81 mmol) in dimethylformamide (20 mL) was treated with sodium azide (1.6 g, 24.52 mmol) under nitrogen atmosphere. The resulting mixture was stirred at 65° C. for 10 hours. Ethyl acetate (100 mL) and distilled water (100 mL) were added. The thus-obtained organic layer was dried with anhydrous sodium sulfate and concentrated under reduced pressure.

The residue was subjected to column chromatography to give the compound 3 (1.96 g, 99%).

$^1$H NMR (600 MHz, CDCl$_3$) δ 3.68-3.66 (m, 8H), 3.37 (t, J=4.8 Hz, 4H)

Compound 4

A solution of the compound 3 (500 mg, 2.49 mmol) in 6.6 mL of a mixed solvent of diethyl ether, tetrahydrofuran, and 1N HCl (V:V:V=3:0.6:3). A solution of triphenylphosphine (655 mg, 2.49 mmol) in diethyl ether (3.5 mL) was slowly added over 5 minutes. The resulting mixture was stirred at room temperature for 5 hours. The resulting mixture was diluted with ethyl acetate (50 mL) and distilled water (50 mL) and neutralized with 1N NaOH solution. The thus-obtained organic layer was dried with anhydrous sodium sulfate and concentrated under reduced pressure. The residue was subjected to column chromatography to give the compound 4 (370 mg, 85%).

$^1$H NMR (600 MHz, CDCl$_3$) δ 3.69-3.63 (m, 6H), 3.52 (t, J=5.1 Hz, 2H), 3.40 (t, J=4.8 Hz, 2H), 2.87 (t, J=5.1 Hz, 2H)

LCB14-0530

A solution of the compound 4 (200 mg, 1.14 mmol) in tetrahydrofuran (4 mL) was treated sequentially with triethylamine (320 μL, 2.28 mmol) and a solution of 4-chloro-7-nitrobenzofurazan (442 mg, 2.20 mmol) in tetrahydrofuran (1 mL). The resulting mixture was stirred at room temperature for 1 hour. Ethyl acetate (50 mL) and distilled water (50 mL) were added. The thus-obtained organic layer was dried with anhydrous sodium sulfate and concentrated under reduced pressure. The residue was subjected to column chromatography to give the compound LCB14-0530 (305 mg, 78.8%).

$^1$H NMR (600 MHz, CDCl$_3$) δ 8.47 (d, J=8.4 Hz, 1H), 6.75 (s, 1H), 6.17 (d, J=8.4 Hz, 1H), 3.86 (t, J=4.8 Hz, 2H), 3.66-3.73 (m, 8H), 3.41 (t, J=4.8 Hz, 2H)

2-9. Azide-Linker-Drug: LCB14-0505, -0531, and -0510

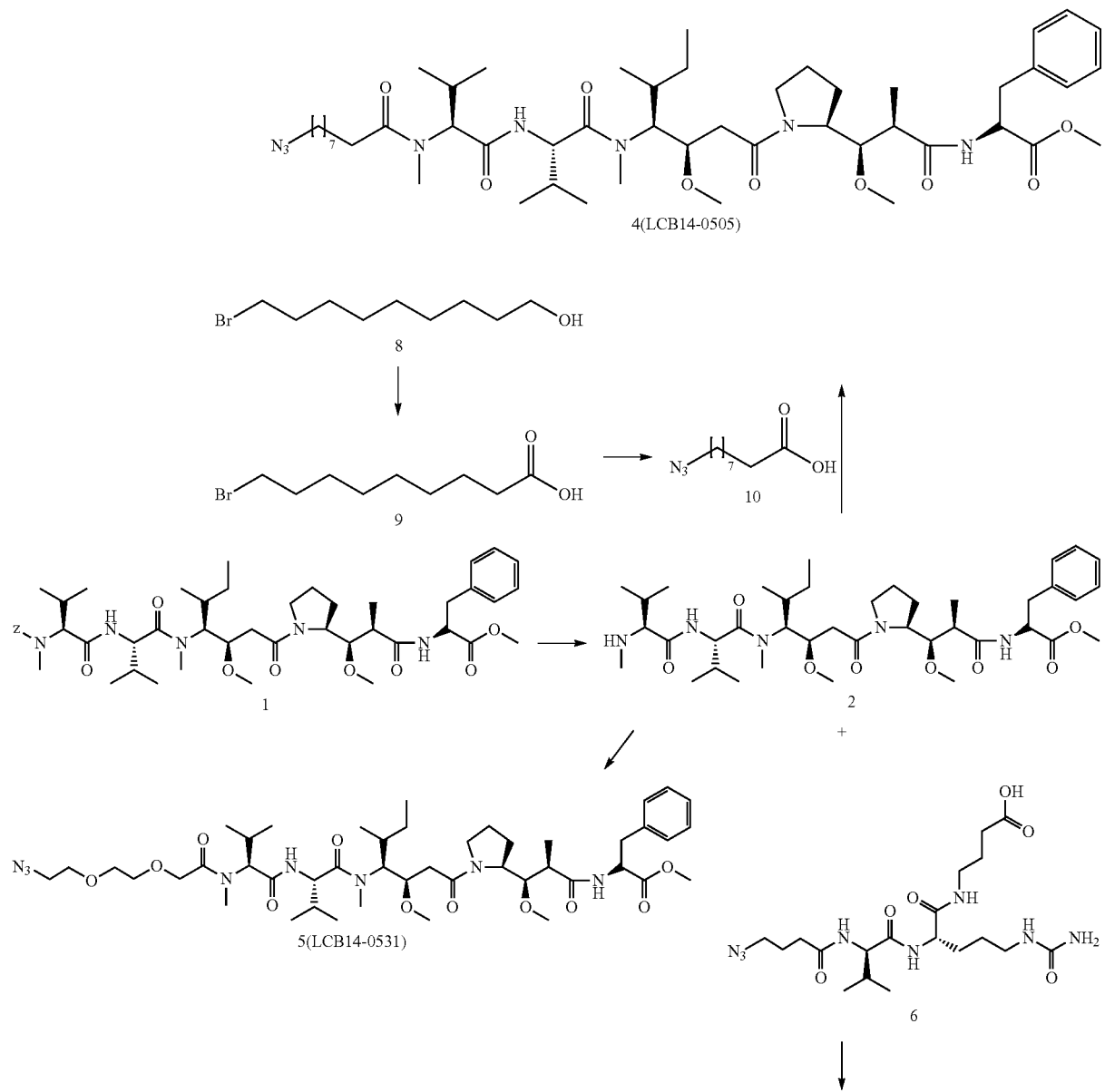

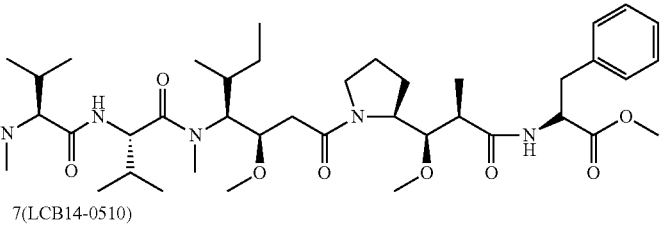

7(LCB14-0510)

Compound 2

The compound 1 was prepared with reference to the method described in ChemPharmBull, 1995, 43(10), 1706-1718, the contents of which are hereby incorporated by reference in their entirety. A solution of the compound 1 (0.50 g, 0.57 mmol) in tert-butanol (6 mL) and water (0.6 mL) was stirred for 4 hours under hydrogen atmosphere with Pd/C (6 mg, 0.06 mmol). The reactant solution was filtered through a celite pad and the filtrate was concentrated under reduced pressure to give the compound 2 (0.42 g) as a white solid.

EI-MS m/z: 747(M+)

Compound 9

Chromium(VI) trioxide ($CrO_3$, 7 g, 0.07 mol) was dissolved in distilled water (10 mL) at 0° C. To the solution was added sequentially 18M-$H_2SO_4$ (6.1 mL, 0.11 mol) and distilled water (20 mL). The resulting mixture was stirred for 5 minutes (=Jones reagent). A solution of 9-bromo-1-nonanol (5 g, 22.4 mmol) in acetone (250 mL) was treated slowly with the Jones reagent (18 mL) at −5° C. After stirring the resulting mixture for 3 hours at room temperature, the greenish solid was filtered off and the filtrate was concentrated. The residue was extracted with diethyl ether (100 mL) and water (50 mL). The organic extract was dried with anhydrous $Na_2SO_4$, filtered and concentrated in vacuo. The residue was subjected to flash column chromatography to give the compound 9 (4.95 g, 93%).

$^1$H NMR (600 MHz, $CDCl_3$) δ 3.40 (t, J=6.6 Hz, 2H), 2.35 (t, J=7.2 Hz, 2H), 1.85 (m, 2H), 1.62 (m, 2H), 1.41 (m, 2H), 1.32 (m, 6H)

Compound 10

A solution of the compound 9 (4 g, 16.86 mmol) in N,N-dimethylformamide (15 mL) was treated with sodium azide (1.64 g, 25.29 mmol). The resulting mixture was heated to 80° C. for 6 hours with stirring. After the reaction was complete, ethyl acetate (100 mL) and distilled water (100 mL) were added. The thus-obtained organic layer was separated, dried with anhydrous $Na_2SO_4$, filtered and concentrated in vacuo. The residue was subjected to flash column chromatography to give the compound 10 (3.3 g, 98%).

$^1$H NMR (600 MHz, $CDCl_3$) δ 3.26 (t, J=7.2 Hz, 2H), 2.35 (t, J=7.2 Hz, 2H), 1.64~1.57 (m, 4H), 1.35~1.32 (m, 8H)

LCB14-0505

A solution of the compound 2 (0.16 g, 0.21 mmol) and the 9-azido-nonanoic acid (10) (47 mg, 0.24 mmol) in methylene chloride (3 mL) was treated with DIPEA (0.06 mL, 0.32 mmol) and PyBOP (0.15 g, 0.28 mmol) at 0° C. The resulting mixture was stirred for 3 hours. The resulting mixture was extracted with methylene chloride (100 mL) and water (20 mL). The thus-obtained organic layer was concentrated under reduced pressure. The residue was subjected to column chromatography with ethyl acetate and hexane to give the compound LCB14-0505 (0.12 g, 59%) as a white solid.

EI-MS m/z: 928(M+)

LCB14-0531

The compound LCB14-0531 (65%) was prepared in a similar method to the above-described method.

EI-MS m/z: 917(M+)

LCB14-0510

The compound 6 was prepared using the methods described in BioconjugateChem. 2002, 13, 855-869 and US2005238649, the contents of each of these references are hereby incorporated by reference in their entirety. A solution of the compound 6 (69 mg, 0.15 mmol) and compound 2 (100 mg, 0.13 mmol) in DMF (2 mL) was treated with DIPEA (0.04 mL, 0.2 mmol) and PyBOP (0.09 g, 0.17 mmol) at 0° C. The resulting mixture was stirred for 3 hours. Ethyl acetate (100 mL) and water (30 mL) were used to extract an organic layer, which was concentrated under reduced pressure. The residue was subjected to column chromatography with methylene chloride and methanol to give the compound LCB14-0510 (94 mg, 64%) as a brown solid.

EI-MS m/z: 1199(M+)

2-10. Acetylene-Linker-NBD: LCB14-0532

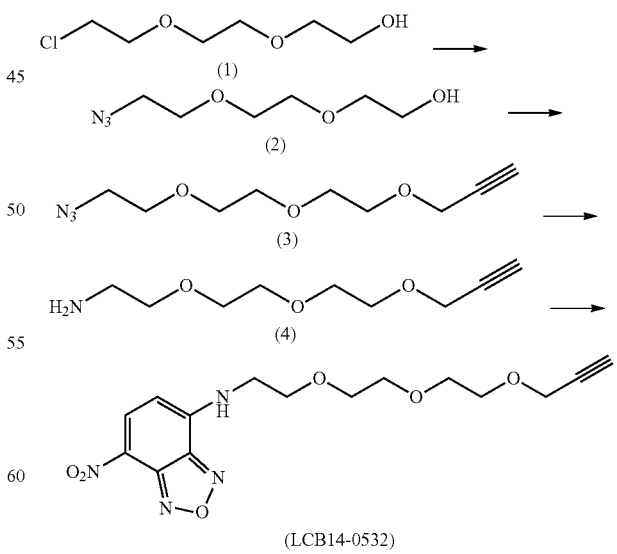

(LCB14-0532)

Compound 2

A solution of the compound 1 (1 g, 5.93 mmol) in 10 mL of dimethylformamide was treated with sodium azide (578 mg, 8.89 mmol) under nitrogen atmosphere. The resulting mixture was stirred at 80° C. for 3 hours. After the reaction was completed, ethyl acetate (50 mL) and distilled water (50 mL) were added. The thus-obtained organic layer was dried with anhydrous sodium sulfate and concentrated under reduced pressure to give the compound 2 (1.03 g, 99%).

$^1$H NMR (600 MHz, CDCl$_3$) δ 3.75 (m, 2H), 3.69 (m, 6H), 3.62 (m, 2H), 3.41 (t, J=3.5 Hz, 2H), 2.30 (m, 1H)

Compound 3

To a suspension of sodium hydride (55% in mineral oil, 250 mg, 5.7 mmol) in tetrahydrofuran (10 mL) at 0° C. was added a solution of the compound 2 (500 mg, 2.85 mmol) in tetrahydrofuran (5 mL). The resulting mixture was stirred for 1 hour. The resulting mixture was then warmed up to room temperature and stirred for 2 hours. Propargyl bromide (80% in toluene, 800 μl, 7.12 mmol) was added and the resulting mixture was stirred at room temperature for 12 hours. Ammonium chloride solution (20 mL) and diethyl ether (30 mL) were added. The thus-obtained organic layer was dried with anhydrous sodium sulfate and concentrated under reduced pressure to give the compound 3 (530 mg, 86.6%).

$^1$H NMR (600 MHz, CDCl$_3$) δ 4.21 (d, J=2.4 Hz, 2H), 3.66-3.72 (m, 10H), 3.39 (t, J=5.1 Hz, 2H), 2.43 (t, J=2.4 Hz, 1H)

Compound 4

A solution of the compound 3 (250 mg, 1.17 mmol) in 3 mL of a mixture solution of tetrahydrofuran and distilled water (V:V=2:1) was treated slowly with triphenyl phosphine (461 mg, 1.75 mmol) in tetrahydrofuran (1 mL) over 5 minutes. The resulting mixture was stirred at room temperature. After the reaction was completed, diethyl ether (30 mL) and distilled water (30 mL) were added. The resulting mixture was acidified with 1N HCl, and the organic layer was separated off. The aqueous layer was diluted with dichloromethane (50 mL) and neutralized with 1N NaOH solution. The thus-obtained organic layer was separated, dried with anhydrous sodium sulfate and concentrated under reduced pressure to give the compound 4 (200 mg, 91.3%) in light yellow.

$^1$H NMR (600 MHz, CDCl$_3$) δ 4.18 (d, J=2.4 Hz, 2H), 3.59-3.69 (m, 8H), 3.48 (t, J=5.4 Hz, 2H), 2.84 (s, 2H), 2.40 (m, 1H)

LCB14-0532

A solution of the compound 4 (195 mg, 1.04 mmol) in tetrahydrofuran (4 mL) was treated with triethylamine (290 μL, 2.08 mmol). A solution of 4-chloro-7-nitrobenzofurazan (270 mg, 1.35 mmol) in tetrahydrofuran (1 mL) was added. The resulting mixture was stirred at room temperature for 1 hour. Ethyl acetate (50 mL) and distilled water (50 mL) were added. The thus-obtained organic layer was dried with anhydrous sodium sulfate and concentrated under reduced pressure to give the compound LCB14-0532 (280 mg, 77%).

$^1$H NMR (600 MHz, CDCl$_3$) δ 8.50 (d, J=8.4 Hz, 1H), 6.99 (s, 1H), 6.19 (d, J=8.4 Hz, 1H), 4.19 (d, J=2.4 Hz, 2H), 3.89 (t, J=5.1 Hz, 2H), 3.68-3.75 (m, 10H), 2.41 (t, J=2.4 Hz, 1H)

2-11. Acetylene-Linker-MMAF-OMe (LCB14-0536)

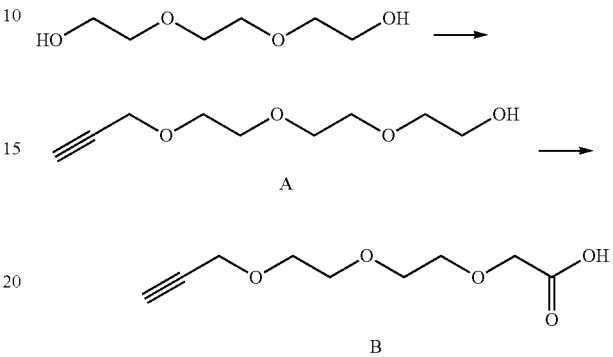

Compound A

To a suspension of NaH (55% in mineral oil, 390 mg, 16.25 mmol) in tetrahydrofuran (10 mL) at 0° C. under nitrogen atmosphere was added slowly a solution of triethylene glycol (4 g, 26.63 mmol) in tetrahydrofuran (20 mL). 80% Propargyl bromide in toluene (1.97 g, 13.31 mmol) was added slowly. The resulting mixture was stirred at the same temperature for 2 hours. After the reaction was completed, dichloromethane (100 mL) and water (100 mL) were added. The thus-obtained organic layer was concentrated and the residue was subjected to column chromatography to give compound (A) (1 g, 43%) in aqueous form.

$^1$H NMR (600 MHz, CDCl$_3$) δ 4.21-4.20 (m, 2H), 3.74-3.66 (m, 10H), 3.62-3.61 (m, 2H), 2.43 (t, J=2.4 Hz, 1H)

Compound B

To a solution of the compound A (1 g, 5.31 mmol) in acetone under nitrogen atmosphere at −5° C. was added slowly 5.3 mL of Jones reagent. The resulting mixture, while being slowly warmed up to room temperature, was stirred for 3 hours. After the reaction was completed, ethyl acetate (100 mL) and water (100 mL) were added. The thus-obtained organic layer was concentrated to give compound (B) (886 mg, 82%) as yellow liquid.

$^1$H NMR (600 MHz, CDCl$_3$) δ 4.21 (d, J=2.4, 2H), 4.18-4.17 (m, 2H), 3.78-3.77 (m, 2H), 3.74-3.70 (m, 6H), 2.44 (t, J=2.4 Hz, 1H)

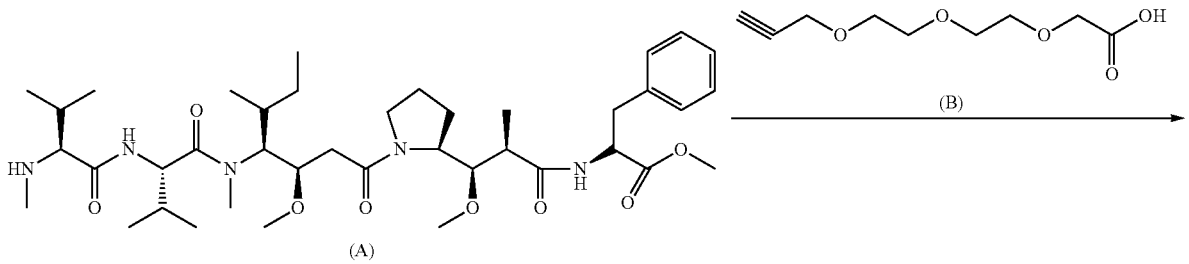

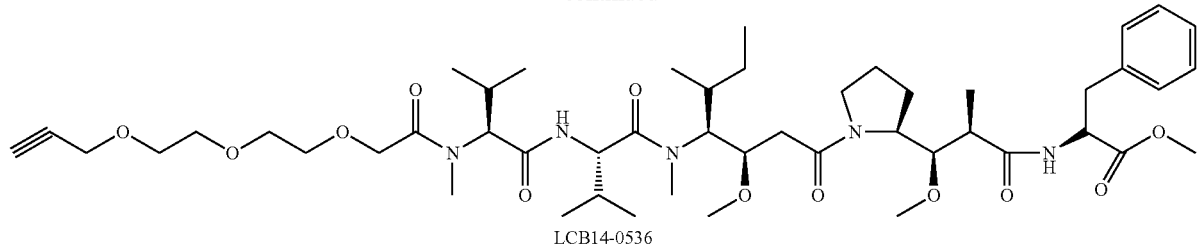

LCB14-0536

LCB14-0536

To a solution of the compound (A) (MMAF-OMe, 100 mg, 0.13 mmol) in acetonitrile (2 mL) at room temperature was added the compound (B) (27 mg, 0.13 mmol), PyBOP (104 mg, 0.19 mmol), and DIPEA (0.03 mL, 0.19 mmol). The resulting mixture was stirred for 12 hours. After the reaction was completed, ethyl acetate (50 mL) and water (20 mL) were added. The thus-obtained organic layer was concentrated under reduced pressure. The residue was subjected to column chromatography with dichloromethane and methanol to give the compound LCB14-0536 (82 mg, 68%) as a yellow solid.

EI-MS m/z: 930(M)

2-12. Acetylene-Linker(Peptide Sequence)-MMAF-OMe (LCB14-0589)

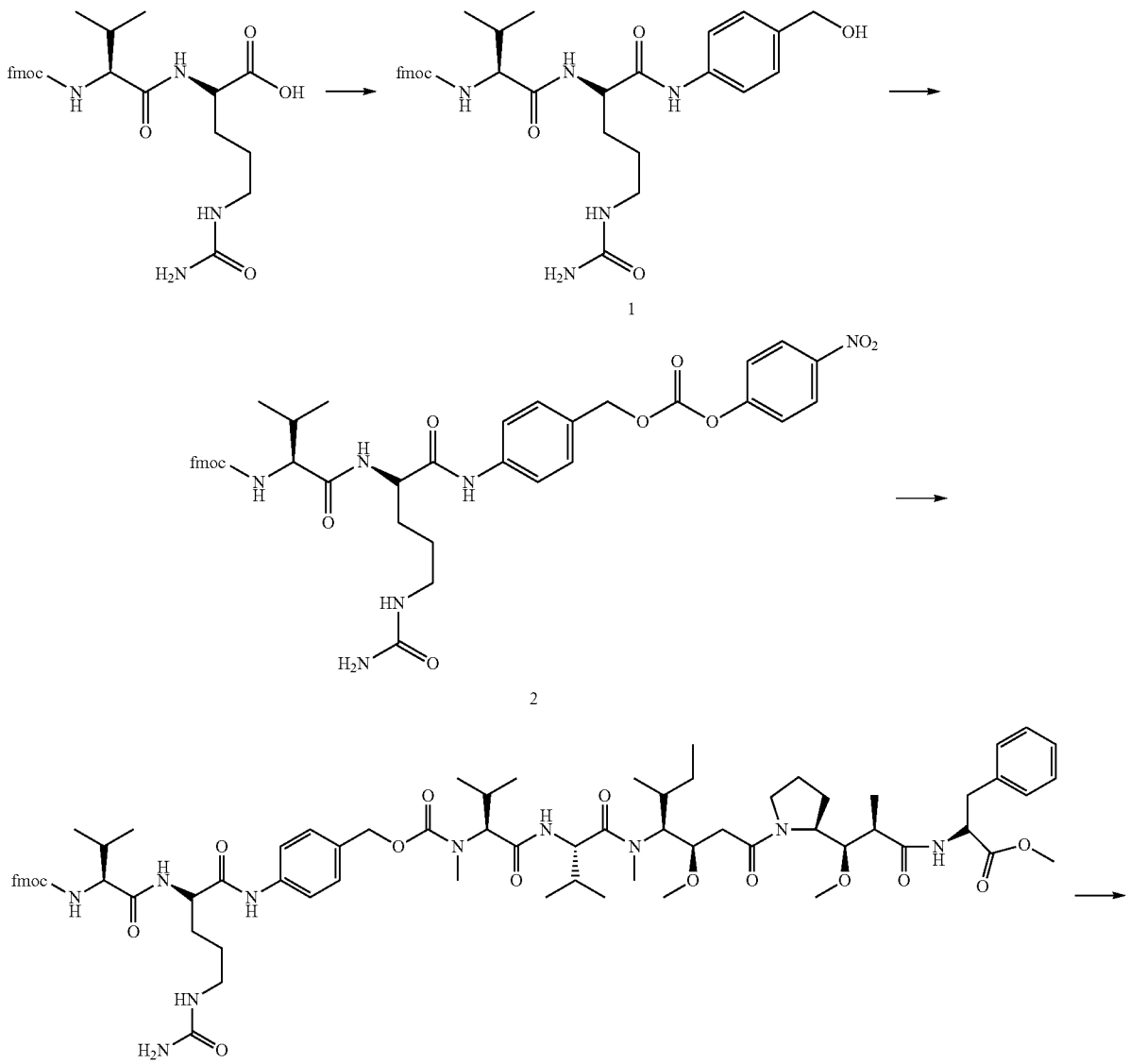

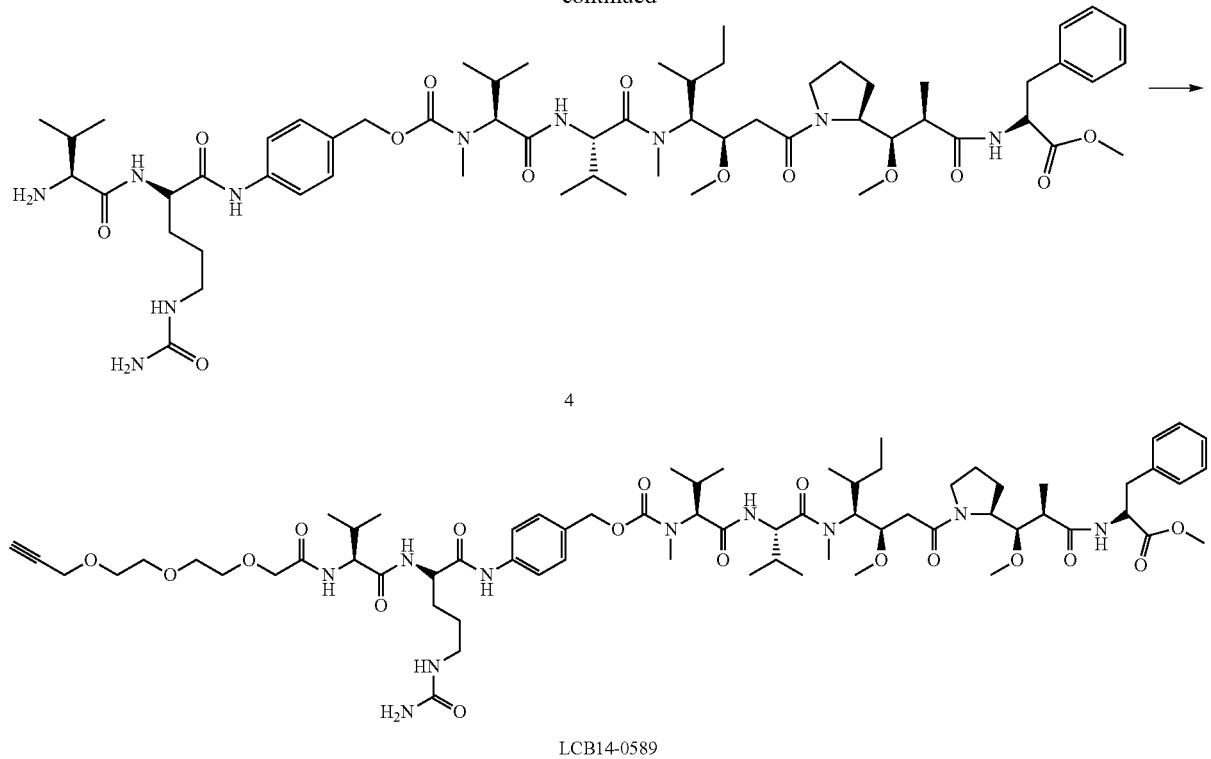

LCB14-0589

Compound 1 (Fmoc-Val-Cit-PAB)

Fmoc-Val-Cit-OH was prepared according to the method described in WO2007/008603, the contents of which are hereby incorporated by reference in their entirety. To a solution of Fmoc-Val-Cit-OH (4.89 g, 9.85 mmol) in dichloromethane (50 mL) and methanol (20 mL) under nitrogen atmosphere were added para-aminobenzylalcohol (2.43 g, 19.70 mmol) and 1-ethoxycarbonyl-2-ethoxy-1,2-dihydroquinoline (1.98 g, 19.7 mmol). The resulting mixture was stirred for 12 hours at room temperature. After the reaction was completed, the solvent was concentrated. The resulting solid was washed with diethyl ether multiple times to give the compound 1 (4.12 g, 70%) as a yellow solid.

$^1$H NMR (600 MHz, DMSO-$d_6$) δ 10.00 (s, 1H), 8.12 (d, J=7.8 Hz, 1H), 7.89 (d, J=7.8 Hz, 2H), 7.75-7.72 (m, 2H), 7.55 (d, J=7.8 Hz, 2H), 7.44-7.41 (m, 2H), 7.33-7.31 (m, 2H), 7.23 (d, J=8.4 Hz, 2H), 6.02 (bs, 1H), 5.41-5.38 (m, 2H), 5.09 (bs, 1H), 4.42 (bs, 2H), 4.30-4.28 (m, 1H), 4.24-4.23 (m, 2H), 3.94-3.91 (m, 1H), 3.02-2.99 (m, 1H), 2.94-2.93 (m, 1H), 2.00-1.99 (m, 1H), 1.7 (bs, 1H), 1.60 (bs, 1H), 1.43 (bs, 1H), 1.36 (bs, 1H), 0.88-0.84 (m, 6H)

Compound 2 (Fmoc-Val-Cit-PABC-PNA)

A solution of the compound 1 (2 g, 3.32 mmol) in DMF (8 mL) was treated sequentially with bis(4-nitrophenyl) carbonate (2.02 g, 6.64 mmol) and diisopropylethylamine (0.647 mL, 4.98 mmol) under nitrogen atmosphere. The resulting mixture was stirred for 12 hours at room temperature. After the reaction was completed, diethyl ether was added for solidification. The resulting solid was washed with diethyl ether and water multiple times to give the compound 2 (1.52 g, 60%) as a yellow solid.

$^1$H NMR (600 MHz, DMSO-$d_6$) δ 10.19 (s, 1H), 8.31 (d, J=9.6 Hz, 2H), 8.15 (d, J=7.8 Hz, 1H), 7.89 (d, J=7.2 Hz, 2H), 7.75-7.72 (m, 1H), 7.66 (d, J=8.4 Hz, 2H), 7.57 (d, J=9.0 Hz, 2H), 7.43-7.39 (m, 4H), 7.32 (t, J=7.2 Hz, 2H), 6.05-6.04 (m, 1H), 5.42 (m, 2H), 5.24 (s, 2H), 4.42 (m, 1H), 4.30-4.28 (m, 1H), 425-4.23 (m, 2H), 3.94-3.91 (m, 1H), 3.01-3.00 (m, 1H), 2.96-2.94 (m, 1H), 2.00-1.99 (m, 1H), 1.70 (m, 1H), 1.59 (m, 1H), 1.45 (m, 1H), 1.37 (m, 1H), 0.89-0.83 (m, 6H).

EI-MS m/z: 767(M$^+$)

Compound 3 (Fmoc-Val-Cit-PABC-MMAF-OMe)

A solution of the compound 2 (200 mg, 0.261 mmol) and MMAF-OMe (194 mg, 0.261 mmol) in DMF (2 mL) was treated with HOBt (7.1 mg, 0.052 mmol), pyridine (1 mL), and DIPEA (0.045 mL, 0.261 mmol). The resulting mixture was stirred at room temperature for 12 hours. After the reaction was completed, ethyl acetate (30 mL), water (30 mL) and saline solution (30 mL) were used to extract an organic layer. The thus-obtained organic layer was concentrated and subjected to column chromatography to give the compound 3 (153 mg, 42%) as a yellow solid.

EI-MS m/z: 1375(M$^+$)

Compound 4 (Val-Cit-PABC-MMAF-OMe)

To a solution of the compound 3 (153 mg, 0.112 mmol) in tetrahydrofuran (5 mL) at room temperature was added piperidine (0.2 mL). The resulting mixture was stirred at the same temperature for 2 hours. After the reaction was completed, recrystallization was performed with ether and hexane to give the compound 4 (85 mg, 66%) as a light yellow solid.

EI-MS m/z: 1152(M$^+$)

LCB14-0589 (Acetylene Linker-Val-Cit-PABC-MMAF-OMe)

To a solution of the compound 4 (85 mg, 0.074 mmol) and the compound B of Example 2-11 (18 mg, 0.088 mmol) in DMF (2 mL) were added DIPEA (0.03 mL, 0.148 mmol) and PyBOP (58 mg, 0.111 mmol). The resulting mixture was stirred at room temperature for 5 hours. After the reaction was completed, extraction was performed with ethyl acetate (20 mL) and water (20 mL). The resulting crude product was subjected to column chromatography to give the compound LCB14-0589 (35.4 mg, 36%) as a white solid.

EI-MS m/z: 1336(M$^+$)

2-13. Acetylene-Linker-Val-Cit-PABC-MMAE (LCB14-0602)

Compound 2 (Fmoc-Val-Cit-PABC-MMAE)

To a solution of Fmoc-Val-Cit-PABC-PNP (200 mg, 0.261 mmol) and MMAE (187 mg, 0.261 mmol) in DMF (2 mL) were added HOBt (7.1 mg, 0.052 mmol), pyridine (1 mL), and DIPEA (0.045 mL, 0.261 mmol). The resulting mixture was stirred at room temperature for 12 hours. After

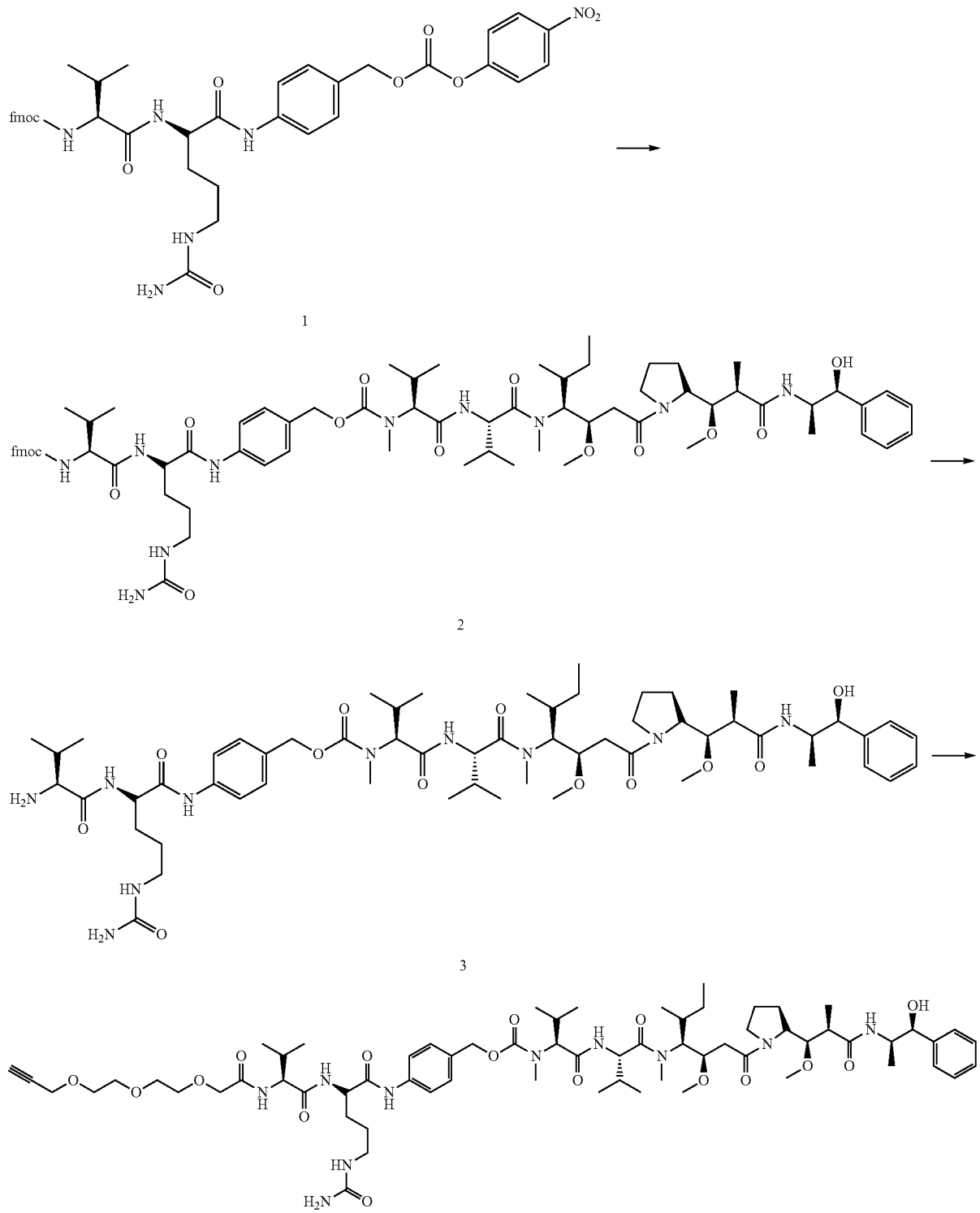

the reaction was completed, ethyl acetate (30 mL), water (30 mL), and saline solution (30 mL) were used to extract an organic layer. The thus-obtained organic layer was concentrated and subjected to column chromatography to give the compound 2 (50 mg, 14.3%) as a yellow solid.

EI-MS m/z: 1346(M+)

Compound 3 (Val-Cit-PABC-MMAE)

To a solution of the compound 2 (50 mg, 0.037 mmol) in tetrahydrofuran (5 mL) at room temperature was added piperidine (0.1 mL). The resulting mixture was stirred at the same temperature for 2 hours. After the reaction was completed, recrystallization was performed with ether and hexane to give the compound 3 (37 mg, 89%) as a light yellow solid.

EI-MS m/z: 1124(M+)

LCB14-0602 (Acetylene Linker-Val-Cit-PABC-MMAE)

To a solution of the compound 3 (35 mg, 0.031 mmol) and The compound B of Example 2-11 (7.6 mg, 0.037 mmol) in DMF (2 mL) at room temperature were added DIPEA (0.011 mL, 0.062 mmol) and PyBOP (24 mg, 0.47 mmol). The resulting mixture was stirred for 5 hours. After the reaction was completed, extraction was performed with ethyl acetate (20 mL) and water (20 mL). The resulting crude product was subjected to column chromatography to give the compound LCB14-0602 (28.5 mg, 70%) as a white solid.

EI-MS m/z: 1308(M+)

2-14. Azide Linker-PBD (Pyrrolobenzodiazepin) Dimer (LCB14-0577)

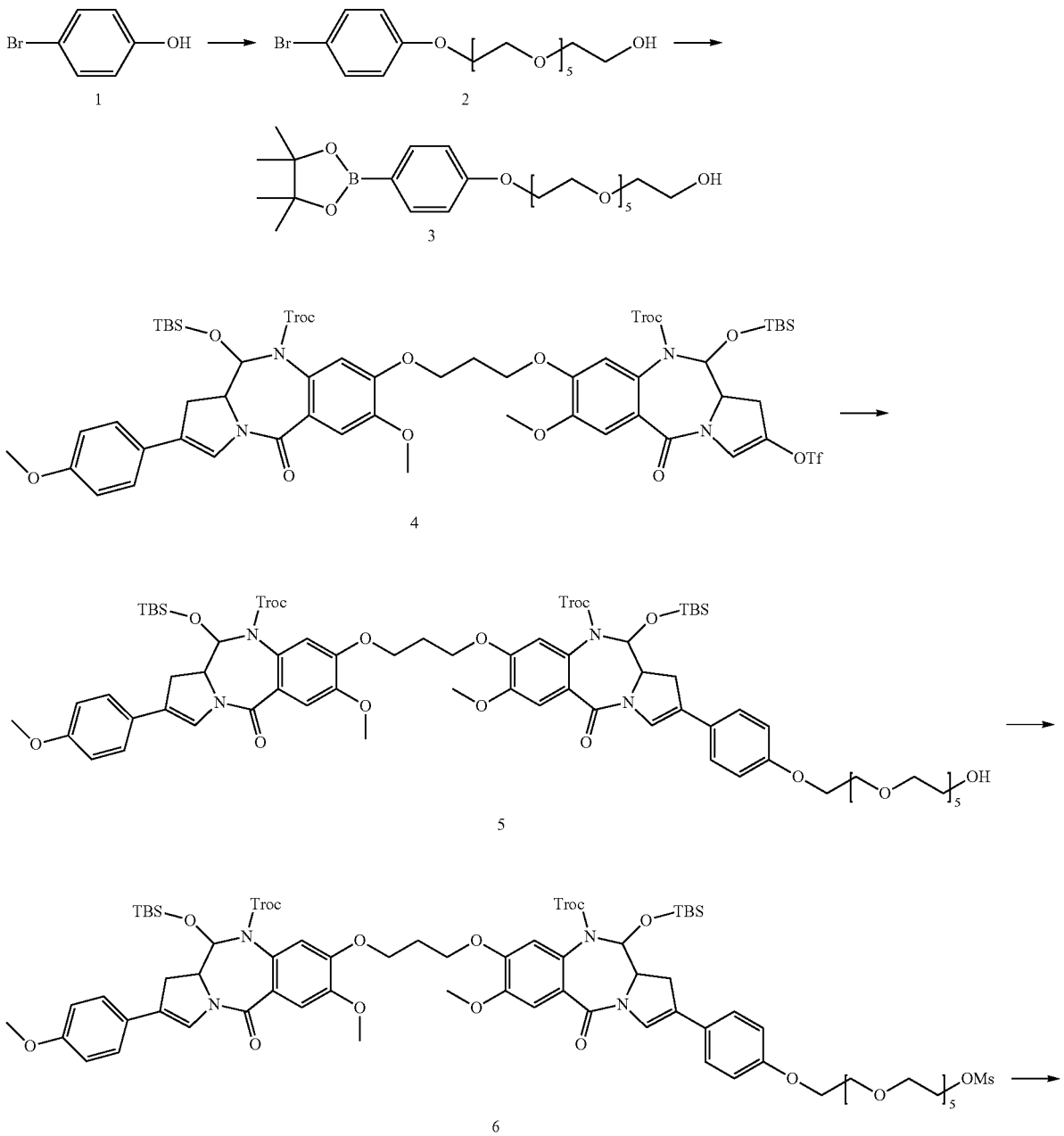

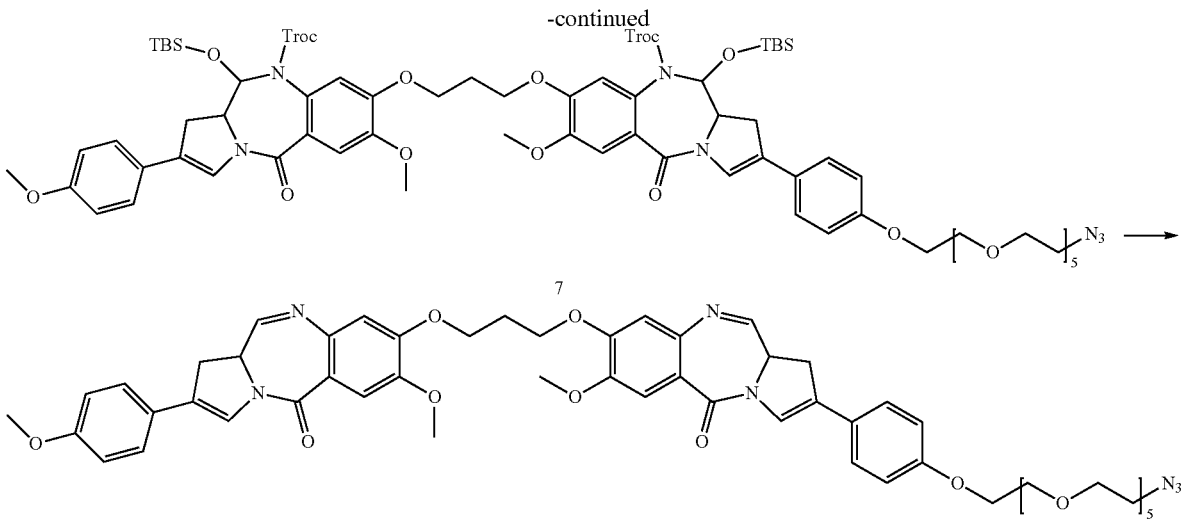

LCB14-0577

Compound 2

To a solution of the compound 1 (1.22 g, 7.08 mmol), triphenylphosphine (TPP, 2.23 g, 8.50 mmol), and hexaethylene glycol (2 g, 7.08 mmol) in tetrahydrofuran (10 mL) at 0° C. under nitrogen atmosphere was added diisopropyl azodicarboxylate (DIAD, 1.67 mL, 8.50 mmol). The resulting mixture was stirred for 1 hour. After the reaction was completed, ethyl acetate (50 mL) and distilled water (50 mL) were added. The thus-obtained organic layer was dried with anhydrous sodium sulfate and concentrated under reduced pressure. The residue was subjected to column chromatography to give the compound 2 (1.4 g, 45%).

$^1$H NMR (600 MHz, CDCl$_3$) δ 7.35 (d, J=8.4 Hz, 2H), 6.80 (d, J=8.4 Hz, 2H), 4.09 (t, J=4.8 Hz, 2H), 3.84 (t, J=4.8 Hz, 2H), 3.72 (t, J=4.8 Hz, 4H), 3.68~3.65 (m, 14H), 3.60 (t, J=4.8 Hz, 2H), 2.85 (bs, 1H)

Compound 3

To a solution of the compound 2 (300 mg, 0.68 mmol) in 1,4-dioxane (5 mL) were sequentially added potassium acetate (200 mg, 2.04 mmol), PdCl$_2$(dppf) (28 mg, 0.034 mmol), and bis(pinacolato)diboron (174 mg, 0.68 mmol). The resulting mixture was stirred at 70° C. for 12 hours. After the reaction was completed, ethyl acetate (50 mL) and distilled water (50 mL) were added. The thus-obtained organic layer was dried with anhydrous sodium sulfate and concentrated under reduced pressure. The residue was subjected to column chromatography to give the compound 3 (300 mg, 90%).

$^1$H NMR (600 MHz, CDCl$_3$) δ 7.73 (d, J=8.4 Hz, 2H), 6.90 (d, J=8.4 Hz, 2H), 4.15 (t, J=4.8 Hz, 2H), 3.86 (t, J=4.8 Hz, 2H), 3.73~3.72 (m, 4H), 3.68~3.64 (m, 14H), 3.60 (t, J=4.8 Hz, 2H), 1.33 (s, 12H)

Compound 4

The compound 4 was prepared according to the methods described in WO2006/111759 A1, WO2010/043880 A1, and WO2010/010347 A1, the contents of each of these references are hereby incorporated by reference in their entirety.

$^1$H NMR (600 MHz, CDCl$_3$) δ 7.35 (s, 1H), 7.29 (d, J=9 Hz, 2H), 7.27 (s, 1H), 7.23 (s, 1H), 7.17 (s, 1H), 6.89 (d, J=9 Hz, 2H), 6.77 (s, 1H), 6.75 (s, 1H), 5.91 (m, 2H), 5.23 (d, J=9 Hz, 2H), 5.21 (d, J=9 Hz, 2H), 4.29 (m, 2H), 4.17~4.13 (m, 4H), 3.96~3.91 (m, 8H), 3.82 (s, 3H), 3.33 (m, 2H), 2.82 (m, 2H), 2.44 (m, 2H), 0.90 (2s, 18H), 0.27 (2s, 12H)

Compound 5

The compound 4 (83 mg, 0.059 mmol), sodium carbonate (10 mg, 0.089 mmol), and Pd(TPP)$_4$ (3.4 mg, 0.003 mmol) were sequentially dissolved in a mixture solvent of ethanol/toluene/distilled water (0.3 mL/0.3 mL/0.3 mL). A solution of the compound 3 (31.6 mg, 0.065 mmol) in toluene (3 mL) was added. The resulting mixture was stirred at room temperature for 1 hour. After the reaction was completed, ethyl acetate (50 mL) and distilled water (50 mL) were added. The thus-obtained organic layer was dried with anhydrous sodium sulfate and concentrated under reduced pressure. The residue was subjected to column chromatography to give the compound 5 (79 mg, 74%).

$^1$H NMR (600 MHz, CDCl$_3$) δ 7.35 (m 2H), 7.31~7.27 (m, 6H), 6.92~6.89 (m, 4H), 6.78 (s, 2H), 5.90 (d, J=9 Hz, 2H), 5.23 (d, J=12.6 Hz, 2H), 4.30 (m, 2H), 4.16~4.13 (m, 6H), 3.97~3.94 (m, 8H), 3.87 (t, J=4.8 Hz, 2H), 3.83 (s, 3H), 3.74~3.64 (m, 18H), 3.61 (m, 2H), 3.34 (m 2H), 2.82 (m, 2H), 2.45 (m, 2H), 0.90 (s, 18H), 0.25 (2s, 12H)

Compound 6

To a solution of the compound 5 (250 mg, 0.155 mmol) in tetrahydrofuran (3 mL) at 0° C. were added 4-methylmorpholine (34.2 μL, 0.310 mmol) and methane sulfonic anhydride (Ms$_2$O, 32.5 mg, 0.186 mmol). The resulting mixture was stirred at room temperature for 3 hours. After the reaction was completed, ethyl acetate (50 mL) and distilled water (50 mL) were added. The thus-obtained organic layer was dried with anhydrous sodium sulfate and concentrated under reduced pressure. The residue was subjected to column chromatography to give the compound 6 (220 mg, 84%).

$^1$H NMR (600 MHz, CDCl$_3$) δ 7.33 (m, 2H), 7.28~7.23 (m, 6H), 6.89~6.86 (m, 4H), 6.76 (s, 2H), 5.88 (d, J=9 Hz, 2H), 5.21 (d, J=12.6 Hz, 2H), 4.35 (m, 2H), 4.26 (m, 2H), 4.13~4.11 (m 6H), 3.92 (s, 6H), 3.84 (t, J=4.8 Hz, 2H), 3.80 (s, 3H), 3.74~3.60 (m, 20H), 3.31 (m, 2H), 3.06 (s, 3H), 2.80 (m, 2H), 2.43 (m, 2H), 0.88 (s, 18H), 0.23 (2s, 12H)

Compound 7

To a solution of the compound 6 (100 mg, 0.059 mmol) in dimethylformamide (2 mL) was added sodium azide (NaN$_3$, 4.6 mg, 0.071 mmol). The resulting mixture was stirred at 55° C. for 4 hours. After the reaction was completed, ethyl acetate (50 mL) and distilled water (50 mL)

were added. The thus-obtained organic layer was dried with anhydrous sodium sulfate and concentrated under reduced pressure. The residue was subjected to column chromatography to give the compound 7 (85 mg, 88%).

$^1$H NMR (600 MHz, CDCl$_3$) δ 7.33 (bs, 2H), 7.28~7.24 (m, 6H), 6.89~6.87 (m, 4H), 6.76 (s, 2H), 5.88 (d, J=9 Hz, 2H), 5.21 (d, J=12.6 Hz, 2H), 4.26 (m, 2H), 4.13~4.11 (m, 6H), 3.92 (m, 8H), 3.84 (t, J=4.8 Hz, 2H), 3.80 (s, 3H), 3.71 (m, 2H), 3.67~3.64 (m, 16H), 3.36 (t, J=4.8 Hz, 2H), 3.31 (m, 2H), 2.80 (m, 2H), 2.43 (m, 2H), 0.88 (s, 18H), 0.23 (2s, 12H)

LCB14-0577

To a solution of the compound 7 (80 mg, 0.049 mmol) in tetrahydrofuran (1.5 mL) were added 1N-ammonium acetate (1 mL) and 10% cadmium/lead couple (120 mg). The resulting mixture was stirred at room temperature for 4 hours. After the reaction was completed, dichloromethane (50 mL) and distilled water (50 mL) were added. The thus-obtained organic layer was dried with anhydrous sodium sulfate and concentrated under reduced pressure. The residue was subjected to column chromatography to give the compound LCB14-0577 (9 mg, 18%).

$^1$H NMR (600 MHz, CDCl$_3$) δ 7.86 (d, J=4.2 Hz, 2H), 7.36 (m, 2H), 7.31~7.23 (m, 6H), 6.89~6.80 (m, 6H), 4.34~4.22 (m, 6H), 4.11 (m, 2H), 3.92 (m, 6H), 3.84~3.77 (m, 5H), 3.71 (m, 2H), 3.67~3.63 (, 18H), 3.36 (m, 2H), 3.03 (m, 2H), 2.44~2.40 (m, 2H)

EI-MS m/z: 1017(M$^+$)

2-15. Acetylene-Linker-PBD Dimer (LCB14-0578)

Compound 2

To a solution of the compound 6 of Example 2-14 (95 mg, 0.056 mmol) in acetonitrile (1 mL) was added a solution of sodium carbonate (18 mg, 0.168 mmol) in propargyl amine (18 μL, 0.28 mmol) and distilled water (500 μL). The resulting mixture was stirred at 40° C. for 12 hours. After the reaction was completed, ethyl acetate (50 mL) and distilled water (50 mL) were added. The thus-obtained organic layer was dried with anhydrous sodium sulfate and concentrated under reduced pressure. The residue was subjected to column chromatography to give the compound 2 (45 mg, 48%).

$^1$H NMR (600 MHz, CDCl$_3$) δ 7.35 (m, 2H), 7.30~7.27 (m, 6H), 6.91~6.89 (m, 4H), 6.78 (s, 2H), 5.91 (d, J=9 Hz, 2H), 5.23 (d, J=11.4 Hz, 2H), 4.30 (m, 2H), 4.16~4.11 (m, 6H), 3.94 (s, 6H), 3.87 (t, J=4.8 Hz, 2H), 3.83 (s, 3H), 3.73 (m, 2H), 3.69~3.60 (m 18H), 3.45 (d, J=2.4 Hz, 2H), 3.33 (m, 2H), 2.87 (t, J=4.8 Hz, 2H), 2.82 (m, 2H), 2.45 (m, 2H), 2.22 (t, J=4.4 Hz, 1H), 0.90 (s, 18H), 0.24 (2s, 12H)

LCB14-0578

To a solution of the compound 2 (40 mg, 0.024 mmol) in tetrahydrofuran (750 μL) were added 1N-ammonium acetate (0.5 mL) and 10% cadmium/lead couple (70 mg). The resulting mixture was stirred at room temperature for 4 hours. After the reaction was completed, dichloromethane (50 mL) and distilled water (50 mL) were added. The thus-obtained organic layer was dried with anhydrous sodium sulfate and concentrated under reduced pressure. The residue was subjected to column chromatography to give the compound LCB14-0578 (13 mg, 52%).

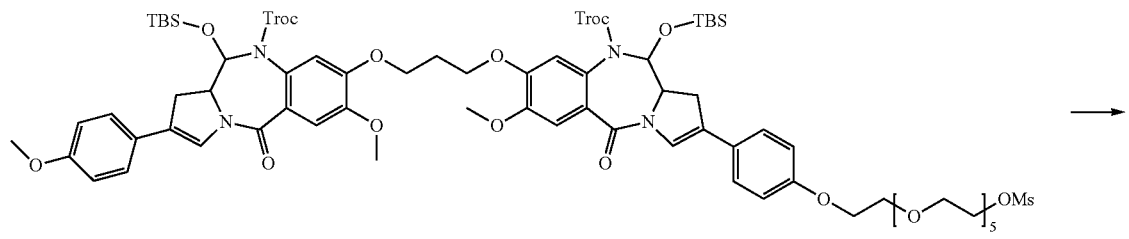

1

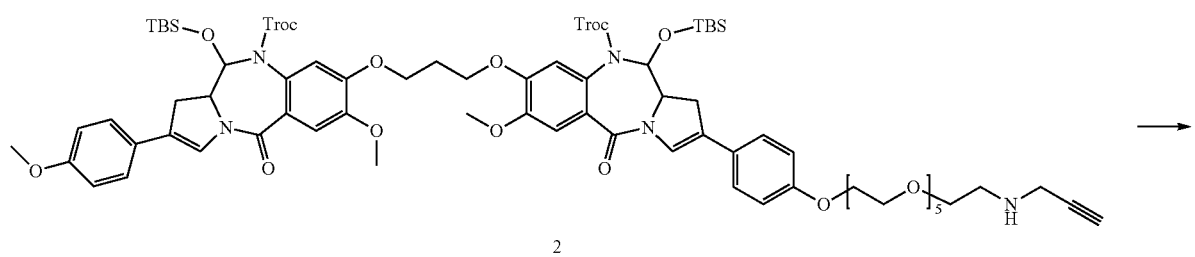

2

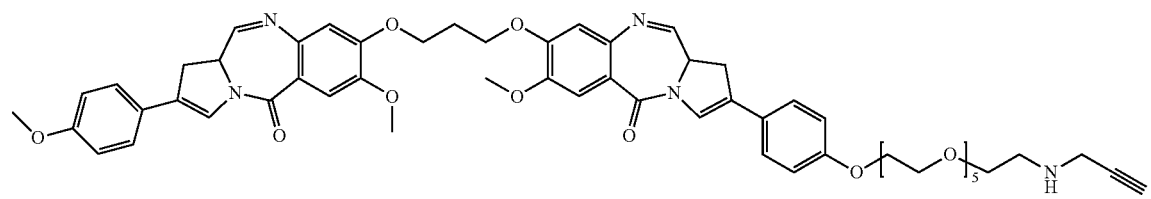

LCB14-0578

¹H NMR (600 MHz, CDCl₃) δ 7.88 (d, J=4.2 Hz, 2H), 7.38 (m, 2H), 7.33~7.28 (m, 6H), 6.91~6.86 (m, 6H), 4.38~4.20 (m, 6H), 4.13 (m 2H), 3.94 (s, 6H), 3.88~3.80 (m, 5H), 3.73 (m, 2H), 3.69~3.61 (m, 16H), 3.46 (d, J=2.4 Hz, 2H), 3.39 (m, 2H), 3.30 (m, 2H), 2.88 (t, J=4.8 Hz, 2H), 2.43 (m, 2H), 2.23 (t, J=4.4 Hz, 1H))
EI-MS m/z: 1028(M⁺)
2-16. Acetylene-Linker-PBD Dimer (Pyridine Version) (LCB14-0582)
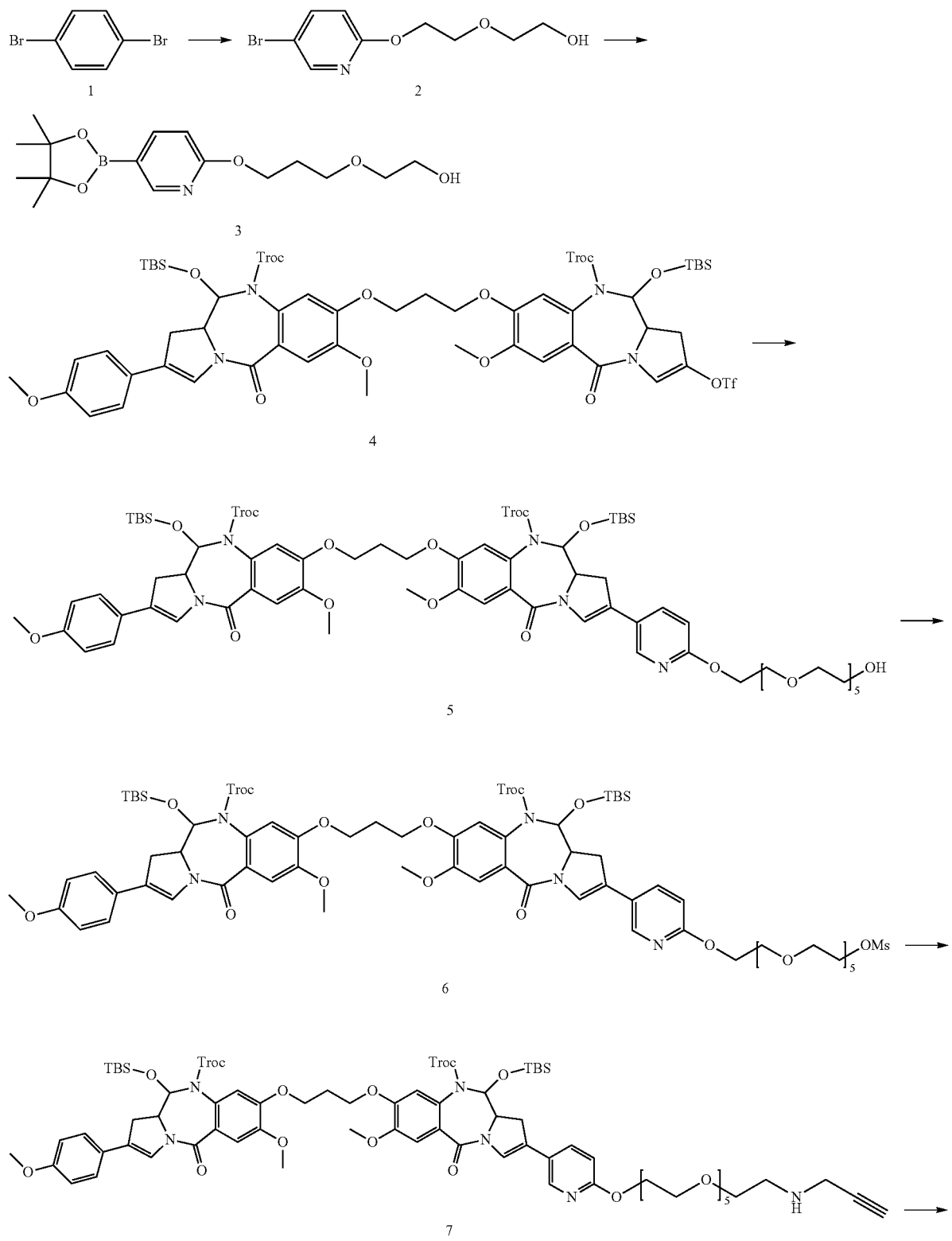

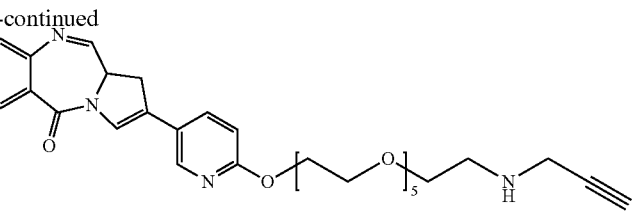

LCB14-0582

Compound 2

To a suspension of NaH (55% in mineral oil, 184 mg, 4.22 mmol) in tetrahydrofuran (5 mL) at 0° C. under nitrogen atmosphere was added hexaethyleneglycol (2.4 g, 8.44 mmol) in tetrahydrofuran (3 mL). The resulting mixture was stirred for 10 minutes at 0° C. A mixture solution prepared by dissolving the compound 1 (1 g, 4.22 mmol) in dimethylformamide (0.5 mL) and tetrahydrofuran (0.5 mL) was slowly added. The resulting mixture was stirred at room temperature for 1 hour and then stirred at 70° C. for 12 hours. After cooling the resulting mixture to 0° C., distilled water (2 mL) was added. After the reaction was completed, ethyl acetate (100 mL) and distilled water (100 mL) were added. The thus-obtained organic layer was dried with anhydrous sodium sulfate and concentrated under reduced pressure. The residue was subjected to column chromatography to give the compound 2 (1.5 g, 81%).

$^1$H NMR (600 MHz, CDCl$_3$) δ 8.13 (d, J=2.4 Hz, 1H), 7.61 (dd, J=8.4, 2.4 Hz, 1H), 6.67 (d, J=9 Hz, 1H), 4.41 (m, 2H), 3.81 (m, 2H), 3.70~3.61 (m, 18H), 3.58 (m, 2H), 2.71 (bs, 1H)

Compound 3

A solution of the compound 2 (500 mg, 1.14 mmol) in dimethylformamide (5 mL) was treated sequentially with potassium acetate (336 mg, 3.42 mmol), PdCl$_2$(dppf) (46.5 mg, 0.057 mmol), and bis(pinacolato)diboron (318 mg, 1.25 mmol). The resulting mixture was stirred at 70° C. for 12 hours. After the reaction was completed, ethyl acetate (100 mL) and distilled water (50 mL) were added. The thus-obtained organic layer was dried with anhydrous sodium sulfate and concentrated under reduced pressure. The residue was subjected to column chromatography to give the compound 3 (250 mg, 45%).

$^1$H NMR (400 MHz, CDCl$_3$) δ 8.50 (s, 1H), 7.90 (d, J=8.4 Hz, 1H), 6.74 (d, J=8.4 Hz, 1H), 4.50 (t, J=4.8 Hz, 2H), 3.84 (m, 2H), 3.74~3.70 (m, 20H), 1.33 (s, 12H)

Compound 5

The compound 4 (245 mg, 0.175 mmol), sodium carbonate (28 mg, 0.262 mmol), and Pd(TPP)$_4$ (10 mg, 0.009 mmol) were sequentially dissolved in a mixture solution of ethanol/toluene/distilled water (1.5 mL/1.5 mL/1.5 mL). A solution of the compound 3 (94 mg, 0.192 mmol) in toluene (1.5 mL) was added. The resulting mixture was stirred at room temperature for 12 hours. After the reaction was completed, ethyl acetate (100 mL) and distilled water (100 mL) were added. The thus-obtained organic layer was dried with anhydrous sodium sulfate and concentrated under reduced pressure. The residue was subjected to column chromatography to give the compound 5 (100 mg, 35.5%).

$^1$H NMR (600 MHz, CDCl$_3$) δ 8.02 (d, J=2.4 Hz, 1H), 7.66 (m, 1H), 7.38 (s, 1H), 7.35 (s, 1H), 7.29 (d, J=9 Hz, 2H), 6.89 (d, J=9 Hz, 2H), 6.80 (d, J=8.4 Hz, 1H), 6.78 (s, 2H), 5.90 (d, J=9 Hz, 2H), 5.23 (dd, J=11.4, 4.2 Hz, 2H), 4.47 (m, 2H), 4.29 (m, 2H), 4.17~4.12 (m, 2H), 3.4 (m, 8H), 3.86 (t, J=4.8 Hz, 2H), 3.82 (m, 4H), 3.74~3.65 (m, 18H), 3.61 (m, 2H), 3.33 (m, 2H), 2.83 (m, 2H), 2.45 (m, 2H), 0.90 (s, 18H), 0.25 (2s, 12H)

Compound 6

To a solution of the compound 5 (180 mg, 0.11 mM) in tetrahydrofuran (3 ml) at 0° C. were added 4-methylmorpholine (NMM, 61.5 µL, 0.55 mM) and methane sulfonic anhydride (Ms$_2$O, 22 mg, 0.121 mM). The resulting mixture was stirred at room temperature for 3 hours. After the reaction was completed, ethyl acetate (50 ml) and distilled water (50 ml) were added to extract an organic layer. The organic layer was dried with anhydride sodium sulfate and concentrated under reduced pressure. The residue was subjected to column chromatography to prepare the compound 6 (80 mg, 43%).

$^1$H NMR (600 MHz, CDCl$_3$) δ 8.03 (d, J=2.4 Hz, 1H), 7.66 (dd, J=7.8, 2.4 Hz, 1H), 7.38 (s, 1H), 7.35 (s, 1H), 7.30 (d, J=9 Hz, 2H), 7.27 (m, 2H), 6.89 (d, J=9 Hz, 2H), 6.80 (d, J=9 Hz, 1H), 6.78 (s, 2H), 5.90 (d, J=9 Hz, 2H), 5.22 (dd, J=12, 4.2 Hz, 2H), 4.47 (m, 2H), 4.38 (m, 2H), 4.30 (m, 2H), 4.15 (m, 3H), 3.99~3.93 (m, 7H), 3.86 (m, 2H), 3.83 (s, 3H), 3.76 (m, 2H), 3.71 (m, 2H), 3.69~3.63 (m, 16H), 3.34 (m, 2H), 3.08 (s, 3H), 2.83 (m, 2H), 2.45 (m, 2H), 0.90 (2s, 18H), 0.25 (2s, 12H)

Compound 7

To a solution of the compound 6 (80 mg, 0.047 mmol) in acetonitrile (4 mL) was added a solution of sodium carbonate (20 mg, 0.141 mmol) in propargylamine (30 µL, 0.47 mmol) and distilled water (500 µL). The resulting mixture was stirred at 50° C. for 12 hours. After the reaction was completed, ethyl acetate (50 mL) and distilled water (50 mL) were added. The thus-obtained organic layer was dried with anhydrous sodium sulfate and concentrated under reduced pressure. The residue was subjected to column chromatography to give the compound 7 (25 mg, 32%).

$^1$H NMR (600 MHz, CDCl$_3$) δ 8.03 (d, J=1.8 Hz, 1H), 7.66 (dd, J=8.4, 2.4 Hz, 1H), 7.38 (s, 1H), 7.35 (s, 1H), 7.30 (d, J=8.4 Hz, 2H), 7.28 (m, 2H), 6.89 (d, J=9 Hz, 2H), 6.79 (d, J=9 Hz, 1H), 6.78 (s, 2H), 5.90 (d, J=9 Hz, 2H), 5.22 (dd, J=12, 4.2 Hz, 2H), 4.47 (m, 2H), 4.30 (m, 2H), 4.17~4.14 (m, 3H), 3.98~3.93 (m, 7H), 3.86 (m, 2H), 3.82 (s, 3H), 3.72 (m, 2H), 3.69~3.60 (m, 18H), 3.45 (d, J=2.4 Hz, 2H), 3.34 (m, 2H), 2.87 (t, J=4.8 Hz, 2H), 2.83 (m, 2H), 2.45 (m, 2H), 2.22 (m, 1H), 0.90 (2s, 18H), 0.25 (2s, 12H)

LCB14-0582

To a solution of the compound 7 (25 mg, 0.015 mmol) in tetrahydrofuran (750 µL) were added 1N-ammonium acetate (0.5 mL) and 10% cadmium/lead couple (50 mg). The resulting mixture was stirred at room temperature for 3 hours. After the reaction was completed, dimethylchloromethane (50 mL) and distilled water (50 mL) were added. The thus-obtained organic layer was dried with anhydrous sodium sulfate and concentrated under reduced pressure. The residue was subjected to column chromatography to give the compound LCB14-0582 (6 mg, 38.4%).

¹H NMR (600 MHz, CDCl₃) δ 8.00 (m, 1H), 7.88 (m, 2H), 7.60 (m, 1H), 7.41~7.28 (m, 6H), 6.90~6.71 (m, 5H), 4.46 (m, 2H), 4.35~4.24 (m, 4H), 3.95~3.79 (m, 11H), 3.70 (m, 2H), 3.68~3.61 (m, 18H), 3.47 (m, 2H), 3.38 (m, 2H), 3.04 (m, 2H), 2.89 (t, J=5.4 Hz, 2H), 2.40 (m, 2H), 2.23 (bs, 1H)

EI-MS m/z: 1029(M⁺)

2-17. Amino-Peg5-PBD Dimer (LCB14-0594)

3.89-3.87 (m, 2H), 3.86-3.84 (m, 2H), 3.82 (s, 3H), 3.74-3.71 (m, 4H), 3.67-3.66 (m, 2H), 3.63-3.62 (m, 6H), 3.59-3.58 (m, 6H), 3.33 (m, 2H), 2.85-2.82 (m, 2H), 2.42 (m, 2H), 0.91 (s, 18H), 0.27 (2s, 12H)

Compound 2

To a solution of the compound 1 (492 mg, 0.283 mmol) in ethyl alcohol (2 mL) and tetrahydrofuran (2 mL) was added hydrazine monohydrate (0.07 mL, 1.417 mmol). The

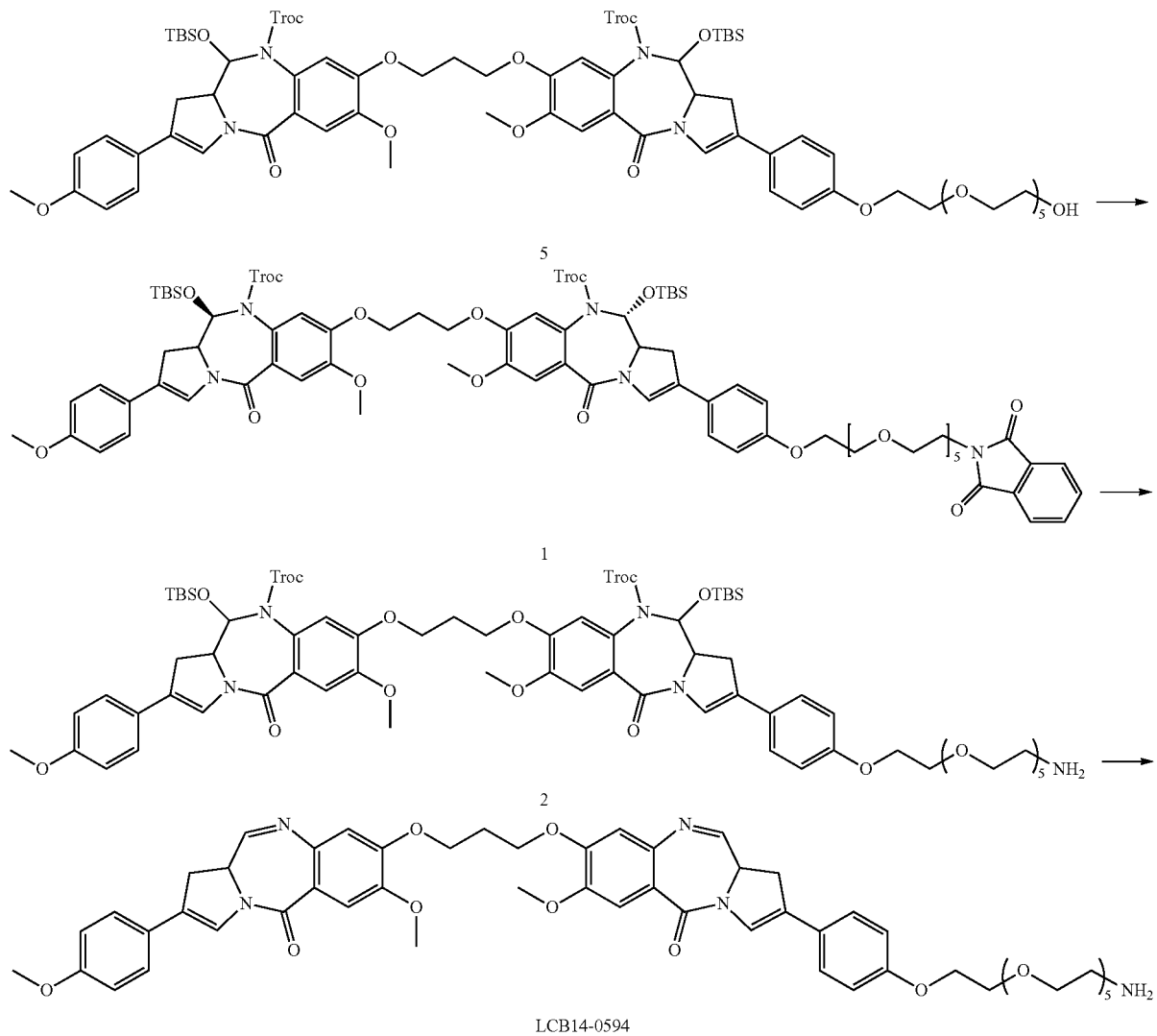

LCB14-0594

Compound 1

To a solution of the compound 5 of Example 2-14 (456 mg, 0.284 mmol) in tetrahydrofuran were added triphenylphosphine (108 mg, 0.411 mmol) and phthalimide (50 mg, 0.341 mmol). DIAD (0.058 mL, 0.340 mmol) was slowly added at 0° C. The resulting mixture was stirred at room temperature for 2 hours. After the reaction was completed, extraction was performed with dichloromethane (40 mL) and water (40 mL). The residue was subjected to column chromatography to give the compound 1 (492 mg, quantitative) as a yellow solid.

¹H NMR (600 MHz, CDCl₃) δ 7.84-7.82 (m, 2H), 7.70-7.69 (m, 2H), 7.34 (m, 2H), 7.29-7.25 (m, 6H), 6.90 (d, J=7.2, 4H), 6.78 (s, 2H), 5.92 (d, J=9.0, 2H), 5.21 (d, J=12.6, 2H), 4.28 (m, 2H), 4.19-4.10 (m, 4H), 3.93 (m, 6H), resulting mixture was stirred at 60° C. for 5 hours. After the reaction was completed, 2 mL of ethyl acetate was added. Solid was filtered off. The filtrate was concentrated and subjected to column chromatography to give the compound 2 (380 mg, 83%) as a yellow solid.

¹H NMR (600 MHz, CDCl₃) δ 7.35 (bs, 2H), 7.29-7.26 (m, 6H), 6.92-6.88 (m, 4H), 6.79 (bs, 2H), 5.92 (d, J=8.4, 2H), 5.21 (d, J=12, 2H), 4.29-4.28 (m, 2H), 4.19-4.17 (m, 6H), 3.93-3.90 (m, 6H), 3.89-3.87 (m, 2H), 3.82 (s, 3H), 3.75-3.73 (m, 2H), 3.69-3.63 (m, 12H), 3.35-3.31 (m, 2H), 2.96 (bs, 2H), 2.85 (d, J=16.8, 2H), 2.43 (m, 2H), 0.91 (s, 18H), 0.27 (2s, 12H).

EI-MS m/z: 1606(M⁺)

LCB14-0594

A solution of the compound 2 (25 mg, 0.015 mmol) in tetrahydrofuran (1 mL) at room temperature was added 1N ammonium acetate (0.4 mL) and 10% Cadmium/lead couple (40 mg). The resulting mixture was stirred at the same temperature for 12 hours. After the reaction was completed, the resulting mixture was filtered with dichloromethane. The filtered solution was concentrated and subjected to column chromatography to give the LCB14-0594 (4 mg, 26%) as a yellow solid.

EI-MS m/z: 990(M$^+$)

2-18. Glucuronide-Linker-PBD Monomer (LCB14-0596)

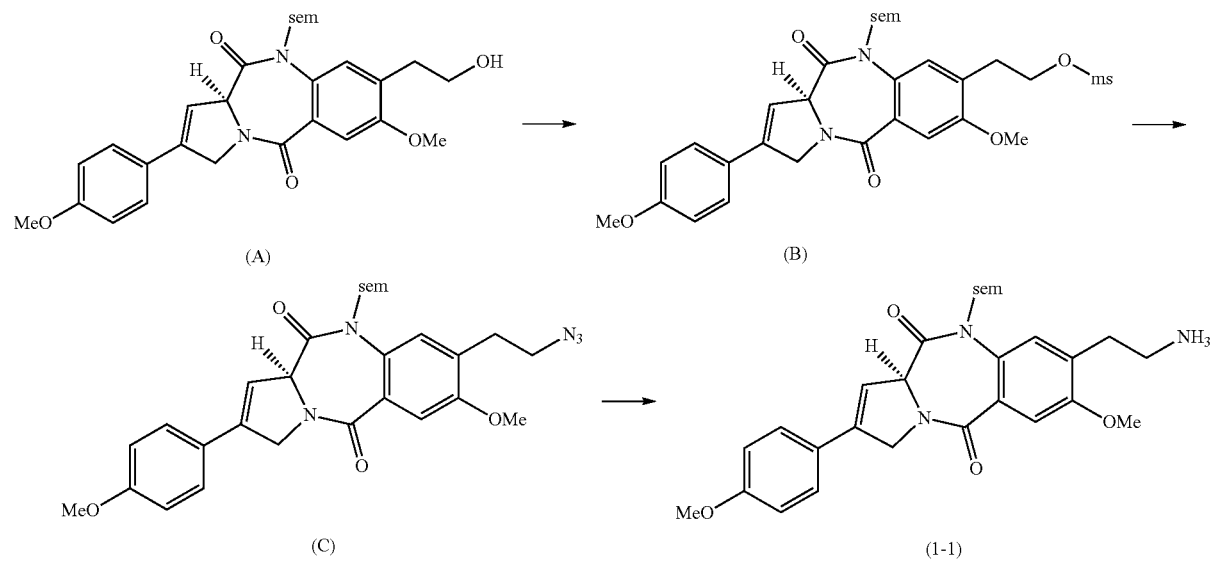

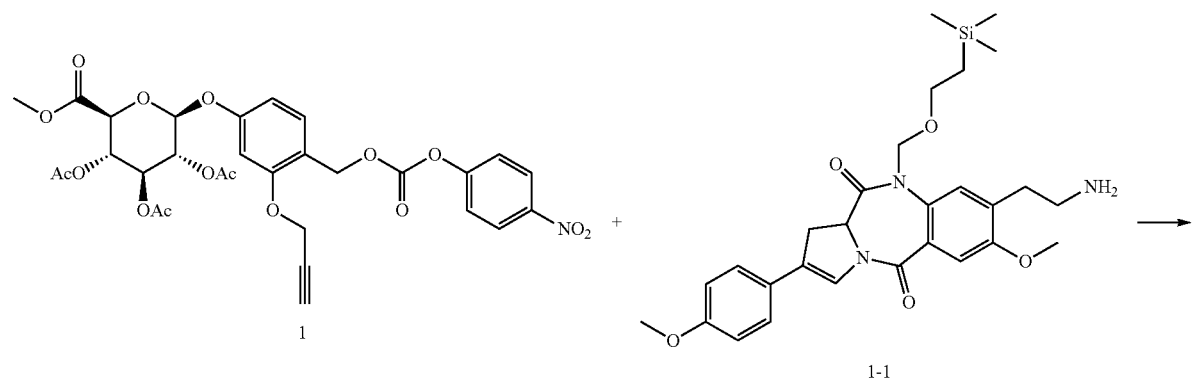

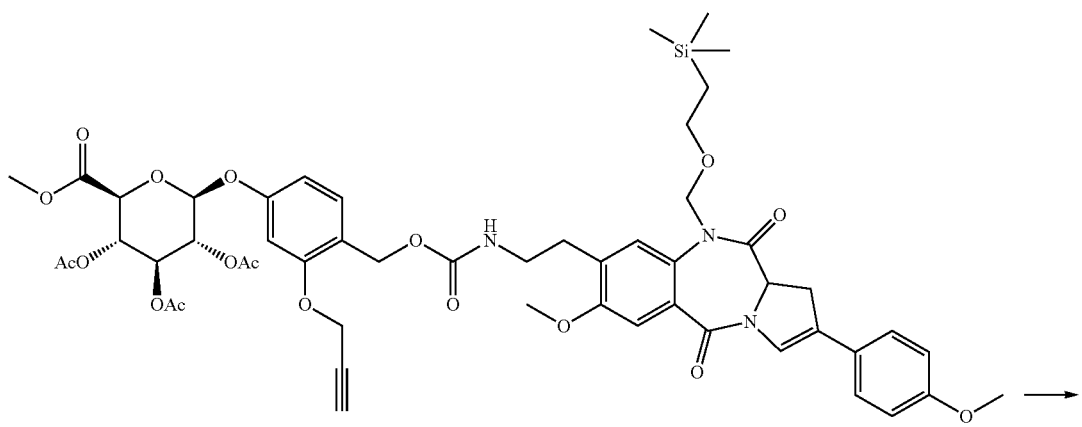

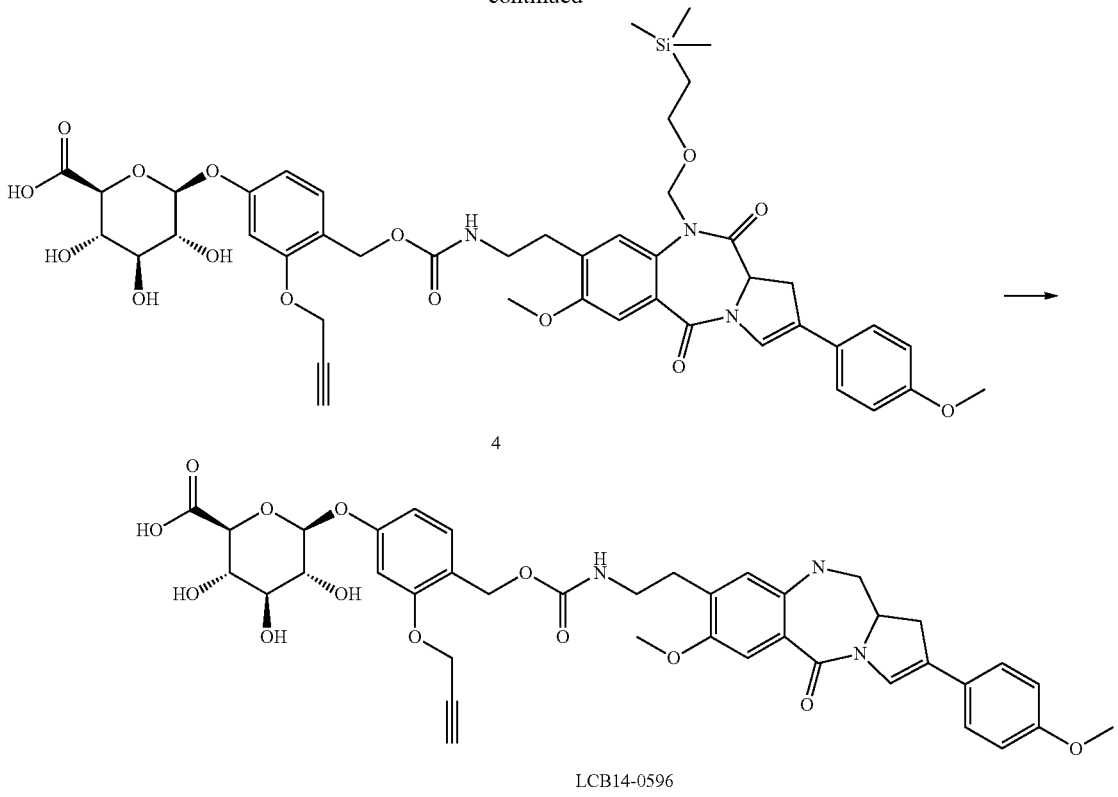

LCB14-0596

Compound (B)

To a solution of the compound (A) (300 mg, 0.57 mmol) in tetrahydrofuran (5 mL) at room temperature were added N-methylmorpholine (0.16 mL, 1.43 mmol) and methanesulfonic anhydride (120 mg, 0.69 mmol). The resulting mixture was stirred for 4 hours. Ethyl acetate (100 mL) and water (50 mL) were added. The thus-obtained organic layer was concentrated under reduced pressure. The residue was subjected to column chromatography with ethyl acetate and hexane to give the compound (B) (330 mg, 96%).

$^1$H NMR (600 MHz, CDCl$_3$) δ: 7.53 (s, 1H), 7.40 (s, 1H), 7.39-7.37 (m, 2H), 7.33 (t, J=1.8 Hz, 1H), 6.90-6.89 (m, 2H), 5.47 (d, J=10.2 Hz, 1H), 4.81 (d, J=10.2 Hz, 1H), 4.62 (dd, J=7.2, 3.0 Hz, 1H), 4.49-4.41 (m, 2H), 3.97-3.93 (m, 1H), 3.92 (s, 3H), 3.83 (s, 3H), 3.76-3.72 (m, 1H), 3.68-3.64 (m, 1H), 3.17-3.10 (m, 3H), 2.96 (s, 3H), 0.98 (t, J=8.4 Hz, 2H), 0.02 (s, 9H).

EI-MS m/z: 603(M$^+$)

Compound (C)

To a solution of the compound (B) (330 mg, 0.55 mmol) in DMF (3 mL) at room temperature was added sodium azide (43 mg, 0.66 mmol). The resulting mixture was stirred at 60° C. for 3 hours. Ethyl acetate (100 mL) and water (50 mL) were added. The thus-obtained organic layer was concentrated under reduced pressure. The residue was subjected to column chromatography with ethyl acetate and hexane to give the compound (C) (307 mg, 99%) as a yellow solid.

$^1$H NMR (600 MHz, CDCl$_3$) δ: 7.54 (s, 1H), 7.38-7.37 (m, 3H), 7.34 (t, J=1.8 Hz, 1H), 6.90-6.88 (m, 2H), 5.49 (d, J=10.2 Hz, 1H), 4.76 (d, J=10.2 Hz, 1H), 4.63 (dd, J=7.2, 3.0 Hz, 1H), 3.96-3.93 (m, 1H), 3.92 (s, 3H), 3.83 (s, 3H), 3.79-3.75 (m, 1H), 3.69-3.65 (m, 1H), 3.52-3.50 (m, 2H), 3.16-3.12 (m, 1H), 3.03-2.99 (m, 1H), 2.96-2.91 (m, 1H), 0.99 (t, J=8.4 Hz, 2H), 0.02 (s, 9H).

EI-MS m/z: 550(M$^+$)

Compound (1-1)

To a solution of the compound (C) (500 mg, 0.91 mmol) in tetrahydrofuran (2 mL) and distilled water (0.5 mL) at room temperature was added triphenylphosphine (285 mg, 1.09 mmol). The resulting mixture was stirred at 40° C. for 13 hours. Ethyl acetate (200 mL) and water (100 mL) were added. The thus-obtained organic layer was concentrated under reduced pressure. The residue was subjected to column chromatography with ethyl acetate and hexane to give the compound (1-1) (435 mg, 93%) as a yellow solid.

$^1$H NMR (600 MHz, CDCl$_3$) δ: 7.50 (s, 1H), 7.38-7.36 (m, 3H), 7.33 (t, J=1.8 Hz, 1H), 6.90-6.88 (m, 2H), 5.47 (d, J=9.6 Hz, 1H), 4.81 (d, J=9.6 Hz, 1H), 4.67 (dd, J=7.2, 3.0 Hz, 1H), 3.95-3.92 (m, 1H), 3.91 (s, 3H), 3.83 (s, 3H), 3.76-3.72 (m, 1H), 3.68-3.64 (m, 1H), 3.15-3.10 (m, 2H), 3.06-2.96 (m, 2H), 2.94-2.88 (m, 1H), 2.86-2.80 (m, 1H), 0.98 (t, J=8.4 Hz, 2H), 0.02 (s, 9H).

EI-MS m/z: 524(M$^+$)

Compound 3

To a solution of the compound 7 of Example 2-4 (126 mg, 0.190 mmol) and the compound (1-1) (100 mg, 0.190 mmol) in dimethylformamide (3 mL) was added triethylamine (TEA, 80 μL, 0.57 mmol). The resulting mixture was stirred at room temperature for 3 hours. After the reaction was completed, ethyl acetate (100 mL) and distilled water (100 mL) were added. The thus-obtained organic layer was dried with anhydrous sodium sulfate and concentrated under reduced pressure. The residue was subjected to column chromatography to give the compound 3 (178 mg, 89%).

$^1$H NMR (400 MHz, CDCl$_3$) δ 7.46 (s, 1H), 7.37 (d, J=8.8 Hz, 2H), 7.34 (m, 2H), 7.22 (m, 1H), 6.87 (d, J=8.8 Hz, 2H), 6.71 (d, J=2.0 Hz, 1H), 6.60 (m, 1H), 5.44 (d, J=10.4 Hz, 1H), 5.34 (m, 2H), 5.27 (m, 1H), 5.16 (d, J=7.6 Hz, 1H), 5.07 (s, 2H), 4.82~4.77 (m, 2H), 4.68 (d, J=2.0 Hz, 2H), 4.60 (m, 1H), 4.19 (d, J=9.2 Hz, 1H), 3.93 (m, 1H), 3.87 (s, 3H), 3.82 (s, 3H), 3.72~3.61 (m, 5H), 3.45 (m, 2H), 3.11 (m, 1H), 2.93~2.84 (m, 2H), 2.51 (bs, 1H), 2.05 (s, 3H), 2.04 (s, 3H), 2.03 (s, 3H), 0.97 (t, J=7.2 Hz, 2H), 0.01 (s, 9H)

Compound 4

To a solution of the compound 3 (100 mg, 0.094 mmol) in methanol (5 mL) at 0° C. was added lithium hydroxide (40 mg, 1.880 mmol) in distilled water (2 mL). The resulting mixture was stirred at room temperature for 3 hours. After the reaction was completed, methanol was removed under reduced pressure. The residue was diluted with distilled water (50 mL) and acidified slowly with acetic acid to pH=3. Extraction was performed three times with dichloromethane (3×50 mL). The resulting product was concentrated under reduced pressure to yield a solid compound. The solid compound was washed with diethyl ether (50 mL) to give the compound 4 (86.5 mg, 100%).

$^1$H NMR (600 MHz, CD$_3$OD) δ 7.43 (s, 1H), 7.41 (d, J=9 Hz, 2H), 7.30 (d, J=10.2 Hz, 2H), 7.14 (d, J=7.8 Hz, 1H), 6.90 (d, J=9 Hz, 2H), 6.86 (m, 1H), 6.66 (m, 1H), 5.22 (m, 2H), 4.98~4.94 (m, 3H), 4.71~4.67 (m, 3H), 3.96 (m, 1H), 3.87 (s, 3H), 3.78 (s, 3H), 3.75 (m, 1H), 3.59~3.47 (m, 5H), 3.36 (m, 2H), 3.25 (m, 1H), 3.13 (m, 1H), 2.90 (bs, 1H), 2.85 (m, 2H), 0.83 (m, 2H), 0.01 (s, 9H)

EI-MS m/z: 904(M$^+$)

LCB14-0596

To a solution of the compound 4 (86.5 mg, 0.094 mmol) in tetrahydrofuran (1 mL) and ethanol (1 mL) at 0° C. was added lithium borohydride 2M-tetrahydrofuran solution (940 μL, 1.88 mmol). The resulting mixture was stirred at room temperature for 12 hours. Additional lithium borohydride 2M-tetrahydrofuran solution (1.41 mL, 2.82 mmol) was added. The resulting mixture was stirred for 5 hours and cooled to 0° C. The reaction was quenched by addition of 1% formic acid solution (33 mL). The resulting mixture was stirred for 3 hours. After the reaction was completed, extraction was performed with distilled water (50 mL) and a mixture solution of ethyl acetate (20 mL) and methanol (10 mL). The residue was subjected to column chromatography using chloroform/methanol/formic acid (V:V:V=9:1:0.05) to give the compound LCB14-0596 (50 mg, 69%).

EI-MS m/z: 756(M$^+$)

2-19. Glucuronide Linker-PBD Dimer (LCB14-0597)

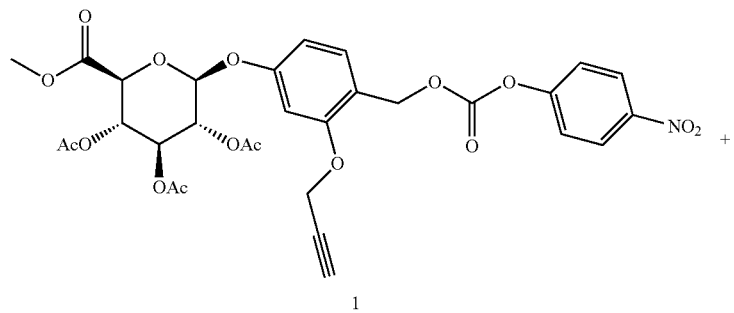

1

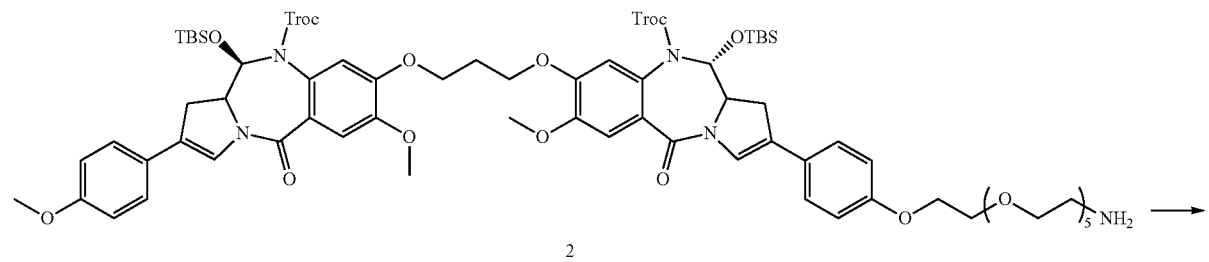

2

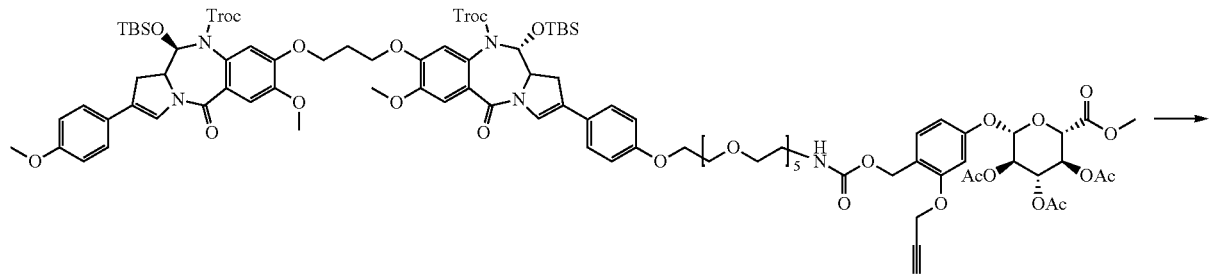

3

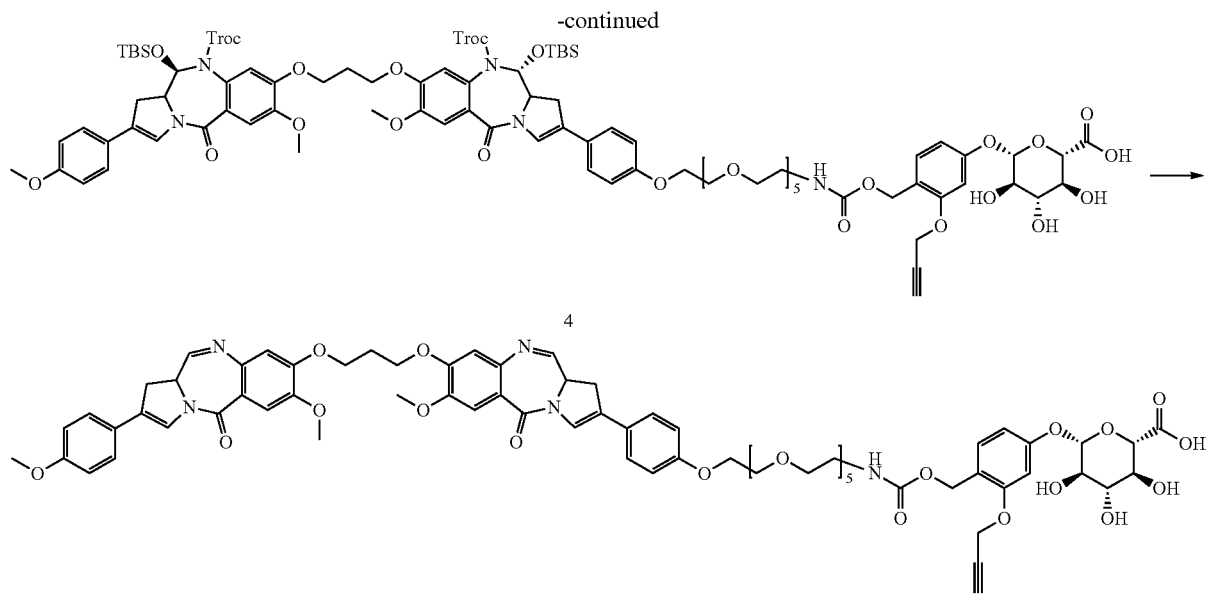

LCB14-0597

Compound 3

To a solution of the compound 7 of Example 2-4 (150 mg, 0.220 mmol) and the compound 2 of Example 2-17 (365 mg, 0.220 mmol) in dimethylformamide (3 mL) was added triethylamine (95 μL, 0.66 mmol). The resulting mixture was stirred at room temperature for 2 hours. After the reaction was completed, ethyl acetate (100 mL) and distilled water (100 mL) were added. The thus-obtained organic layer was dried with anhydrous sodium sulfate and concentrated under reduced pressure. The residue was subjected to column chromatography to give the compound 3 (310 mg, 64%).

$^1$H NMR (600 MHz, CDCl$_3$) δ 7.35 (m, 2H), 7.30~7.25 (m, 7H), 6.90 (m, 4H), 6.78 (s, 2H), 6.73 (d, J=2.4 Hz, 1H), 6.60 (dd, 8.4, 1.8 Hz, 1H), 5.90 (d, J=2.4 Hz, 2H), 5.36~5.32 (m, 2H), 5.27 (m, 2H), 5.22 (m, 2H), 5.13 (d, J=7.2 Hz, 1H), 5.09 (s, 2H), 4.69 (d, J=2.4 Hz, 2H), 4.29 (m 2H), 4.17~4.13 (m, 6H), 3.94 (m, 8H), 3.85 (t, J=4.8 Hz, 2H), 3.82 (s, 3H), 3.73 (s, 3H), 3.71 (m, 2H), 3.67~3.59 (m, 14H), 3.54 (t, J=4.8 Hz, 2H), 3.39~3.31 (m, 4H), 2.82 (m, 2H), 2.52 (t, J=2.4 Hz, 1H), 2.44 (m, 2H), 2.06 (s, 3H), 2.05 (s, 3H), 2.04 (s, 3H), 0.91 (s, 18H), 0.26 (2s, 12H)

Compound 4

To a solution of the compound 3 (100 mg, 0.047 mmol) in methanol (3 mL) and tetrahydrofuran (1.5 mL) at 0° C. was added lithium hydroxide (20 mg, 0.47 mmol) in distilled water (1.5 mL). The resulting mixture was stirred at room temperature for 3 hours. After the reaction was completed, organic solvent was removed under reduced pressure. The residue was diluted with distilled water (50 mL) and acidified slowly with 0.5N HCl solution to pH=3. Extraction was performed three times with dichloromethane (3×50 mL). The extract was concentrated under reduced pressure to give the compound 4 (93.4 mg, 100%).

$^1$H NMR (600 MHz, CDCl$_3$) δ 7.35 (m, 2H), 7.30~7.24 (m, 7H), 4.89 (m, 4H), 6.78 (m, 3H), 6.64 (m, 1H), 5.91 (m, 2H), 5.65 (m, 1H), 5.21 (m, 2H), 5.07 (m, 2H), 4.89 (m, 1H), 4.67 (m, 2H), 4.28 (m, 2H), 4.18~4.12 (m, 6H), 3.93 (m, 8H), 3.85~3.82 (m, 5H), 3.72 (m, 2H), 3.65~3.54 (m, 20H), 3.34~3.32 (m, 4H), 2.82 (m, 2H), 2.56 (m, 1H), 2.44 (m, 2H), 0.90 (2s, 18H), 0.25 (2s, 12H)

LCB14-0597

To a solution of the compound 4 (90 mg, 0.045 mmol) in tetrahydrofuran (1.5 mL) were added 1N-ammonium acetate (1.2 mL) and 10% cadmium/lead couple (120 mg). The resulting mixture was stirred at room temperature for 3 hours. After the reaction was completed, ethyl acetate (50 mL) and distilled water (50 mL) were added. The thus-obtained organic layer was dried with anhydrous sodium sulfate and concentrated under reduced pressure. The residue was subjected to column chromatography to give the compound LCB14-0597 (16.4 mg, 26%).

EI-MS m/z: 1371(M$^+$)

2-20. Amino-Peg1-PBD Dimer (LCB14-0599)

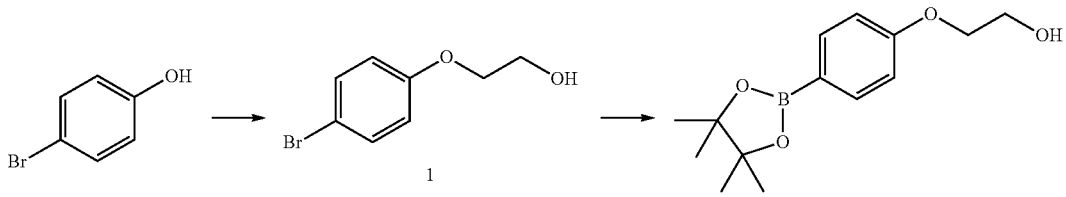

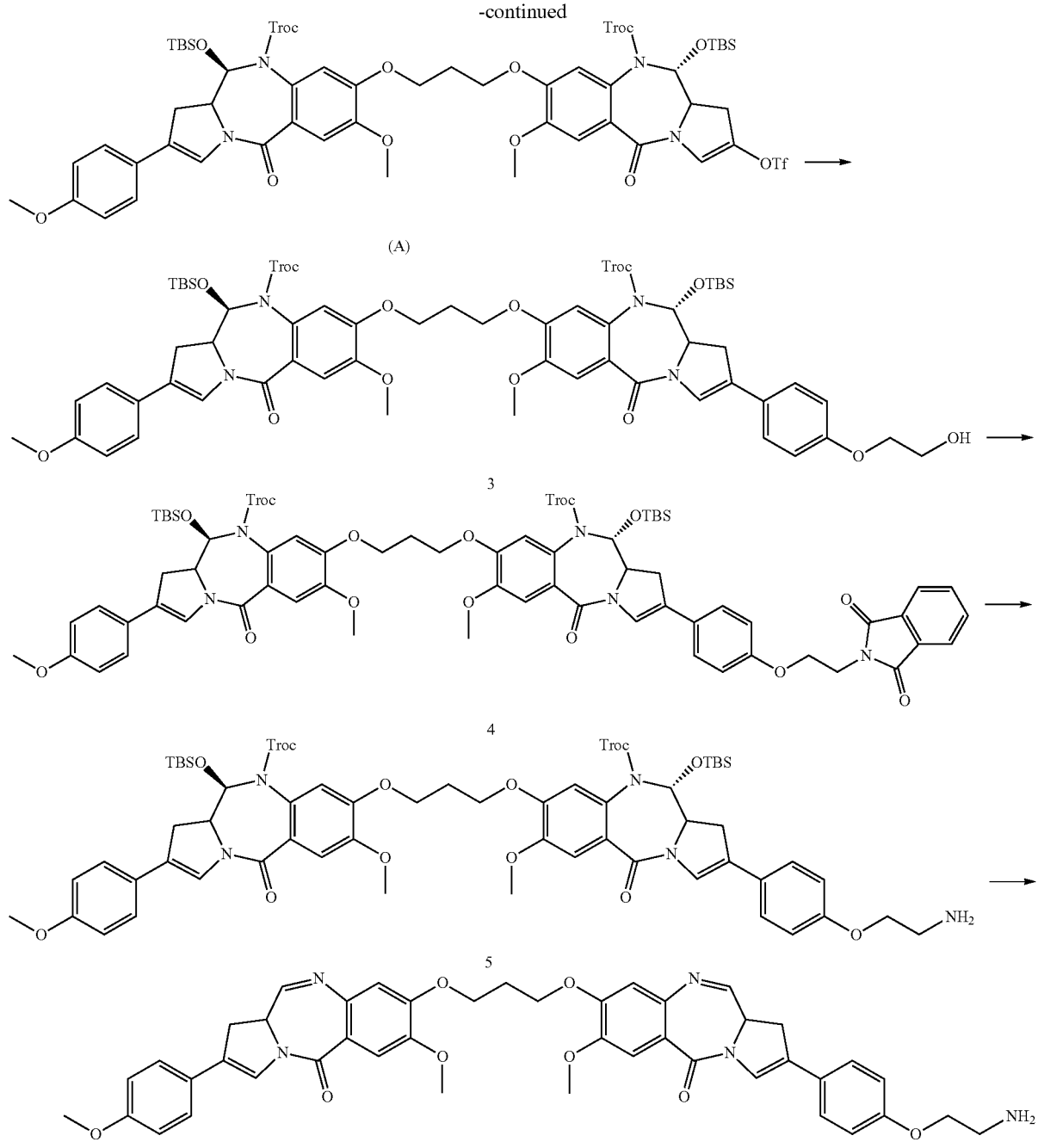

LCB14-0599

Compound 1

To a solution of 4-bromophenol (4.0 g, 23.1 mmol) in ethanol (18 mL) at room temperature were added sodium hydroxide (1.0 g, 25.40 mmol) and 2-bromoethanol (1.7 mL, 23.10 mmol). Ethyl acetate (500 mL) and water (200 mL) were added. The thus-obtained organic layer was concentrated under reduced pressure. The residue was subjected to column chromatography with ethyl acetate and hexane to give the compound 1 (4.3 g, 86%) in liquid form.

$^1$H NMR (600 MHz, CDCl$_3$) δ: 7.39-7.36 (m, 2H), 6.81-6.78 (m, 2H), 4.05-4.03 (m, 2H), 3.95 (t, J=4.2 Hz, 2H), 2.18 (bs, 1H).

Compound 2

To a solution of the compound 1 (0.3 g, 1.38 mmol) in 1,4-dioxane (10 mL) at room temperature were added bis(pinacolato)diboron (0.35 g, 1.38 mmol), potassium acetate (0.41 g, 4.14 mmol), and PdCl$_2$(dppf) (56 mg, 0.07 mmol). The resulting mixture was stirred at 70° C. for 12 hours, and then concentrated under reduced pressure. Filtration was performed with ethyl acetate. The filtered solution was concentrated under reduced pressure. The residue was subjected to column chromatography with ethyl acetate and hexane to give the compound 2 (0.36 g, 97%).

$^1$H NMR (600 MHz, CDCl$_3$) δ: 7.76-7.75 (m, 2H), 6.92-6.91 (m, 2H), 4.11 (t, J=4.2 Hz, 2H), 3.97-3.96 (m, 2H), 1.99 (bs, 1H), 1.33 (s, 12H).

Compound 3

A solution of the compound (A) (85 mg, 0.11 mmol), which was prepared according to the methods described in WO2006/111759, WO2010/043880 and WO2010/010347, the contents of each of these references are hereby incorporated by reference in their entirety, and the compound 2 (35 mg, 0.13 mmol) in toluene (2 mL) were added sodium carbonate (17 mg, 0.16 mmol), distilled water (1 mL), and ethanol (1 mL). After the resulting mixture was stirred for 5 minutes, Pd(TPP)$_4$ (22 mg, 0.02 mmol) was added. The resulting mixture was stirred for 2 hours. Ethyl acetate (10 mL) and water (10 mL) were added. The thus-obtained organic layer was concentrated under reduced pressure. The residue was subjected to column chromatography with ethyl acetate and hexane to give the compound 3 (79 mg, 53%) as a yellow solid.

$^1$H NMR (600 MHz, CDCl$_3$) δ: 7.36-7.35 (m, 2H), 7.32-7.25 (m, 6H), 6.92-6.89 (m, 4H), 6.78 (s, 2H), 5.92 (d, J=9.0 Hz, 2H), 5.22 (d, J=12.0 Hz, 2H), 4.30-4.28 (m, 2H), 4.17-4.10 (m, 6H), 3.98-3.94 (m, 4H), 3.94 (s, 6H), 3.83 (s, 3H), 3.37-3.32 (m, 2H), 2.85-2.82 (m, 2H), 2.46-2.44 (m, 2H), 1.98 (bs, 1H), 0.91 (s, 18H), 0.26 (2s, 12H).

EI-MS m/z: 1387(M$^+$)

Compound 4

To a solution of the compound 3 (77 mg, 0.06 mmol) in tetrahydrofuran (2 mL) at room temperature were sequentially added triphenylphosphine (18 mg, 0.07 mmol), phthalimide (10 mg, 0.07 mmol), and DIAD (13 ul, 0.07 mmol). The resulting mixture was stirred for 12 hours. Ethyl acetate (10 mL) and water (10 mL) were added. The thus-obtained organic layer was concentrated under reduced pressure. The residue was subjected to column chromatography with ethyl acetate and hexane to give the compound 4 (72 mg, 87%) as a yellow solid.

$^1$H NMR (600 MHz, CDCl$_3$) δ: 7.88-7.86 (m, 2H), 7.77-7.75 (m, 2H), 7.39-7.36 (m, 2H), 7.30-7.24 (m, 6H), 6.90-6.86 (m, 4H), 6.78 (d, J=1.8 Hz, 2H), 5.92-5.88 (m, 2H), 5.24-5.22 (m, 2H), 4.28-4.24 (m, 4H), 4.17-4.11 (m, 6H), 3.98-3.90 (m, 8H), 3.83 (s, 3H), 3.36-3.29 (m, 2H), 2.85-2.78 (m, 2H), 2.47-2.43 (m, 2H), 0.91 (d, J=1.8 Hz, 18H), 0.27-0.24 (m, 12H).

EI-MS m/z: 1516(M$^+$)

Compound 5

A solution of the compound 4 (70 mg, 0.05 mmol) in ethanol (2 mL) at room temperature was treated with hydrazine monohydrate (12 ul, 0.23 mmol). The resulting mixture was stirred at 60° C. for 5 hours. The solid was filtered off by using ethyl acetate (10 mL). The filtrate was concentrated under reduced pressure. The residue was subjected to column chromatography with dichloromethane and methanol to give the compound 5 (64 mg, 63%).

$^1$H NMR (600 MHz, CDCl$_3$) δ: 7.36-7.35 (m, 2H), 7.32-7.25 (m, 6H), 6.92-6.89 (m, 4H), 6.78 (s, 2H), 5.92 (d, J=9.0 Hz, 2H), 5.22 (d, J=12.0 Hz, 2H), 4.30-4.28 (m, 2H), 4.17-4.10 (m, 6H), 3.98-3.94 (m, 4H), 3.94 (s, 6H), 3.83 (s, 3H), 3.37-3.32 (m, 2H), 2.85-2.82 (m, 2H), 2.46-2.44 (m, 2H), 1.98 (bs, 1H), 0.91 (s, 18H), 0.26 (2s, 12H).

EI-MS m/z: 1386(M$^+$)

LCB14-0599 To a solution of the compound 5 (30 mg, 0.02 mmol) in tetrahydrofuran (2 mL) at room temperature were added 1N ammonium acetate solution (0.6 mL) and cadmium/lead couple (60 mg). The resulting mixture was stirred for 4 hours. Solid was filtered off by using ethyl acetate (10 mL). The filtrate was concentrated under reduced pressure. The residue was subjected to column chromatography with dichloromethane and methanol to give the compound LCB14-0599 (9.0 mg, 60%) as a yellow solid.

$^1$H NMR (600 MHz, CDCl$_3$, CD3OD_1drop) δ: 7.54-7.49 (m, 3H), 7.35-7.30 (m, 5H), 7.26 (s, 1H), 6.93-6.86 (m, 5H), 6.51 (s, 1H), 6.29 (s, 1H), 4.67-4.59 (m, 2H), 4.28-4.09 (m, 6H), 3.85 (s, 9H), 3.31-3.27 (m, 1H), 3.07-3.03 (m, 2H), 2.92-2.89 (m, 1H), 2.39-2.30 (m, 2H), 2.05-2.03 (m, 2H).

EI-MS m/z: 770(M$^+$)

2-21. Modified GPP Derivative Including Carbonyl Group (LCB14-0606)

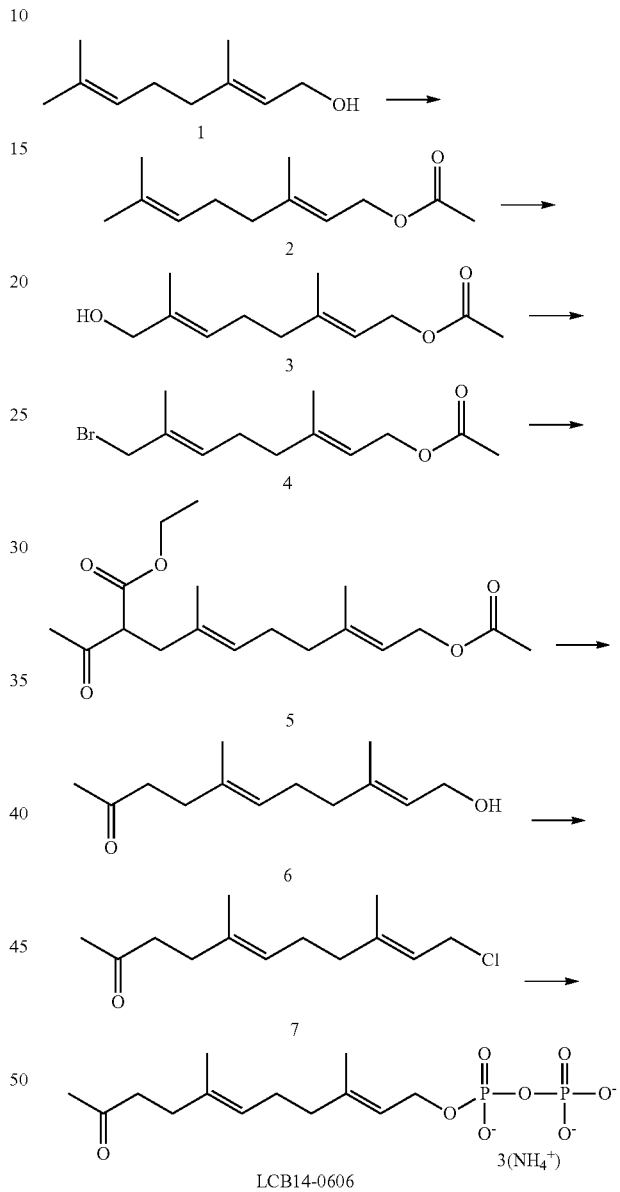

Compound 2

To a solution of the compound 1 (3 g, 19.45 mmol) in pyridine at room temperature were added acetic anhydride (7.9 mL, 77.8 mmol). The resulting mixture was stirred for 2 hours. Petroleum ether (100 mL) and 0.1N HCl (100 mL) were added. The thus-obtained organic layer was concentrated under reduced pressure to give the compound 2 (3.81 g, 100%) in aqueous form.

$^1$H NMR (600 MHz, CDCl$_3$) δ 5.35-5.33 (m, 1H), 5.08-4.58 (m, 1H), 4.59 (d, J=6.6 Hz, 2H), 2.11-2.03 (m, 4H), 2.05 (s, 3H), 1.70 (s, 3H), 1.68 (s, 3H), 1.60 (s, 3H)

Compound 3

To a solution of the compound 2 (3.81 g, 19.41 mml) in dichloromethane (30 mL) at room temperature were sequentially added selenium dioxide (65 mg, 0.58 mml) and 70% tert-butylhydroperoxide (6.72 mL, 48.52 mmol). The resulting mixture was stirred for 20 hours. After the reaction was completed, dichloromethane (100 mL) and water (100 mL) were added. The thus-obtained organic layer was concentrated under reduced pressure. The residue was subjected to column chromatography with ethyl acetate and hexane to give the compound 3 (1.8 g, 43%) as liquid.

$^1$H NMR (600 MHz, CDCl$_3$) δ 5.38-5.30 (m, 2H), 4.59 (d, J=7.2 Hz, 2H), 4.00-3.99 (d, J=6 Hz, 2H), 2.18-2.15 (m, 2H), 2.10-2.06 (m, 2H), 2.05 (s, 3H), 1.70 (s, 3H), 1.66 (s, 3H)

Compound 4

To a solution of the compound 3 (1.8 g, 8.48 mmol) in dichloromethane (18 mL) at 0° C. were added triphenylphosphine (3.33 g, 12.72 mmol) and carbon tetrabromide (3.37 g, 10.18 mmol). The resulting mixture was stirred at 0° C. for 4 hours. Dichloromethane (100 mL) and water (100 mL) were added. The thus-obtained organic layer was concentrated under reduced pressure. The residue was subjected to column chromatography with ethyl acetate and hexane to give the compound 4 (2.33 g, 100%) in liquid form.

$^1$H NMR (600 MHz, CDCl$_3$) δ 5.57-5.55 (m, 1H), 5.35-5.32 (m, 2H), 4.59 (d, J=7.2 Hz, 2H), 3.96 (s, 2H), 2.18-2.15 (m, 2H), 2.10-2.07 (m, 2H), 2.05 (s, 3H), 1.75 (s, 3H), 1.70 (s, 3H)

Compound 5

To a solution of the sodium hydride (348 mg, 8.71 mmol) in tetrahydrofuran (35 mL) at 0° C. was added drop-wise a solution of ethyl acetoacetate (1.85 mL, 14.52 mmol) in tetrahydrofuran (5 mL). After the resulting mixture was stirred at 0° C. for 30 minutes, the compound 4 (2 g, 7.26 mmol) dissolved in tetrahydrofuran (5 mL) was slowly added at 0° C. The resulting mixture was stirred at 80° C. for 4 hours. Ethyl acetate (80 mL) and water (80 mL) were added. The thus-obtained organic layer was concentrated under reduced pressure. The residue was subjected to column chromatography with ethyl acetate and hexane to give the compound 5 (1.56 g, 66%) as a white liquid.

$^1$H NMR (600 MHz, CDCl$_3$) δ 5.34-5.31 (m, 1H), 5.17-5.14 (m, 1H), 4.60-4.58 (m, 2H), 4.20-4.16 (m, 2H), 3.61 (t, J=7.2 Hz, 2H), 2.55-2.51 (m, 2H), 2.22 (s, 3H), 2.12-2.02 (m, 4H), 2.06 (s, 3H), 1.27 (t, J=7.2 Hz, 3H)

Compound 6

To a solution of the compound 5 (1.56 g, 4.81 mmol) in ethanol (20 mL) was added potassium hydroxide (2.16 g, 38.47 mmol) with ethanol (20 mL). The resulting mixture was stirred 100° C. for 4 hours, diluted with ethyl ether (100 mL) and 0.1N HCl solution (50 mL), and then neutralized with Na$_2$CO$_3$ solution. The thus-obtained organic layer was concentrated under reduced pressure. The residue was subjected to column chromatography to give the compound 6 (819 mg, 81%).

$^1$H NMR (600 MHz, CDCl$_3$) δ 5.39-5.37 (m, 1H), 5.09-5.07 (m, 1H), 4.15 (d, J=6.6 Hz, 2H), 2.53-2.51 (m, 2H), 2.27-2.24 (m, 2H), 2.13 (s, 3H), 2.12-2.09 (m, 2H), 2.04-2.01 (m, 2H), 1.66 (s, 3H), 1.60 (s, 3H)

Compound 7

To a solution of N-chlorosuccinimide (210 mg, 1.57 mmol) in dichloromethane (10 mL) under nitrogen atmosphere was slowly added dimethyl sulfide (126 µL, 1.71 mmol). The resulting mixture was stirred at 0° C. for 5 minutes. A solution of the compound 6 (300 mg, 1.43 mmol) dissolved in dichloromethane (5 mL) was added at 30° C. The resulting mixture was stirred at 0° C. for 2 hours. After the reaction was completed, n-pentane (100 mL) and water (100 mL) were added. The thus-obtained organic layer was concentrated under reduced pressure to give the compound 7 (325 mg, 99%).

$^1$H NMR (600 MHz, CDCl$_3$) δ 5.42 (m, 2H), 5.09 (m, 2H), 4.11 (d, J=8.4 Hz, 2H), 2.52 (m, 2H), 2.24 (m, 2H), 2.14 (s, 3H), 2.11 (m, 2H), 2.05 (m, 2H), 1.71 (s, 3H), 1.60 (s, 3H).

LCB14-0606

The compound LCB14-0606 was prepared according to the similar method described in JACS, 2010, 132(12), 4281, the contents of which are incorporated herein by reference in their entirety. To a solution of the compound 7 (320 mg, 1.40 mmol) in 7 mL of acetonitrile at room temperature was slowly added a solution of tris(tetrabutylammonium) hydrogen pyrophosphate (2.25 g, 2.80 mmol) in acetonitrile (7 ml). The resulting mixture was stirred for 1 hour. After the reaction was completed, the resulting mixture was concentrated under reduced pressure below at 25° C. The residue was subjected to column chromatography (packed BioRad AG 50W-X8 resin, hydrogen form, 15 g) with ammonia water:diluted water (V:V=3:1) and 25 mM ammonium bicarbonate:isopropyl alcohol (V:V=50:1) to give the compound LCB14-0606 (585 mg, 99%).

$^1$H NMR (600 MHz, D$_2$O) δ 5.42 (m, 1H), 5.16 (m, 1H), 4.46 (t, J=6.6 Hz, 2H), 2.66 (t, J=7.2 Hz, 2H), 2.25 (t, J=7.2 Hz, 2H), 2.19 (s, 3H), 2.14 (m, 2H), 2.06 (m, 2H), 1.69 (s, 3H), 1.60 (s, 3H)

Example 3: Prenylation of Ab(M)-CAAX 3-1. Prenylation methods

Prenylation of Ab(M)-CAAX was performed using NBD-GPP (Tris-ammonium[3,7-dimethyl-8-(7-nitro-benzo[1,2,5]oxadiazol-4-ylamino)-octa-2,6-diene-1]pyrophosphate) and FTase (#344146, Calbiochem, USA) or NBD-FPP (# LI-013, Jena Bioscience, Germany) and GGTase I (#345852, Calbiochem, USA).

The prenylation reaction was conducted at 30° C. for 3 hours by using a 50 mM Tris-HCl (pH 7.4) buffer solution containing 5 mM MgCl$_2$, 10 µM ZnCl$_2$, and 5 mM DTT. After the reaction was completed, SDS-PAGE analysis was made. An image analyzer (ChemiDoc XRS$^+$, BioRad, USA) was used to identify fluorescent protein band(s) to confirm that the prenylation reaction occurred.

3-2. Prenylation of Herceptin-HC-CAAX Using FTase and NBD-GPP

Herceptin-HC-GCVIM ("Herceptin-HC-GCVIM" disclosed as SEQ ID NO: 8), Herceptin-HC-G$_5$CVIM ("Herceptin-HC-G$_5$CVIM" disclosed as SEQ ID NO: 12) (not shown), Herceptin-HC-G$_7$CVIM ("Herceptin-HC-G$_7$CVIM" disclosed as SEQ ID NO: 16), and Herceptin-HC-G$_{10}$CVIM ("Herceptin-HC-G$_{10}$CVIM" disclosed as SEQ ID NO: 20) antibodies were prenylated using NBD-GPP and FTase in the method described above. Fluorescence was detected on protein band(s) corresponding to the heavy chain(s) (about 50K dalton) of the respective antibodies. This result confirmed that Herceptin-HC-CAAX antibodies, each having a spacer with various lengths, could be prenylated (FIG. 12).

3-3. Prenylation of Herceptin-LC-CAAX Using FTase and NBD-GPP

Figure 13:
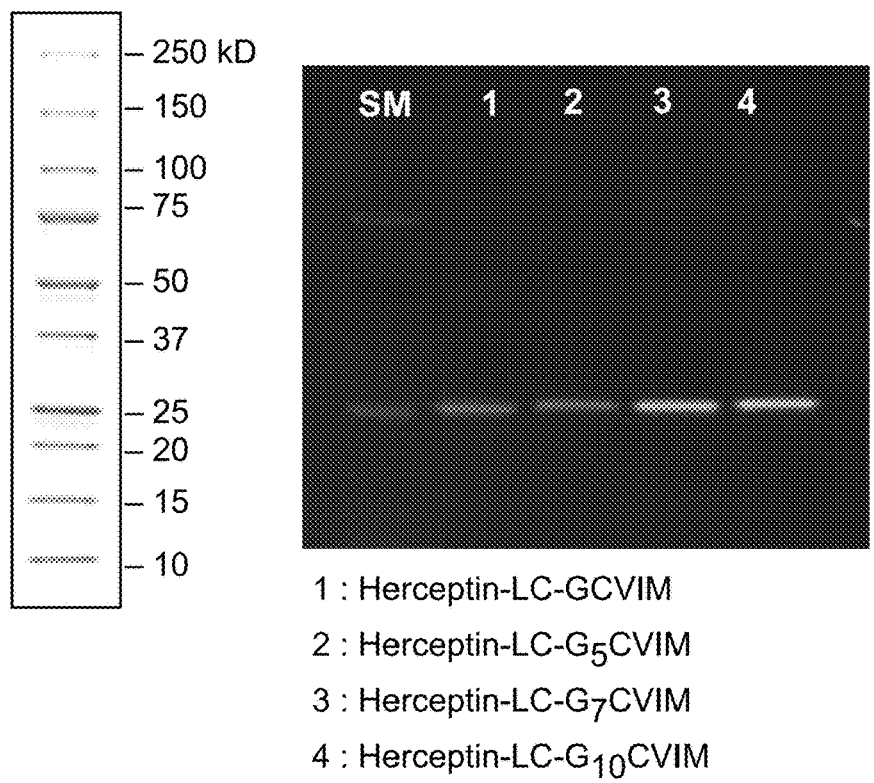
FIG. 13 shows an SDS-PAGE gel analyzing prenylation of Herceptin-LC-G$_n$CVIM ("G$_n$CVIM" disclosed as SEQ ID NO: 5) by using FTase and NBD-GPP. Figure discloses "G₅CVIM" as SEQ ID NO: 2, "G₇CVIM" as SEQ ID NO: 3, and "G₁₀CVIM" as SEQ ID NO: 4.

Herceptin-LC-GCVIM ("Herceptin-LC-GCVIM" disclosed as SEQ ID NO: 11), Herceptin-LC-G$_5$CVIM ("Herceptin-LC-G$_5$CVIM" disclosed as SEQ ID NO: 15), Herceptin-LC-G$_7$CVIM ("Herceptin-LC-G$_7$CVIM" disclosed as SEQ ID NO: 19), and Herceptin-LC-G$_{10}$CVIM ("Herceptin-LC-G$_{10}$CVIM" disclosed as SEQ ID NO: 23) antibodies were prenylated using NBD-GPP and FTase in the method described above. Fluorescence was detected on protein band(s) corresponding to the light chain(s) (about 25K dalton) of the respective antibodies. This result confirmed that Herceptin-LC-CAAX antibodies, each having a spacer with various lengths, could be prenylated (FIG. 13).

3-4. Prenylation of Anti cMET-HC-CAAX Using FTase and NBD-GPP

Figure 14:
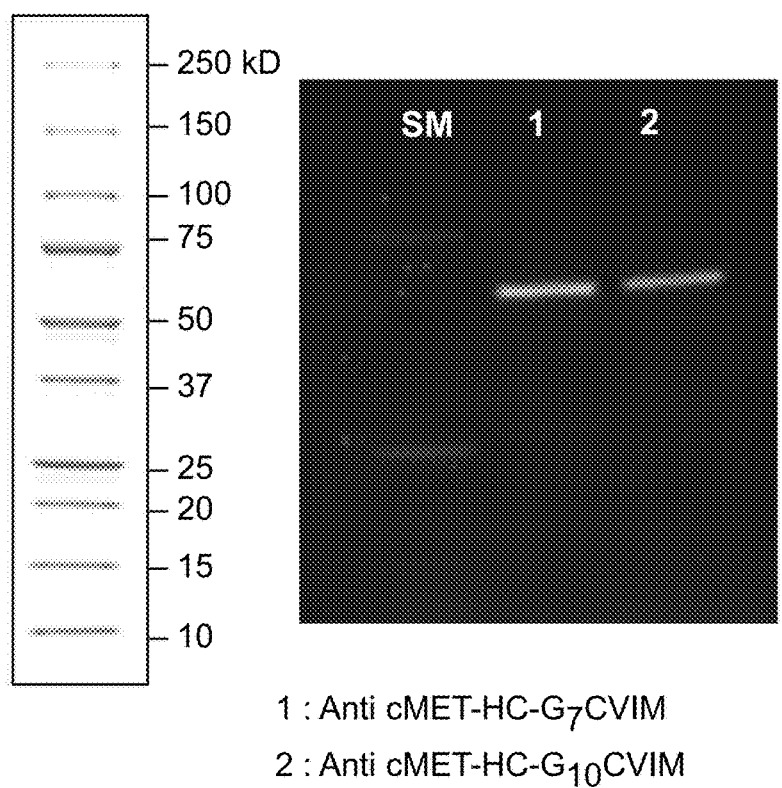
FIG. 14 shows an SDS-PAGE gel analyzing prenylation of cMET-HC-G$_n$CVIM ("G$_n$CVIM" disclosed as SEQ ID NO: 5) by using FTase and NBD-GPP. Figure discloses "G₇CVIM" as SEQ ID NO: 3 and "G₁₀CVIM" as SEQ ID NO: 4.

Anti cMET-HC-G$_7$CVIM ("G$_7$CVIM" disclosed as SEQ ID NO: 3) and anti cMET-HC-G$_{10}$CVIM ("G$_{10}$CVIM" disclosed as SEQ ID NO: 4) antibodies were prenylated using NBD-GPP and FTase in the method described above. Fluorescence was detected on protein band(s) corresponding to the heavy chain(s) (about 50K dalton) of the respective antibodies. This result confirmed that anti cMET-HC-CAAX antibodies, each having a spacer with various lengths, could be prenylated (FIG. 14).

3-5. Prenylation of Anti cMET-LC-CAAX Using FTase and NBD-GPP

Figure 15:
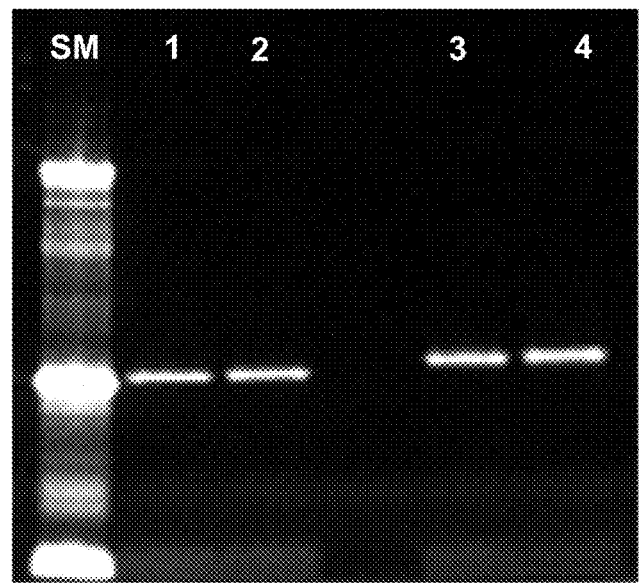
FIG. 15 shows an SDS-PAGE gel analyzing prenylation of cMET-LC-G$_n$CVIM ("G$_n$CVIM" disclosed as SEQ ID NO: 5) by using FTase and NBD-GPP. Figure discloses "G₇CVIM" as SEQ ID NO: 3 and "G₁₀CVIM" as SEQ ID NO: 4.

Anti cMET-LC-G$_7$CVIM ("G$_7$CVIM" disclosed as SEQ ID NO: 3) and anti cMET-LC-G$_{10}$CVIM ("G$_{10}$CVIM" disclosed as SEQ ID NO: 4) antibodies were prenylated using NBD-GPP and FTase in the method described above. Fluorescence was detected on protein band(s) corresponding to the light chain(s) (about 25K dalton) of the respective antibodies. This result confirmed that anti cMET-LC-CAAX antibodies, each having a spacer with various lengths, could be prenylated (FIG. 15).

3-6. Prenylation of Herceptin-HC-CAAX Using GGTase I and NBD-FPP

Figure 16:
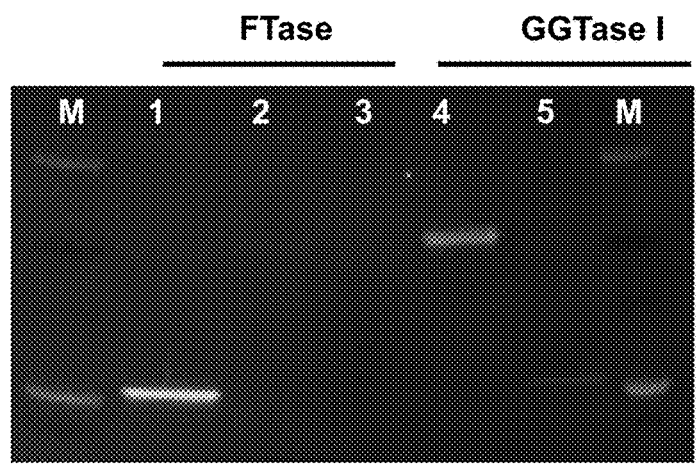
FIG. 16 shows an SDS-PAGE gel analyzing prenylation of Herceptin-HC-G₁₀CVLL ("Herceptin-HC-G₁₀CVLL" disclosed as SEQ ID NO: 24) and Herceptin-LC-G₁₀CVLL ("Herceptin-LC-G₁₀CVLL" disclosed as SEQ ID NO: 27) by using FTase/NBD-GPP or GGTase I/NBD-FPP. Figure discloses "G₇CVIM" as SEQ ID NO: 3 and "G₁₀CVLL" as SEQ ID NO: 6.

A Herceptin-HC-G$_{10}$CVLL ("Herceptin-HC-G$_{10}$CVLL" disclosed as SEQ ID NO: 24) antibody was prenylated using NBD-FPP and GGTase I in the method described above. Fluorescence was detected on a protein band corresponding to the heavy chain(s) (about 50K dalton) of the antibody that is connected with the CAAX-motif at the C-terminus via the G$_{10}$ (SEQ ID NO: 7) spacer. This result confirmed that Herceptin-HC-CAAX antibodies could be prenylated by GGTase I (FIG. 16).

3-7. Prenylation of Herceptin-LC-CAAX Using GGTase I and NBD-FPP

A Herceptin-LC-G$_{10}$CVLL ("Herceptin-LC-G$_{10}$CVLL" disclosed as SEQ ID NO: 27) antibody was prenylated using NBD-FPP and GGTase I in the method described above. Fluorescence was detected on a protein band corresponding to the light chain(s) (about 25K dalton) of the antibody that is connected with the CAAX-motif at the C-terminus via the G$_{10}$ (SEQ ID NO: 7) spacer. This result confirmed that Herceptin-LC-CAAX antibodies could be prenylated by GGTase I (FIG. 16).

3-8. Prenylation of Herceptin-LC-CAAX Using FTase and Isosubstrate

Herceptin-LC-G$_7$CVIM ("Herceptin-LC-G$_7$CVIM" disclosed as SEQ ID NO: 19)

A Herceptin-LC-G$_7$CVIM ("Herceptin-LC-G$_7$CVIM" disclosed as SEQ ID NO: 19) antibody was prenylated using LCB14-0512 and FTase in the method described above. In case where the prenylated Herceptin-LC-G$_7$CVIM ("Herceptin-LC-G$_7$CVIM" disclosed as SEQ ID NO: 19) antibody was subjected to LC/MS analysis in a reduction condition without treating PNGase F, it was predicted that the theoretical molecular weights of the heavy chain and the light chain would be 50,597 daltons and 24,480 daltons, respectively. As shown in FIG. 17, the experimental molecular weights of the heavy chain and the light chain were measured to be 50,600 daltons and 24,479 daltons, respectively. The difference between the theoretical molecular weight values and the experimental molecular weight values was within a standard error range. This result confirmed that the Herceptin-LC-G$_7$CVIM ("Herceptin-LC-G$_7$CVIM" disclosed as SEQ ID NO: 19) antibody was prenylated by FTase and an isosubstrate (LCB14-0512).

Herceptin-LC-G$_{10}$CVIM ("Herceptin-LC-G$_{10}$CVIM" disclosed as SEQ ID NO: 23) A Herceptin-LC-G$_{10}$CVIM ("Herceptin-LC-G$_{10}$CVIM" disclosed as SEQ ID NO: 23) antibody was prenylated using LCB14-0512 and FTase in the method described above. In the case where the prenylated HERCEPTIN-LC-G$_{10}$CVIM ("Herceptin-LC-G$_{10}$CVIM" disclosed as SEQ ID NO: 23) antibody was subjected to LC/MS analysis in a reduction condition without treating PNGase F, it was predicted that the theoretical molecular weights of the heavy chain and the light chain would be 50,596 daltons and 24,651 daltons, respectively. As shown in FIG. 18, the experimental molecular weights of the heavy chain and the light chain were measured to be 50,601 daltons and 24,651 daltons, respectively. The difference between the theoretical molecular weight values and the experimental molecular weight values was within a standard error range. This result confirmed that the Herceptin-LC-G$_{10}$CVIM ("Herceptin-LC-G$_{10}$CVIM" disclosed as SEQ ID NO: 23) antibody was prenylated by FTase and an isosubstrate (LCB14-0512).

Example 4: Drug Conjugation by Using Click Chemistry 4-1. Reoxidation of Prenylated Ab(M)-CAAX Diafiltration was performed to remove excess reagents in the prenylated Herceptin-LC-G$_7$CVIM ("Herceptin-LC-G$_7$CVIM" disclosed as SEQ ID NO: 19) prepared according to the above described method. The antibody was reoxidized using CuSO$_4$. Diafiltration was performed to remove CuSO$_4$.

4-2. Drug Conjugation of Ab(M)-CAAX Using Click Chemistry and Linker-Drug

Figure 19:
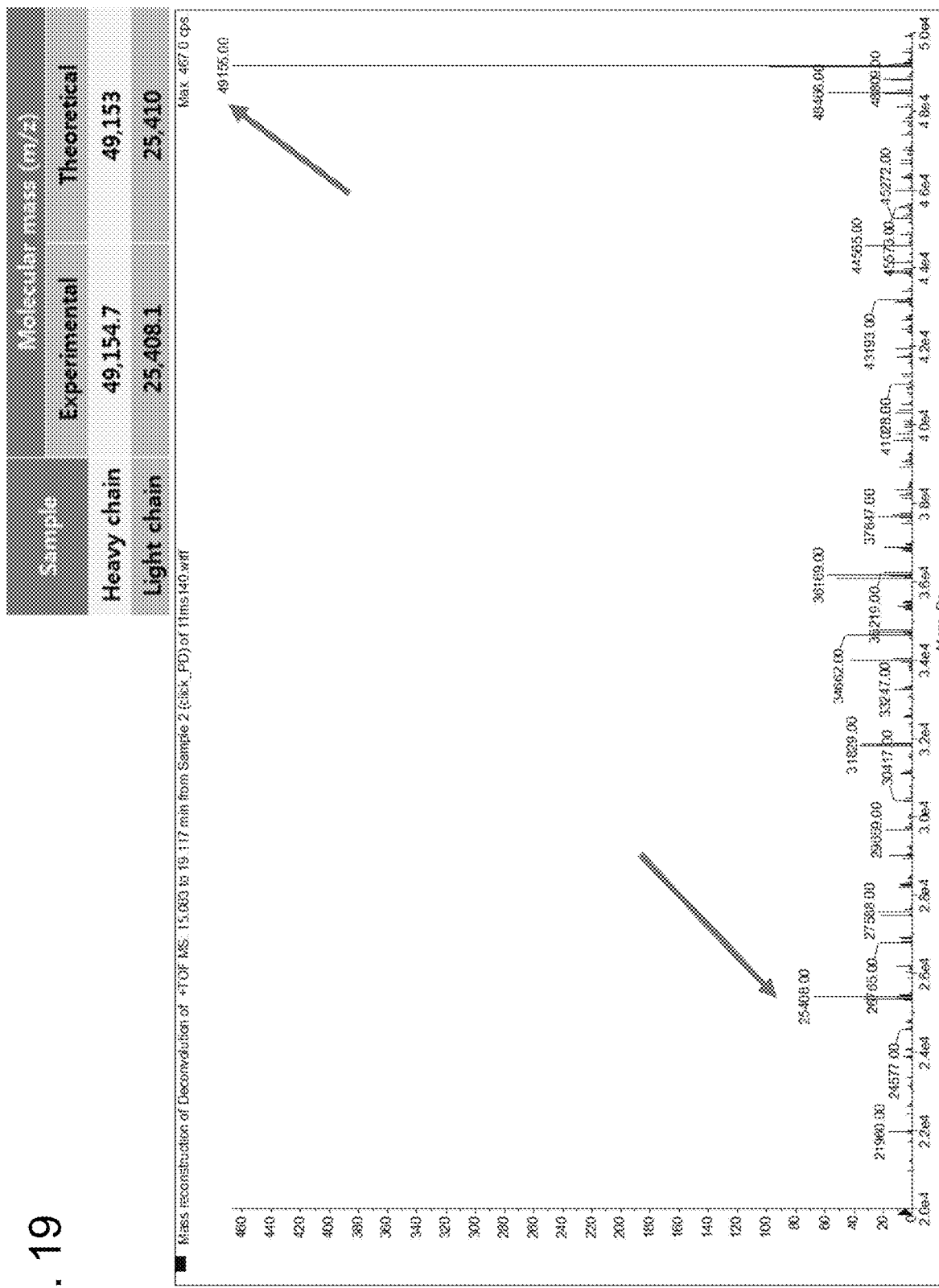
FIG. 19 shows the results from LC/MS and deconvoluted mass spectra analysis of LCB14-0104 (Herceptin-LC-G₇CVIM-NC-MMAF-Ome) ("G₇CVIM" disclosed as SEQ ID NO: 3).
Figure 26:
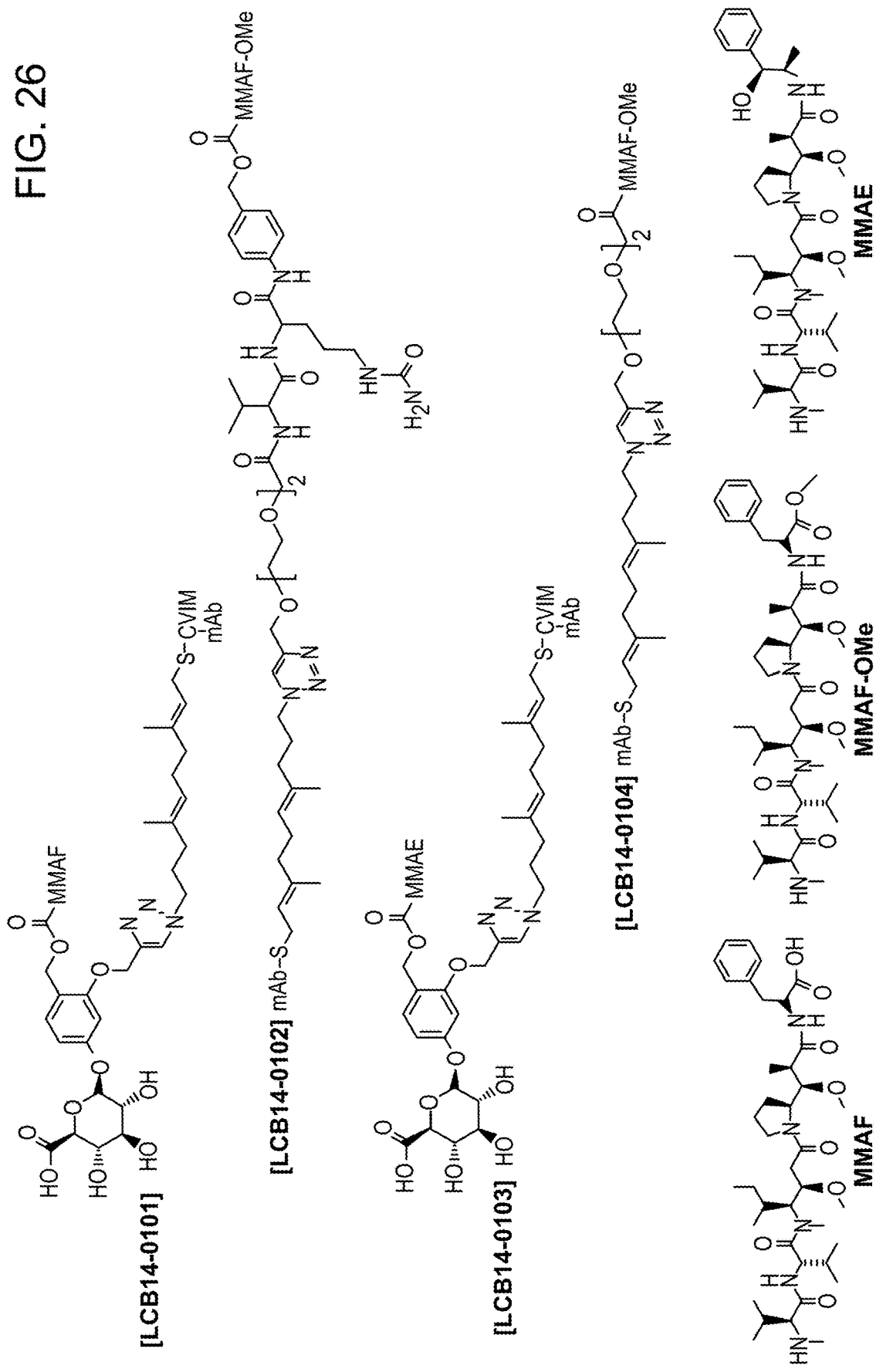
FIG. 26 shows the chemical structures of antibody-drug conjugates LCB14-0101, LCB14-0102, LCB14-0103, and LCB14-0104. Figure discloses "CVIM" as SEQ ID NO: 28.
Figure 27:
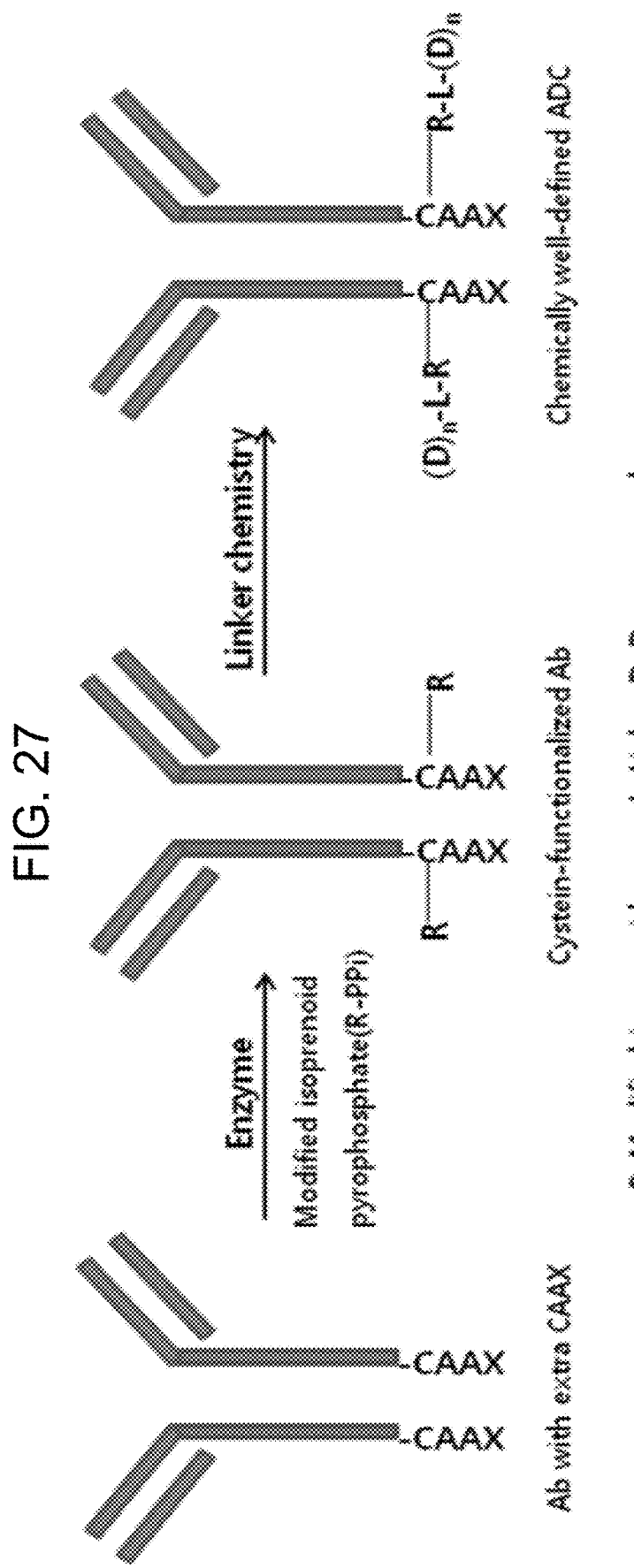
FIG. 27 is a schematic diagram depicting a process for preparing a protein-active agent conjugate by using an isoprenoid transferase and an isosubstrate thereof in which cysteine of the CAAX motif is alkylated.

Click chemistry reaction between the reoxidized, prenylated Herceptin-LC-G$_7$CVIM ("Herceptin-LC-G$_7$CVIM" disclosed as SEQ ID NO: 19) and the compound LCB14-0536 was performed for 10 minutes. The resulting conjugate (LCB14-0104) (FIG. 26) was subjected to LC/MS analysis. In the case where the antibody was subjected to LC/MS analysis in a reduction condition without treating PNGase F, it was predicted that the theoretical molecular weights of the heavy chain and the light chain would be 49,153 daltons and 25,410 daltons, respectively. As shown in FIG. 19, the experimental molecular weights of the heavy chain and the light chain were measured to be 49,154 daltons and 25,408 daltons, respectively. The difference between the theoretical molecular weight values and the experimental molecular weight values was within a standard error range. This result confirmed that the prenylated Herceptin-LC-G$_7$CVIM ("Herceptin-LC-G$_7$CVIM" disclosed as SEQ ID NO: 19) antibody formed a conjugate with a drug by click chemistry reaction.

4-3. Analysis of Herceptin-LC-CAAX-Drug Conjugates

The conjugate LCB14-0101 was subjected to hydrophobic interaction chromatography-high performance liquid chromatography with Ether-5PW column (7.5×75 mm, 10 rpm, Tosoh Bioscience, USA). 50 mM potassium phosphate buffer (pH 7.0) containing 1.5M ammonium sulfate was used as buffer A and 50 mM potassium phosphate buffer (pH 7.0) containing 20% isopropyl alcohol was used as buffer B. 90% A/10% B was held for 5 minutes. Elution was conducted using a linear gradient from 90% A/10% B to 10% A/90% B for the next 30 minutes. The flow rate and temperature were set as 0.8 mL/min and 25° C., respectively. The detection was followed at both 254 and 280 nm. Unmodified Herceptin-LC-G$_7$CVIM ("Herceptin-LC-G$_7$CVIM" disclosed as SEQ ID NO: 19) and prenylated Herceptin-LC-G$_7$CVIM ("Herceptin-LC-G$_7$CVIM" disclosed as SEQ ID NO: 19) were used as controls. The retention times of the unmodified Herceptin-LC-G$_7$CVIM ("Herceptin-LC-G$_7$CVIM" disclosed as SEQ ID NO: 19), the prenylated Herceptin-LC-G$_7$CVIM ("Herceptin-LC-G$_7$CVIM" disclosed as SEQ ID NO: 19), and the conjugate LCB14-0101 were 9.6, 11.7, and 12.4 minutes (FIG. 20), respectively.

Example 5: Antiproliferation of ADC 5-1. Cell Lines

Commercially available human breast cancer cell lines MCF-7 (HER2 negative to normal), MDA-MB-468 (HER2 negative), and SK-BR-3 (HER2 positive) were used. The cell lines were cultured according to recommended specifications provided with the commercially available cell lines.

5-2. Test Samples

As an antibody, a commercially available Herceptin_antibody and Herceptin-LC-G$_7$CVIM ("Herceptin-LC-G$_7$CVIM" disclosed as SEQ ID NO: 19) were used. As a drug, LCB14-0537 (MMAF), LCB14-0508 (MMAF-OMe), and LCB14-0562 (MMAE) were used. As a protein-active agent conjugate, LCB14-0101, LCB14-0102, and LCB14-0103 (FIG. 26) were used. The Herceptin-LC-G$_7$CVIM ("Herceptin-LC-G$_7$CVIM" disclosed as SEQ ID NO: 19) was prenylated using LCB14-0512. The prenylated Herceptin-LC-G$_7$CVIM ("Herceptin-LC-G$_7$CVIM" disclosed as SEQ ID NO: 19) was subjected to click reaction using LCB14-0592 to conjugate β-glucuronide linker(BG)-MMAF, thereby preparing LCB14-0101. In addition, the prenylated Herceptin-LC-G$_7$CVIM ("Herceptin-LC-G$_7$CVIM" disclosed as SEQ ID NO: 19) was subjected to click reaction using LCB14-0589 to conjugate Val-Cit linker (VC)-MMAF-OMe, thereby preparing LCB14-0102. Further, the prenylated Herceptin-LC-G$_7$CVIM ("Herceptin-LC-G$_7$CVIM" disclosed as SEQ ID NO: 19) was subjected to click reaction by using LCB14-0598 to conjugate β-glucuronide linker(BG)-MMAE, thereby preparing LCB14-0103.

5-3. Test Methods

Anti-proliferation activities of the antibodies, drugs, and conjugates with regard to the cancer cell lines were measured. The cells were plated in 96-well, tissue culture plates at $1 \times 10^4$ cells per well. After 24 hour incubation, the antibodies, drugs, and conjugates were added in various concentrations. The number of viable cells after 72 hours were counted using SRB dye. Absorbance was measured at 540 nm using SpectraMax 190 (Molecular Devices, USA).

5-4. Test Results

LCB14-0101 (Herceptin-LC-G$_7$CVIM-BG-MMAF) ("G$_7$CVIM" disclosed as SEQ ID NO: 3)

Figure 21:
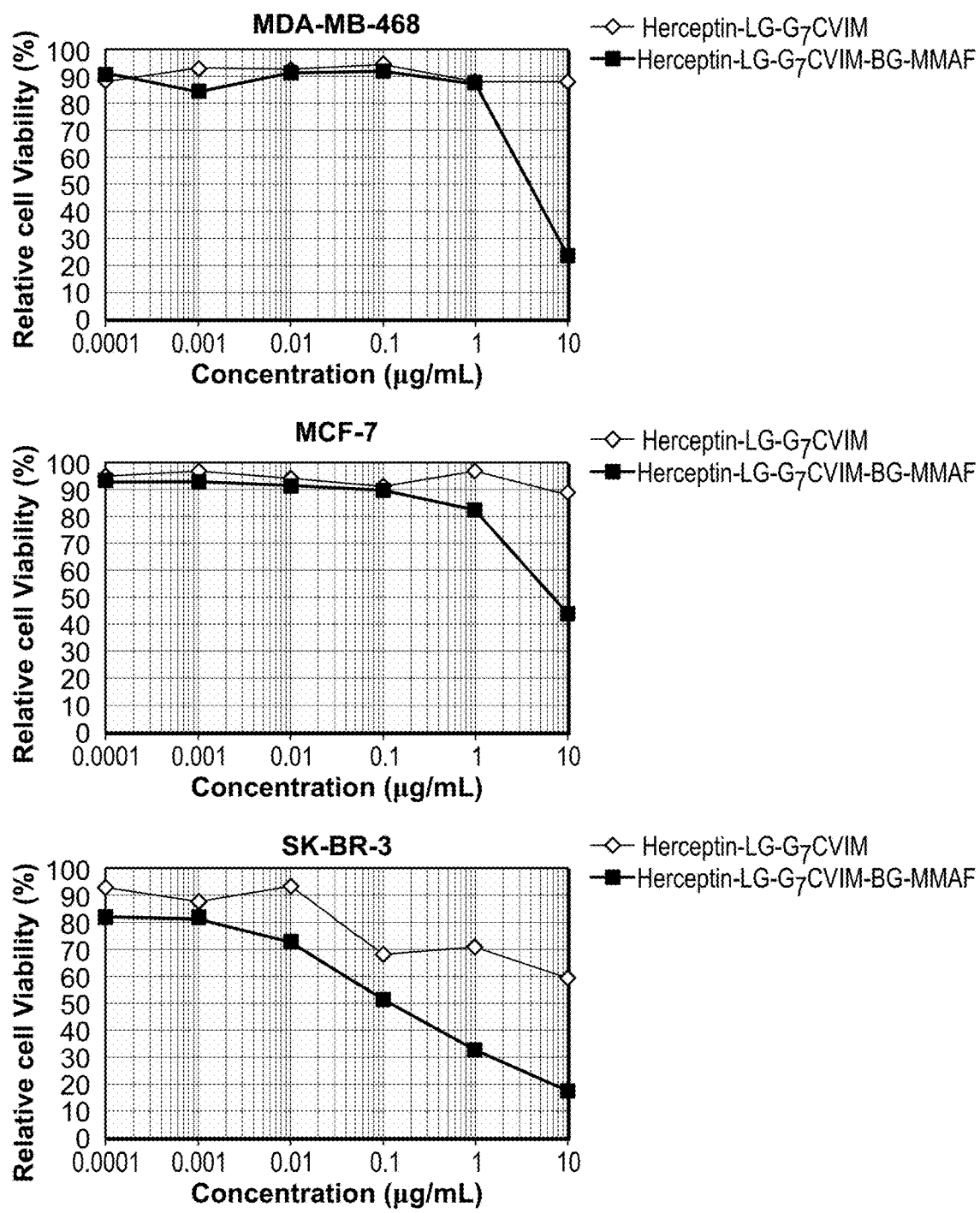
FIG. 21 shows the results from an anti-proliferation assay of LCB14-0101 (Herceptin-LC-G₇CVIM-BG-MMAF) ("G₇CVIM" disclosed as SEQ ID NO: 3) with breast cancer cell lines MCF-7, MDA-MB-468, and SK-BR-3.

Herceptin-LC-G$_7$CVIM ("Herceptin-LC-G$_7$CVIM" disclosed as SEQ ID NO: 19) had an IC$_{50}$ of 10 μg/mL or higher with MCF-7, MDA-MB-468, and SK-BR-3. LCB14-0101 (MMAF conjugate) had an IC$_{50}$ of 8.09 μg/mL and 4.18 μg/mL with MCF-7 and MDA-MB-468, respectively, which expresses no or low level of HER2, whereas it had an IC$_{50}$ of 0.11 μg/mL with SK-BR-3, which overexpresses HER2. In addition to its excellent inhibitory activity, LCB14-0101 is about 40-80 times more selective than Herceptin-LC-G$_7$CVIM ("Herceptin-LC-G$_7$CVIM" disclosed as SEQ ID NO: 19). Accordingly, it is confirmed that LCB14-0101 has both cytotoxic drug potency and anti HER2 selectivity (FIG. 21).

LCB14-0102 (Herceptin-LC-G$_7$CVIM-VC-MMAF-OM) ("G$_7$CVIM" Disclosed as SEQ ID NO: 3)

Figure 22:
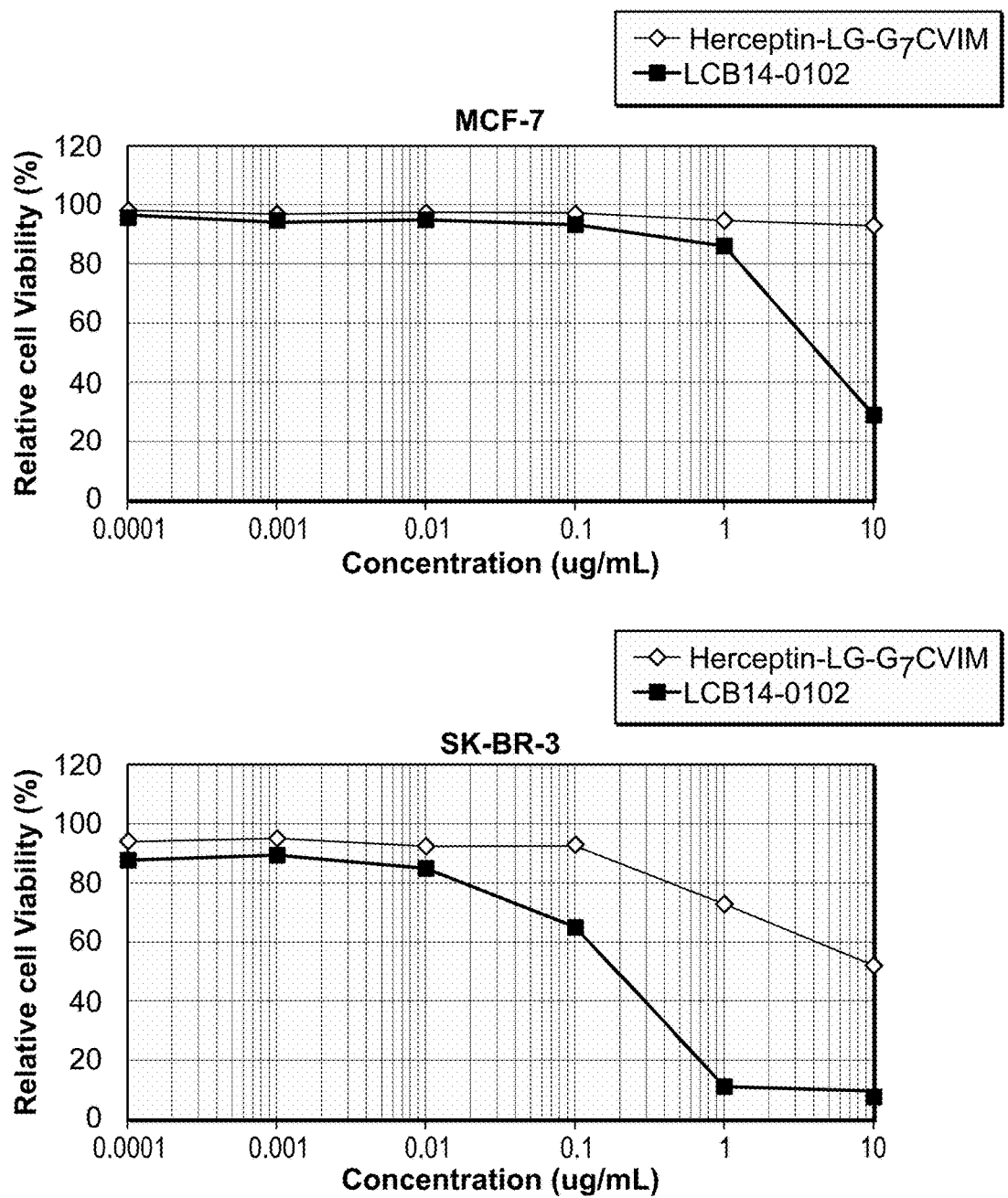
FIG. 22 shows the results from an anti-proliferation assay of LCB14-0102 (Herceptin-LC-G₇CVIM-VC-MMAF-OMe) ("G₇CVIM" disclosed as SEQ ID NO: 3) with breast cancer cell lines MCF-7 and SK-BR-3.

Herceptin-LC-G$_7$CVIM ("Herceptin-LC-G$_7$CVIM" disclosed as SEQ ID NO: 19) had an IC$_{50}$ of 10 μg/mL with MCF-7 and SK-BR-3. LCB14-0102 (MMAF-OMe conjugate) had an IC$_{50}$ of 4.38 μg/mL with MCF-7, whereas had an IC$_{50}$ of 0.15 μg/mL with SK-BR-3. In addition to its excellent inhibitory activity, LCB14-0102 is about 30 times more selective than Herceptin-LC-G$_7$CVIM ("Herceptin-LC-G$_7$CVIM" disclosed as SEQ ID NO: 19). Accordingly, it is confirmed that LCB14-0102 has both cytotoxic drug potency and anti HER2 selectivity (FIG. 22).

LCB14-0103 (Herceptin-LC-G$_7$CVIM-BG-MMAE) ("G$_7$CVIM" Disclosed as SEQ ID NO: 3)

Figure 23:
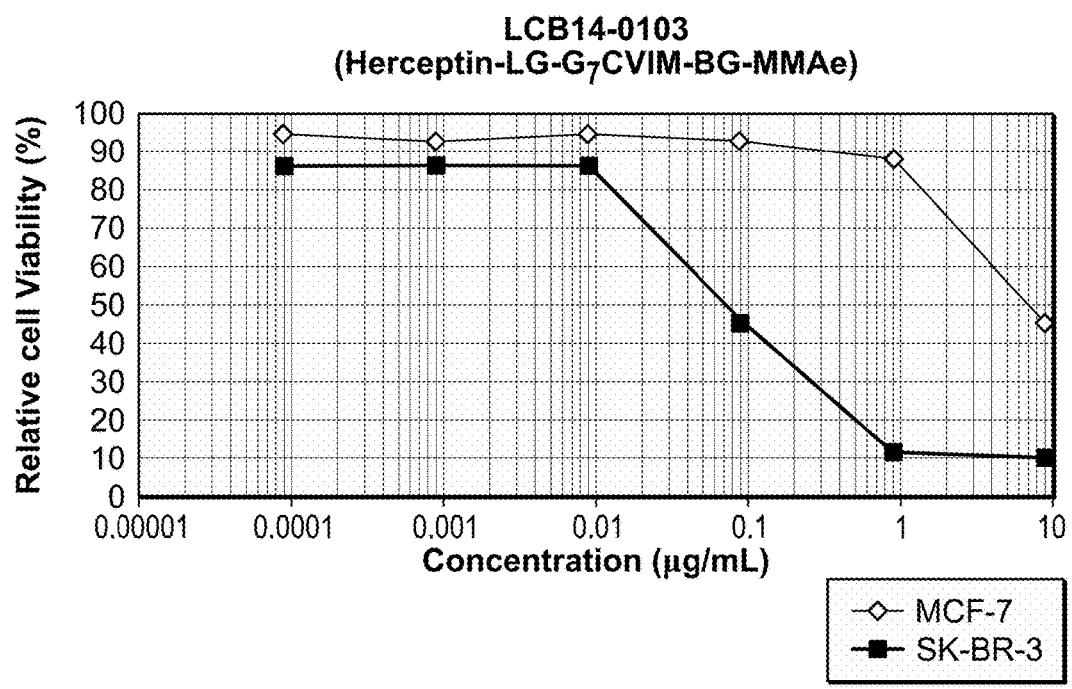
FIG. 23 shows the results from an anti-proliferation assay of LCB14-0103 (Herceptin-LC-G₇CVIM-BG-MMAE) ("G₇CVIM" disclosed as SEQ ID NO: 3) with breast cancer cell lines MCF-7 and SK-BR-3.
Figure 24:
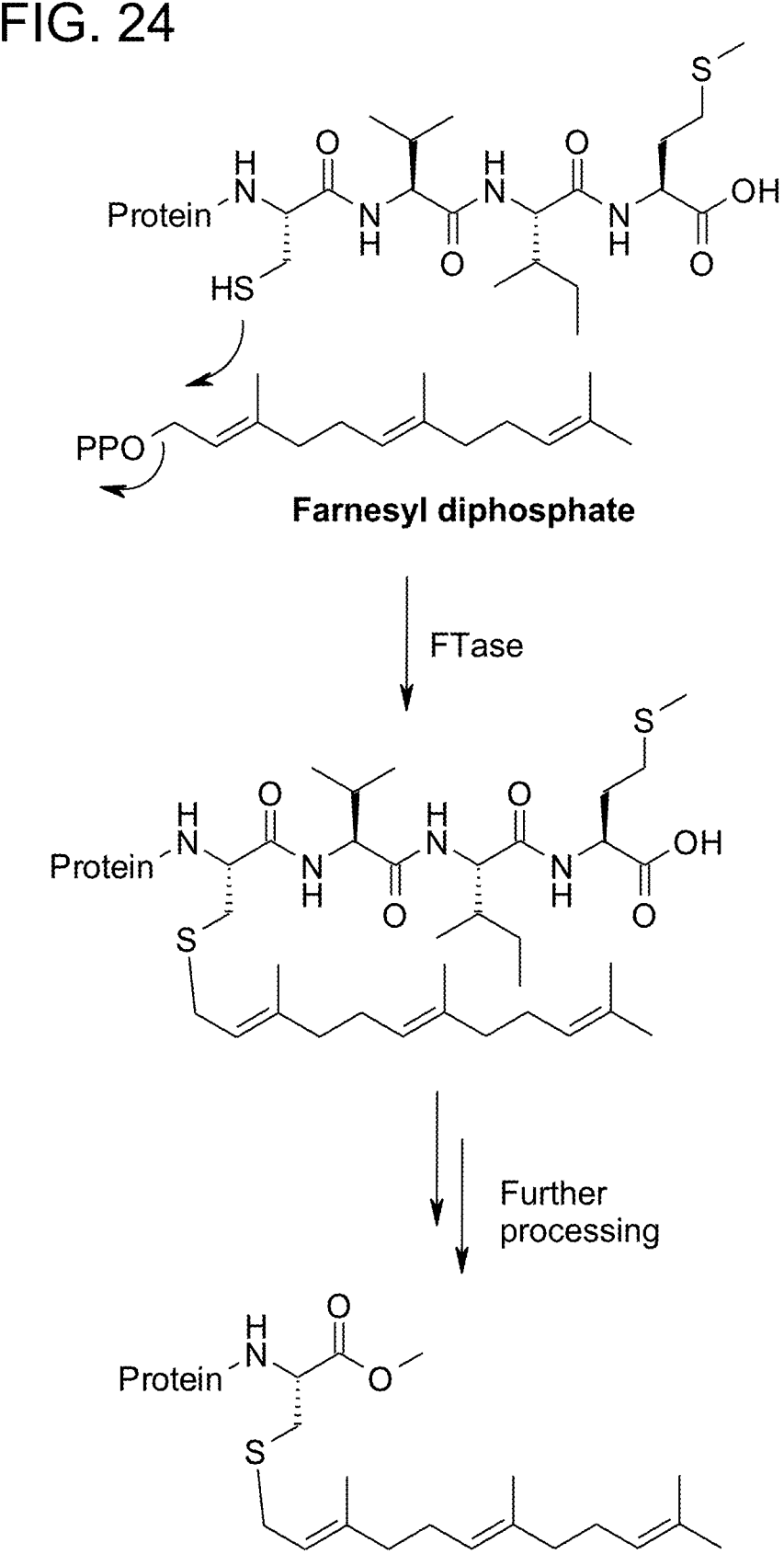
FIG. 24 shows a process of posttranslational modification of a protein (C-terminal CVIM (SEQ ID NO: 28)).

LCB14-0103 (MMAE conjugate) had an IC$_{50}$ of 7.25 μg/mL with MCF-7, whereas it had an IC$_{50}$ of 0.072 μg/mL with SK-BR-3. In addition to its excellent inhibitory activity, LCB14-0103 is about 100 times more selective than Herceptin-LC-G$_7$CVIM ("Herceptin-LC-G$_7$CVIM" disclosed as SEQ ID NO: 19). Accordingly, it is confirmed that LCB14-0103 has both cytotoxic drug potency and anti HER2 selectivity (FIG. 23).

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed as new and desired to be protected by Letters Patent of the United States is:

1. An antibody-active agent conjugate comprising:
   (a) a full-length antibody comprising two immunoglobulin heavy chains and two immunoglobulin light chains;
   (b) at least one amino acid motif having an amino acid sequence CAAX, wherein C represents cysteine, A represents an aliphatic amino acid, and X represents an amino acid that determines a substrate specificity of the isoprenoid transferase, directly or indirectly linked to a carboxy terminus of a heavy chain or light chain of the antibody, wherein the amino acid motif is recognizable by an isoprenoid transferase;
   (c) an isosubstrate directly linked to a cysteine moiety of the at least one amino acid motif, wherein the isosubstrate contains at least one isoprenoid unit and is recognizable by the isoprenoid transferase; and
   (d) at least one active agent, wherein the active agent is a drug, and the drug is directly or indirectly linked to the isosubstrate.

2. The conjugate of claim 1, wherein the antibody is a polyclonal antibody, a monoclonal antibody, a multispecific antibody, a bispecific antibody, a chimeric antibody, a humanized antibody, or a human antibody.

3. The antibody-active agent conjugate of claim 1, wherein the amino acid motif is directly or indirectly linked to the carboxy terminus of an immunoglobulin heavy chain.

4. The antibody-active agent conjugate of claim 1, wherein the amino acid motif is directly or indirectly linked to the carboxy terminus of an immunoglobulin light chain.

5. The antibody-active agent conjugate of claim 1, wherein a second amino acid motif is directly or indirectly linked to a second carboxy terminus.

6. The antibody-active agent conjugate of claim 1, wherein the at least one amino acid motif is indirectly linked to the carboxy terminus of the heavy chain or the light chain via a spacer group.

7. The conjugate of claim 6, wherein the spacer group comprises at least one amino acid.

8. The conjugate of claim 6, wherein the spacer group comprises at least one glycine.

9. The antibody-active agent conjugate of claim 8, wherein the spacer group comprises seven consecutive glycine residues.

10. The antibody-active agent conjugate of claim 1, wherein the isosubstrate is indirectly linked to the at least one active agent via at least one linker.

11. The antibody-active agent conjugate of claim 10, wherein the linker is a linear linker.

12. The antibody-active agent conjugate of claim 11, wherein the linear linker is directly linked to the at least one active agent.

13. The antibody-active agent conjugate of claim 10, wherein the linker is a linker having branches.

14. The antibody-active agent conjugate of claim 13, wherein one or more of the branches are directly linked to at least one of the active agents.

15. The antibody-active agent conjugate of claim 13, wherein at least two of the branches are directly linked to different active agents.

16. The antibody-active agent conjugate of claim 10, wherein the linker is a cleavable linker.

17. The antibody-active agent conjugate of claim 16, wherein the linker is a chemically cleavable linker, an enzymatically cleavable linker, a hydrolysable linker, or a combination thereof.

18. The antibody-active agent conjugate of claim 17, wherein the cleavable linker is an enzymatically cleavable linker and the enzymatically cleavable linker contains a peptide that can be cleaved by cathepsin B or a glucuronide that can be cleaved by β-glucuronidase.

19. The antibody-active agent conjugate of claim 1, wherein the drug is erlotinib, bortezomib, fulvestrant, sunitinib, letrozole, imatinib mesylate, PTK787/ZK 222584, oxaliplatin, 5-fluorouracil, leucovorin, rapamycin, lapatinib, lonafarnib, sorafenib, gefitinib, Tyrphostin AG1478, thiotepa, cyclophosphamide, busulfan, improsulfan, piposulfan, benzodopa, carboquone, meturedopa, uredopa, ethylenimine, altretamine, triethylenemelamine, triethylene phosphoramide, triethylene thiophosphoramide, trimethylol melamine, bullatacin, bullatacinone, camptothecin topotecan, bryostatin, callystatin, adozelesin, carzelesin, bizelesin, cryptophycin 1, cryptophycin 8, dolastatin, duocarmycin, eleutherobin, pancratistatin, sarcodictyin, spongistatin, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, calicheamicin, calicheamicin gamma 1I, calicheamicin omega I1, dynemicin, dynemicin A, clodronate, esperamicin, neocarzinostatin chromophore, aclacinomysins, actinomycin, anthramycin, azaserine, bleomycins, cactinomycin, carabicin, carminomycin, carzinophilin, chromomycins, dactinomycin, daunorubicin, 6-diazo-5-oxo-L-norleucine, doxorubicin, morpholino-doxorubicin, cyanomorpholino-doxorubicin, 2-pyrrolino-doxorubucin, liposomal doxorubicin, deoxydoxorubicin, epirubicin, esorubicin, marcellomycin, mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin, zorubicin, 5-fluorouracil, denopterin, methotrexate, pteropterin, trimetrexate, fludarabine, 6-mercaptopurine, thiamiprine, tioguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatraxate, demecolcine, diaziquone, elfornithine, elliptinium acetate, etoglucid, gallium nitrate, hydroxyurea, lentinan, lonidainine, maytansine, ansamitocins, mitoguazone, mitoxantrone, mopidanmo, nitraerine, pentostatin, phenamet, pirarubicin, losoxantrone, 2-ethylhydrazide, procarbazine, polysaccharide-k, razoxane, rhizoxin, sizofiran, spirogermanium, tenuazonic acid, triaziquone, 2,2',2''-trichlorotriethylamine, verracurin A, roridin A, anguidine, urethane, vindesine, dacarbazine, mannomustine, mitobronitol, mitolactol, pipobroman, gacytosine, arabinoside ('Ara-C'), cyclophosphamide, thiotepa, paclitaxel, doxetaxel, chlorambucil, gemcitabine, 6-thioguanine, mercaptopurine, cisplatin, carboplatin, vinblastine, platinum, etoposide, ifosfamide, mitoxantrone, vincristine, vinorelbine, novantrone, teniposide, edatrexate, daunomycin, aminopterin, ibandronate, CPT-11, topoisomerase inhibitor RFS 2000, difluoromethylornithine (DFMO), retinoic acid, capecitabine, or a pharmaceutically acceptable salt, solvate, or acid of any of the foregoing.

20. The antibody-active agent conjugate of claim 1, wherein the amino acid motif is CVIM (SEQ ID NO:28) or CVLL (SEQ ID NO:29).

21. The antibody-active agent conjugate of claim 1, wherein the drug is directly or indirectly linked to the isosubstrate by an oxime.

22. The antibody-active agent conjugate of claim 10, wherein the linker is a non-cleavable linker.

23. The antibody-active agent conjugate of claim 11, wherein the linear linker is directly linked to the at least two different active agents.

\* \* \* \* \*

SEQUENCE LISTING

```
<160> NUMBER OF SEQ ID NOS: 29

<210> SEQ ID NO 1
<211> LENGTH: 9
<212> TYPE: PRT
<213> ORGANISM: Artificial Sequence
```

```
<220> FEATURE:
<223> OTHER INFORMATION: Synthetic Peptide

<400> SEQUENCE: 1

Gly Gly Gly Gly Gly Cys Val Ile Met
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Gly Cys Val Ile Met
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic peptide

<400> SEQUENCE: 3

Gly Gly Gly Gly Gly Gly Gly Cys Val Ile Met
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide

<400> SEQUENCE: 4

Gly Gly Gly Gly Gly Gly Gly Gly Gly Gly Cys Val Ile Met
1               5                   10

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Gly Cys Val Ile Met
1               5

<210> SEQ ID NO 6
<211> LENGTH: 14
<212> TYPE: PRT
<213> ORGANISM: Artificial Sequence
<220> FEATURE:
<223> OTHER INFORMATION: Synthetic peptide

<400> SEQUENCE: 6

Gly Gly Gly Gly Gly Gly Gly Gly Gly Gly Cys Val Leu Leu
1               5                   10

<210> SEQ ID NO 7
<211> LENGTH: 10
<212> TYPE: PRT
<213> ORGANISM: Artificial Sequence
<220> FEATURE:
```

<223> OTHER INFORMATION: Synthetic peptide

<400> SEQUENCE: 7

Gly Gly Gly Gly Gly Gly Gly Gly Gly
1               5                   10

<210> SEQ ID NO 8
<211> LENGTH: 455
<212> TYPE: PRT
<213> ORGANISM: Artificial Sequence
<220> FEATURE:
<223> OTHER INFORMATION: Synthetic polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Gly Cys Val Ile Met
    450                 455

<210> SEQ ID NO 9
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65              70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
```

```
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 11
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Cys Val Ile Met
    210                 215

<210> SEQ ID NO 12
<211> LENGTH: 459
<212> TYPE: PRT
<213> ORGANISM: Artificial Sequence
<220> FEATURE:
<223> OTHER INFORMATION: Synthetic polypeptide

<400> SEQUENCE: 12

Glu Val Gln Leu Val Glu Ser Gly Gly Gly Leu Val Gln Pro Gly Gly

```
1               5                   10                  15
Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
                35                  40                  45

Ala Arg Ile Tyr Pro Thr Asn Gly Tyr Thr Arg Tyr Ala Asp Ser Val
                50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
                210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430
```

Glu Ala Leu His Asn His Tyr Thr Gln Lys Ser Leu Ser Leu Ser Pro
            435                 440                 445

Gly Lys Gly Gly Gly Gly Gly Cys Val Ile Met
    450                 455

<210> SEQ ID NO 13
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val

-continued

```
                50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
               100                 105                 110

Gly Thr Leu Val Thr Val Ser Ala Ser Thr Lys Gly Pro Ser Val
               115                 120                 125

Phe Pro Leu Ala Pro Ser Ser Lys Ser Thr Ser Gly Gly Thr Ala Ala
               130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
               165                 170                 175

Leu Gln Ser Ser Gly Leu Tyr Ser Leu Ser Ser Val Val Thr Val Pro
               180                 185                 190

Ser Ser Ser Leu Gly Thr Gln Thr Tyr Ile Cys Asn Val Asn His Lys
               195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
               245                 250                 255

Ser Arg Thr Pro Glu Val Thr Cys Val Val Val Asp Val Ser His Glu
               260                 265                 270

Asp Pro Glu Val Lys Phe Asn Trp Tyr Val Asp Gly Val Glu Val His
               275                 280                 285

Asn Ala Lys Thr Lys Pro Arg Glu Glu Gln Tyr Asn Ser Thr Tyr Arg
               290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
               325                 330                 335

Lys Thr Ile Ser Lys Ala Lys Gly Gln Pro Arg Glu Pro Gln Val Tyr
               340                 345                 350

Thr Leu Pro Pro Ser Arg Asp Glu Leu Thr Lys Asn Gln Val Ser Leu
               355                 360                 365

Thr Cys Leu Val Lys Gly Phe Tyr Pro Ser Asp Ile Ala Val Glu Trp
               370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
               405                 410                 415

Lys Ser Arg Trp Gln Gln Gly Asn Val Phe Ser Cys Ser Val Met His
               420                 425                 430

Glu Ala Leu His Asn His Tyr Thr Gln Lys Ser Leu Ser Leu Ser Pro
               435                 440                 445

Gly Lys
450
```

<210> SEQ ID NO 15

```
<211> LENGTH: 223
<212> TYPE: PRT
<213> ORGANISM: Artificial Sequence
<220> FEATURE:
<223> OTHER INFORMATION: Synthetic polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Cys Val Ile Met
    210                 215                 220

<210> SEQ ID NO 16
<211> LENGTH: 461
<212> TYPE: PRT
<213> ORGANISM: Artificial Sequence
<220> FEATURE:
<223> OTHER INFORMATION: Synthetic polypeptide

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
```

```
                100                 105                 110
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Gly Gly Cys Val Ile Met
450                 455                 460

<210> SEQ ID NO 17
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 17

Asp Ile Gln Met Thr Gln Ser Pro Ser Ser Leu Ser Ala Ser Val Gly
```

-continued

```
1               5                   10                  15
Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
                50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Ser Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
210

<210> SEQ ID NO 18
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
                35                  40                  45

Ala Arg Ile Tyr Pro Thr Asn Gly Tyr Thr Arg Tyr Ala Asp Ser Val
                50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
```

```
            145                 150                 155                 160
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 19
<211> LENGTH: 225
<212> TYPE: PRT
<213> ORGANISM: Artificial Sequence
<220> FEATURE:
<223> OTHER INFORMATION: Synthetic polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
```

```
            50                  55                  60
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                     85                  90                  95

Thr Phe Gly Gln Gly Thr Lys Val Glu Ile Lys Arg Ser Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys Gly Gly Gly Gly Gly Cys Val Ile
            210                 215                 220

Met
225

<210> SEQ ID NO 20
<211> LENGTH: 464
<212> TYPE: PRT
<213> ORGANISM: Artificial Sequence
<220> FEATURE:
<223> OTHER INFORMATION: Synthetic polypeptide

<400> SEQUENCE: 20

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
                180             185             190
Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Gly Gly Gly Gly Cys Val Ile Met
        450                 455                 460

<210> SEQ ID NO 21
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
```

```
                85                  90                  95
Thr Phe Gly Gln Gly Thr Lys Val Glu Ile Lys Arg Ser Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
            210

<210> SEQ ID NO 22
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 22

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Arg Val Glu Pro Lys Ser Cys Asp
            210                 215                 220
Lys Thr His Thr Cys Pro Pro Cys Pro Ala Pro Glu Leu Leu Gly Gly
```

```
                225                 230                 235                 240
Pro Ser Val Phe Leu Phe Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 23
<211> LENGTH: 228
<212> TYPE: PRT
<213> ORGANISM: Artificial Sequence
<220> FEATURE:
<223> OTHER INFORMATION: Synthetic polypeptide

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Gly Gly Gly Gly
    210                 215                 220

Cys Val Ile Met
225

<210> SEQ ID NO 24
<211> LENGTH: 464
<212> TYPE: PRT
<213> ORGANISM: Artificial Sequence
<220> FEATURE:
<223> OTHER INFORMATION: Synthetic polypeptide

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
```

```
            260                 265                 270
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys Gly Gly Gly Gly Gly Gly Gly Gly Cys Val Leu Leu
        450                 455                 460

<210> SEQ ID NO 25
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                      165                 170                 175
Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 26
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
                305                 310                 315                 320
Glu Tyr Lys Cys Lys Val Ser Asn Lys Ala Leu Pro Ala Pro Ile Glu
                    325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
                355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
    450

<210> SEQ ID NO 27
<211> LENGTH: 228
<212> TYPE: PRT
<213> ORGANISM: Artificial Sequence
<220> FEATURE:
<223> OTHER INFORMATION: Synthetic polypeptide

<400> SEQUENCE: 27

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
                20                  25                  30
Val Ala Trp Tyr Gln Gln Lys Pro Gly Lys Ala Pro Lys Leu Leu Ile
            35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Arg Ser Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Gly Gly Gly Gly Gly Gly Gly Gly Gly Gly
```

```
                      210              215              220
Cys Val Leu Leu
225

<210> SEQ ID NO 28
<211> LENGTH: 4
<212> TYPE: PRT
<213> ORGANISM: Artificial Sequence
<220> FEATURE:
<223> OTHER INFORMATION: Synthetic peptide

<400> SEQUENCE: 28

Cys Val Ile Met
1

<210> SEQ ID NO 29
<211> LENGTH: 4
<212> TYPE: PRT
<213> ORGANISM: Artificial Sequence
<220> FEATURE:
<223> OTHER INFORMATION: Synthetic peptide

<400> SEQUENCE: 29

Cys Val Leu Leu
1
```